US011976383B2

(12) United States Patent
Smith et al.

(10) Patent No.: US 11,976,383 B2
(45) Date of Patent: May 7, 2024

(54) INTEGRAL MEMBRANE PROTEIN DISPLAY ON POXVIRUS EXTRACELLULAR ENVELOPED VIRIONS

(71) Applicant: VACCINEX, INC., Rochester, NY (US)

(72) Inventors: Ernest S. Smith, Rochester, NY (US); Maria G. M. Scrivens, Rochester, NY (US); Loretta Mueller, Rochester, NY (US); Shuying Shi, Rochester, NY (US); Leslie A. Balch, Rochester, NY (US)

(73) Assignee: VACCINEX, INC., Rochester, NY (US)

(*) Notice: Subject to any disclaimer, the term of this patent is extended or adjusted under 35 U.S.C. 154(b) by 373 days.

(21) Appl. No.: 17/308,167

(22) Filed: May 5, 2021

(65) Prior Publication Data
US 2021/0348158 A1    Nov. 11, 2021

Related U.S. Application Data

(60) Provisional application No. 63/020,818, filed on May 6, 2020.

(51) Int. Cl.
| | | |
|---|---|---|
| *C40B 40/08* | (2006.01) | |
| *C07K 14/005* | (2006.01) | |
| *C07K 14/705* | (2006.01) | |
| *C07K 14/715* | (2006.01) | |
| *C12N 15/10* | (2006.01) | |
| *C12N 15/62* | (2006.01) | |

(52) U.S. Cl.
CPC ............ *C40B 40/08* (2013.01); *C07K 14/005* (2013.01); *C07K 14/70596* (2013.01); *C07K 14/7158* (2013.01); *C12N 15/1037* (2013.01); *C12N 15/62* (2013.01); *C07K 2319/03* (2013.01); *C07K 2319/21* (2013.01); *C12N 2710/24022* (2013.01); *C12N 2710/24122* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 5,892,019 | A | 4/1999 | Schlom et al. |
| 7,858,559 | B2 | 12/2010 | Zauderer et al. |
| | | (Continued) | |

FOREIGN PATENT DOCUMENTS

| | | |
|---|---|---|
| JP | 2007503847 A | 3/2007 |
| WO | 1989003879 A1 | 5/1989 |
| WO | 200028016 A1 | 5/2000 |
| | (Continued) | |

OTHER PUBLICATIONS

Sambrook et al., "Molecular Cloning A Laboratory Manual", 2nd ed., Cold Spring Harbor Laboratory Press, 1989.
(Continued)

*Primary Examiner* — Christian C Boesen
(74) *Attorney, Agent, or Firm* — KDW Firm PLLC

(57) ABSTRACT

This disclosure provides compositions and methods for expressing and displaying isolated integral membrane proteins (IMPs) or fragments thereof in a native conformation on poxvirus extracellular virions and methods for screening, selecting, and identifying antibodies or antibody-like molecules that bind to a target IMP of interest.

31 Claims, 20 Drawing Sheets

Figure 1:
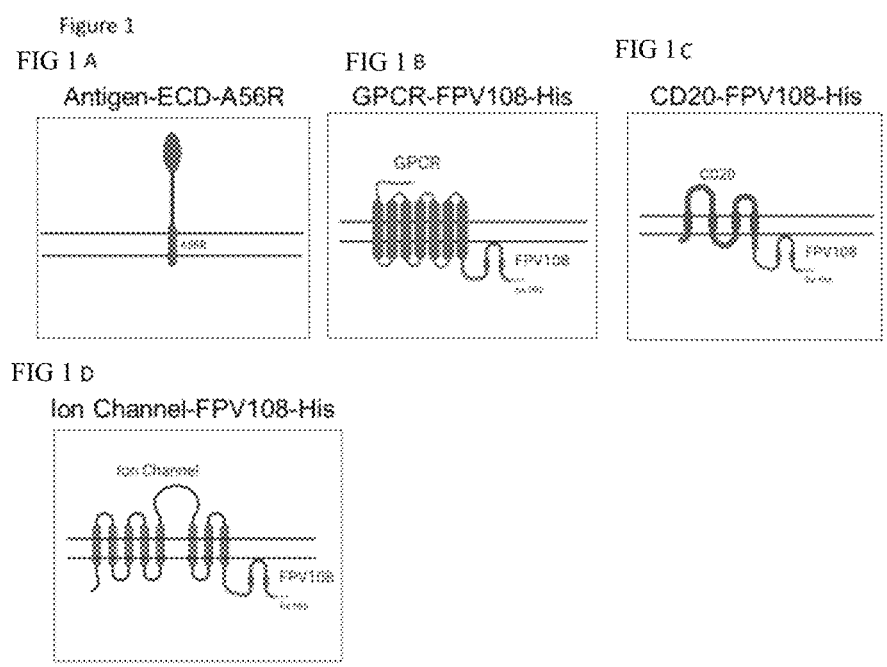

Specification includes a Sequence Listing.

(56) References Cited

U.S. PATENT DOCUMENTS

2013/0028892 A1    1/2013  MacDonald et al.

FOREIGN PATENT DOCUMENTS

| WO | 2005048957 A2 | 6/2005 |
|---|---|---|
| WO | 2013163602 A1 | 10/2013 |
| WO | 2015193143 A1 | 12/2015 |
| WO | 2017184951 A1 | 10/2017 |

OTHER PUBLICATIONS

Kabat et al., "Sequences of Proteins of Immunological Interest", U.S. Department of Health and Human Services, 1983.
Chothia et al., "Canonical Structures for the Hypervariable Regions of Immunoglobulins", Journal of Molecular Biology, 196:901-917, Aug. 20, 1987.
Brochet et al., "IMGT/V-QUEST: the Highly Customized and Integrated System for IG and TR standardized V-J and V-D-J sequence analysis", Nucleic Acids Research, 36:W503-508, 2008.
Walsh et al., "Targeting the Hepatitis B Virus Precore Antigen with a Novel IgNAR Single Variable Domain Intrabody", Virology, 411:132-141, 2011.
Harlow et al., "Antibodies: A Laboratory Manual", Cold Spring Harbor Laboratory Press, 2nd ed. 1988, pp. 27-28 and 29-34.
Fields et al., "Virology", 2d Edition, Eds., Raven Press, p. 2080, 1990.
Li et al., "Complete Coding Sequences of the Rabbitpox Virus Genome", Journal of General Virology, 86 (Pt 11):2969-77, Dec. 2005.
Moss, B., "Poxvirus DNA Replication", http://cshperspectives.cshlp.org at Univ of Rochester, May 4, 2021.
Mayr et al., "Origin, Characteristics and Uses of the Attenuated Vaccinia Strain MVA", Infection 3:6-14, 1975.
Roberts et al., "Vaccinia Virus Morphogenesis and Dissemination", Trends in Microbiology 16(10):472-479, 2008.
Smith, et al., "The Formation and Function of Extracellular Enveloped Vaccinia Virus", Journal of General Virology 83:2915-2931, 2002.
Lorenzo et al., "Intracellular Localization of Vaccinia Virus Extracellular Enveloped Virus Envelope Proteins Individually Expressed Using a Semliki Forest Virus Replicon", Journal of Virology 74(22):10535, 2000.
Fields et al., "Fields Virology", Philadelphia, Pa: Lippincott-Raven; pp. 2637-2671, 1996.
Ogawa et al., "Insertional Inactivation of a Fowlpox Virus Homologue of the Vaccinia Virus F12L Gene Inhibits the Release of Enveloped Virions", Journal of General Virology, 74: 55-64, 1993.
Ogawa et al., "Identification and Functional Analysis of the Fowlpox Virus Homolog of the Vaccinia Virus p37K Major Envelope Antigen Gene", Virology, 191: 783-792, 1992.
DeHaven et al., "The Vaccinia Virus A56 Protein: a Multifunctional Transmembrane Glycoprotein that Anchors Two Secreted Viral Proteins", Journal of General Virology, 92:1971-1980, 2011.
Gait, "Oligonucleotide Synthesis : a Practical Approach", Washington, DC: IRL Press, 1984.
Glover, "DNA cloning : a practical approach, vols. I and II", Oxford; Washington, DC: IRL Press, © 1985-© 1987.
Freshney, "Culture Of Animal Cells", Alan R. Liss, Inc.;1987.
Hames et al., "Transcription And Translation—A practical approach", pp. 328, IRL Press, Oxford. 1984.
Woodward, "Immobilized Cells And Enzymes; A Practical Approach", IRL Press, 1985.
Perbal, "A Practical Guide To Molecular Cloning", Methods In Enzymology, Academic Press, Inc., N.Y.; 1984.
Miller, "Gene Transfer Vectors For Mammalian Cells", Cold Spring Harbor Laboratory, 1987.
Wu et al., eds., "Methods In Enzymology", vols. 154 and 155.
Mayer, R.J., and Walker, J.H., "Immunochemical Methods in Cell and Molecular Biology: Biological Techniques Series", Academic Press, London 1987.
Weir and Blackwell, eds., "Handbook Of Experimental Immunology", vols. I-IV; 1986.
Hogan et al., "Manipulating the Mouse Embryo: a Laboratory Manual", Cold Spring Harbor Laboratory Press, Cold Spring Harbor, N.Y., 1986.
Ausubel et al., "Current Protocols in Molecular Biology", John Wiley and Sons, Baltimore, Md., 4648 pgs, 2003.
Borrebaeck, "Antibody Engineering", 2nd ed.; Oxford Univ. Press, 1995.
Nisonoff, "Molecular Immunology", 2nd ed.; Sinauer Associates, Sunderland, Mass, 1984.
Steward, "Antibodies, Their Structure and Function", Chapman and Hall, New York, N.Y, 1984.
John Wiley & Sons, New York; Stites et al., eds. "Basic and Clinical Immunology", 8th ed; Appleton & Lange, Norwalk, Conn., 1994.
Mishell and Shiigi, "Selected Methods in Cellular Immunology", W.H. Freeman and Co., NY, eds 1980.
John Wiley & Sons, New York; Klein, "The Science of Self-Nonself Discrimination", John Wiley & Sons, NY, J. Immunology, 1982.
Goldsby et al., "Kuby Immunology", 4th ed.; H. Freeman & Co.eds., 2000.
Abbas et al., "Cellular and Molecular Immunology", 5th ed., Elsevier Health Sciences Division, 2005.
Kontermann and Dubel, "Antibody Engineering", Springer Verlag, 2001.
Sambrook and Russell, "Molecular Cloning: A Laboratory Manual", Cold Spring Harbor Press, 2001.
Lewin, "Genes VIII", Prentice Hall, 2003.
Roitt et al. "Immunology", 6th ed.; London: Mosby, 2001.
Dieffenbach and Dveksler, "PCR Primer", Cold Spring Harbor Press, 2003.
Brummell et al., "Probing the Combining Site of an Anti-Carbohydrate Antibody by Saturation-Mutagenesis: role of the Heavy-Chain CDR3 Residues", Biochemistry, 32:1180-1, 187, 1993.
Kobayashi et al., "Tryptophan H33 Plays an Important Role in Pyrimidine (6-4) Pyrimidone Photoproduct Binding by a High-Affinity Antibody", Protein Engeneering, 12(10):879-884, 1999.
Burks et al., "In Vitro Scanning Saturation Mutagenesis of an Antibody Binding Pocket", Proc. Natl. Acad. Sci. USA, 94:412-417, 1997.
International Search Report and Written Opinion for the International Patent Application No. PCT/US2021/030781, dated Oct. 25, 2021, 19 pages.
Afonso et al., "The Genome of Fowlpox Virus", Journal of Virology, vol. 74, No. 8, Apr. 15, 2000, pp. 3815-3831.
Smith et al., "The Formation and Function of Extracellular enveloped vaccinia virus", Journal of General Virology, vol. 83, No. 12, Dec. 1, 2002, pp. 2915-2931.

Figure 1A-D

Figure 2

Rabbit Pox Strain Utrecht Genome

Figure 3

|  | VV F13L-SeqID#1 | FPV108-SeqID#2 | RPXV041-SeqID#3 |
|---|---|---|---|
| VV F13L -Seq ID#1 |  | 37.6 | 99.7 |
| FPV108- Seq ID#2 | 37.6 |  | 37.6 |
| RPXV041-SeqID#3 | 99.7 | 37.6 |  |

Figure 5

Lane:
1. Vaccinia with CD39-F13L
2. FPV with CD39-F13L
3. FPV with CD39-FPV108

**

Lane 1: Vaccinia with Sema-A56R
Lane 2: MVA with Sema-A56R
Lane 3: FPV pseudotyped by infected/transfection with transfer plasmid
Lane 4: FPV pseudotyped using QT35 cells transfected with Sema-A56R

Figure 9

Mouse Immunized Library Anti-CD20 Antibodies

| mAb number | CD20+ Wil2S GMFI over bkg | CD20 NEG GMFI over bkg |
|---|---|---|
| Mab 15661 | 604.3 | 1.2 |
| Mab15671 | 209.4 | 1.1 |
| Mab15706 | 282 | 0.9 |
| Mab15703 | 137.8 | 1.1 |
| Mab15713 | 105 | 1 |

Figure 14

MVA/FPV Anti-CD20 Antibodies

| mAb number | CD20+ Wil2S GMFI over bkg | CD20 NEG GMFI over bkg |
|---|---|---|
| Mab15630 | 91.8 | 1.0 |
| Mab15682 | 77.9 | 1.0 |
| Mab15632 | 33.1 | 0.9 |
| Mab15692 | 13.1 | 4.2 |
| Mab15621 | 10.5 | 4 |

Figure 15

SEQUENCE LISTING

<160> NUMBER OF SEQ ID NOS: 16

<210> SEQ ID NO 1
<211> LENGTH: 372
<212> TYPE: PRT
<213> ORGANISM: Vaccinia virus

<400> SEQUENCE: 1

Met Trp Pro Phe Ala Ser Val Pro Ala Gly Ala Lys Cys Arg Leu Val
1               5                   10                  15

Glu Thr Leu Pro Glu Asn Met Asp Phe Arg Ser Asp His Leu Thr Thr
            20                  25                  30

Phe Glu Cys Phe Asn Glu Ile Ile Thr Leu Ala Lys Lys Tyr Ile Tyr
        35                  40                  45

Ile Ala Ser Phe Cys Cys Asn Pro Leu Ser Thr Thr Arg Gly Ala Leu
    50                  55                  60

Ile Phe Asp Lys Leu Lys Glu Ala Ser Glu Lys Gly Ile Lys Ile Ile
65                  70                  75                  80

Val Leu Leu Asp Glu Arg Gly Lys Arg Asn Leu Gly Glu Leu Gln Ser
                85                  90                  95

His Cys Pro Asp Ile Asn Phe Ile Thr Val Asn Ile Asp Lys Lys Asn
            100                 105                 110

Asn Val Gly Leu Leu Leu Gly Cys Phe Trp Val Ser Asp Asp Glu Arg
        115                 120                 125

Cys Tyr Val Gly Asn Ala Ser Phe Thr Gly Gly Ser Ile His Thr Ile
    130                 135                 140

```
Lys Thr Leu Gly Val Tyr Ser Asp Tyr Pro Pro Leu Ala Thr Asp Leu
145                 150                 155                 160

Arg Arg Arg Phe Asp Thr Phe Lys Ala Phe Asn Ser Ala Lys Asn Ser
                165                 170                 175

Trp Leu Asn Leu Cys Ser Ala Ala Cys Cys Leu Pro Val Ser Thr Ala
            180                 185                 190

Tyr His Ile Lys Asn Pro Ile Gly Gly Val Phe Phe Thr Asp Ser Pro
        195                 200                 205

Glu His Leu Leu Gly Tyr Ser Arg Asp Leu Asp Thr Asp Val Val Ile
    210                 215                 220

Asp Lys Leu Lys Ser Ala Lys Thr Ser Ile Asp Ile Glu His Leu Ala
225                 230                 235                 240

Ile Val Pro Thr Thr Arg Val Asp Gly Asn Ser Tyr Tyr Trp Pro Asp
                245                 250                 255

Ile Tyr Asn Ser Ile Ile Glu Ala Ala Ile Asn Arg Gly Val Lys Ile
            260                 265                 270

Arg Leu Leu Val Gly Asn Trp Asp Lys Asn Asp Val Tyr Ser Met Ala
        275                 280                 285

Thr Ala Arg Ser Leu Asp Ala Leu Cys Val Gln Asn Asp Leu Ser Val
    290                 295                 300

Lys Val Phe Thr Ile Gln Asn Asn Thr Lys Leu Leu Ile Val Asp Asp
305                 310                 315                 320

Glu Tyr Val His Ile Thr Ser Ala Asn Phe Asp Gly Thr His Tyr Gln
                325                 330                 335

Asn His Gly Phe Val Ser Phe Asn Ser Ile Asp Lys Gln Leu Val Ser
            340                 345                 350

Glu Ala Lys Lys Ile Phe Glu Arg Asp Trp Val Ser Ser His Ser Lys
        355                 360                 365

Ser Leu Lys Ile
    370

<210> SEQ ID NO 2
<211> LENGTH: 377
<212> TYPE: PRT
<213> ORGANISM: Fowlpox virus

<400> SEQUENCE: 2

Met Gly Asn Ile Phe Lys Pro Ile Pro Lys Ala Asp Tyr Gln Ile Val
1               5                   10                  15

Glu Thr Val Pro Gln Ser Leu Thr Ala Ile Asn Ser Thr Asn Leu Ser
            20                  25                  30

Thr Tyr Glu Cys Phe Lys Arg Leu Ile Asp Leu Ala Lys Lys Glu Ile
        35                  40                  45

Tyr Ile Ala Thr Phe Cys Cys Asn Leu Ser Thr Asn Pro Glu Gly Thr
    50                  55                  60

Asp Ile Leu Asn Arg Leu Ile Asp Val Ser Ser Lys Val Ser Val Tyr
65                  70                  75                  80

Ile Leu Val Asp Glu Ser Ser Pro His Lys Asp Tyr Glu Lys Ile Lys
                85                  90                  95

Ser Ser His Ile Ser Tyr Ile Lys Val Asp Ile Gly Val Leu Asn Asn
            100                 105                 110

Glu Ser Val Gly Asn Leu Leu Gly Asn Phe Trp Val Val Asp Lys Leu
        115                 120                 125

His Phe Tyr Ile Gly Ser Ala Ser Leu Met Gly Asn Ala Leu Thr Thr
```

```
                130                 135                 140
Ile Lys Asn Met Gly Ile Tyr Ser Glu Asn Asn Ser Leu Ala Met Asp
145                 150                 155                 160

Leu Tyr Phe Arg Ser Leu Asp Tyr Lys Ile Ile Ser Lys Lys Lys Cys
                165                 170                 175

Leu Phe Phe Thr Arg Met Ala Thr Lys Tyr His Phe Lys Asn His
                180                 185                 190

Asn Gly Ile Phe Phe Ser Asp Ser Pro Glu His Met Val Gly Arg Lys
                195                 200                 205

Arg Thr Phe Asp Leu Asp Cys Val Ile His Tyr Ile Asp Ala Ala Lys
                210                 215                 220

Ser Thr Ile Asp Leu Ala Ile Val Ser Leu Leu Pro Thr Lys Arg Thr
225                 230                 235                 240

Lys Asp Ser Ile Val Tyr Trp Pro Ile Ile Lys Asp Ala Leu Ile Arg
                245                 250                 255

Ala Val Leu Glu Arg Gly Val Lys Leu Arg Val Leu Leu Gly Phe Trp
                260                 265                 270

Lys Lys Thr Asp Val Ile Ser Lys Ala Ser Ile Lys Ser Leu Asn Glu
                275                 280                 285

Leu Gly Val Asp His Ile Asp Ile Ser Thr Lys Val Phe Arg Phe Pro
                290                 295                 300

Val Asn Ser Lys Val Asp Asp Ile Asn Asn Ser Lys Met Met Ile Ile
305                 310                 315                 320

Asp Gly Arg Tyr Ala His Val Met Thr Ala Asn Leu Asp Gly Ser His
                325                 330                 335

Phe Asn His His Ala Phe Val Ser Phe Asn Cys Met Asp Gln Gln Phe
                340                 345                 350

Thr Lys Lys Ile Ala Glu Val Phe Glu Arg Asp Trp Ile Ser Pro Tyr
                355                 360                 365

Ala Lys Glu Ile Asp Met Ser Gln Ile
                370                 375

<210> SEQ ID NO 3
<211> LENGTH: 372
<212> TYPE: PRT
<213> ORGANISM: Vaccinia virus

<400> SEQUENCE: 3

Met Trp Pro Phe Ala Pro Val Pro Ala Gly Ala Lys Cys Arg Leu Val
1                 5                   10                  15

Glu Thr Leu Pro Glu Asn Met Asp Phe Arg Ser Asp His Leu Thr Thr
                20                  25                  30

Phe Glu Cys Phe Asn Glu Ile Ile Thr Leu Ala Lys Lys Tyr Ile Tyr
                35                  40                  45

Ile Ala Ser Phe Cys Cys Asn Pro Leu Ser Thr Thr Arg Gly Ala Leu
                50                  55                  60

Ile Phe Asp Lys Leu Lys Glu Ala Ser Glu Lys Gly Ile Lys Ile Ile
65                  70                  75                  80

Val Leu Leu Asp Glu Arg Gly Lys Arg Asn Leu Gly Glu Leu Gln Ser
                85                  90                  95

His Cys Pro Asp Ile Asn Phe Ile Thr Val Asn Ile Asp Lys Lys Asn
                100                 105                 110

Asn Val Gly Leu Leu Leu Gly Cys Phe Trp Val Ser Asp Asp Glu Arg
                115                 120                 125
```

```
Cys Tyr Val Gly Asn Ala Ser Phe Thr Gly Gly Ser Ile His Thr Ile
    130                 135                 140

Lys Thr Leu Gly Val Tyr Ser Asp Tyr Pro Pro Leu Ala Thr Asp Leu
145                 150                 155                 160

Arg Arg Arg Phe Asp Thr Phe Lys Ala Phe Asn Ser Ala Lys Asn Ser
                165                 170                 175

Trp Leu Asn Leu Cys Ser Ala Ala Cys Cys Leu Pro Val Ser Thr Ala
            180                 185                 190

Tyr His Ile Lys Asn Pro Ile Gly Gly Val Phe Phe Thr Asp Ser Pro
        195                 200                 205

Glu His Leu Leu Gly Tyr Ser Arg Asp Leu Asp Thr Asp Val Val Ile
    210                 215                 220

Asp Lys Leu Lys Ser Ala Lys Thr Ser Ile Asp Ile Glu His Leu Ala
225                 230                 235                 240

Ile Val Pro Thr Thr Arg Val Asp Gly Asn Ser Tyr Tyr Trp Pro Asp
                245                 250                 255

Ile Tyr Asn Ser Ile Ile Glu Ala Ala Ile Asn Arg Gly Val Lys Ile
            260                 265                 270

Arg Leu Leu Val Gly Asn Trp Asp Lys Asn Asp Val Tyr Ser Met Ala
        275                 280                 285

Thr Ala Arg Ser Leu Asp Ala Leu Cys Val Gln Asn Asp Leu Ser Val
    290                 295                 300

Lys Val Phe Thr Ile Gln Asn Asn Thr Lys Leu Leu Ile Val Asp Asp
305                 310                 315                 320

Glu Tyr Val His Ile Thr Ser Ala Asn Phe Asp Gly Thr His Tyr Gln
                325                 330                 335

Asn His Gly Phe Val Ser Phe Asn Ser Ile Asp Lys Gln Leu Val Ser
            340                 345                 350

Glu Ala Lys Lys Ile Phe Glu Arg Asp Trp Val Ser Ser His Ser Lys
        355                 360                 365

Ser Leu Lys Ile
    370

<210> SEQ ID NO 4
<211> LENGTH: 917
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Trp Ser Cys Ile Ile Leu Phe Leu Val Ala Thr Ala Thr Gly
1               5                   10                  15

Ala His Ser Phe Gly Asp Glu Glu Arg Arg Cys Asp Pro Ile Arg
                20                  25                  30

Ile Ser Met Cys Gln Asn Leu Gly Tyr Asn Val Thr Lys Met Pro Asn
            35                  40                  45

Leu Val Gly His Glu Leu Gln Thr Asp Ala Glu Leu Gln Leu Thr Thr
        50                  55                  60

Phe Thr Pro Leu Ile Gln Tyr Gly Cys Ser Ser Gln Leu Gln Phe Phe
65                  70                  75                  80

Leu Cys Ser Val Tyr Val Pro Met Cys Thr Glu Lys Ile Asn Ile Pro
                85                  90                  95

Ile Gly Pro Cys Gly Gly Met Cys Leu Ser Val Lys Arg Arg Cys Glu
            100                 105                 110
```

```
Pro Val Leu Lys Glu Phe Gly Phe Ala Trp Pro Glu Ser Leu Asn Cys
            115                 120                 125

Ser Lys Phe Pro Pro Gln Asn Asp His Asn His Met Cys Met Glu Gly
        130                 135                 140

Pro Gly Asp Glu Glu Val Pro Leu Pro His Lys Thr Pro Ile Gln Pro
145                 150                 155                 160

Gly Glu Glu Cys His Ser Val Gly Thr Asn Ser Asp Gln Tyr Ile Trp
                165                 170                 175

Val Lys Arg Ser Leu Asn Cys Val Leu Lys Cys Gly Tyr Asp Ala Gly
            180                 185                 190

Leu Tyr Ser Arg Ser Ala Lys Glu Phe Thr Asp Ile Trp Met Ala Val
            195                 200                 205

Trp Ala Ser Leu Cys Phe Ile Ser Thr Ala Phe Thr Val Leu Thr Phe
        210                 215                 220

Leu Ile Asp Ser Ser Arg Phe Ser Tyr Pro Glu Arg Pro Ile Ile Phe
225                 230                 235                 240

Leu Ser Met Cys Tyr Asn Ile Tyr Ser Ile Ala Tyr Ile Val Arg Leu
                245                 250                 255

Thr Val Gly Arg Glu Arg Ile Ser Cys Asp Phe Glu Glu Ala Ala Glu
            260                 265                 270

Pro Val Leu Ile Gln Glu Gly Leu Lys Asn Thr Gly Cys Ala Ile Ile
        275                 280                 285

Phe Leu Leu Met Tyr Phe Phe Gly Met Ala Ser Ser Ile Trp Trp Val
        290                 295                 300

Ile Leu Thr Leu Thr Trp Phe Leu Ala Ala Gly Leu Lys Trp Gly His
305                 310                 315                 320

Glu Ala Ile Glu Met His Ser Ser Tyr Phe His Ile Ala Ala Trp Ala
                325                 330                 335

Ile Pro Ala Val Lys Thr Ile Val Ile Leu Ile Met Arg Leu Val Asp
            340                 345                 350

Ala Asp Glu Leu Thr Gly Leu Cys Tyr Val Gly Asn Gln Asn Leu Asp
            355                 360                 365

Ala Leu Thr Gly Phe Val Val Ala Pro Leu Phe Thr Tyr Leu Val Ile
        370                 375                 380

Gly Thr Leu Phe Ile Ala Ala Gly Leu Val Ala Leu Phe Lys Ile Arg
385                 390                 395                 400

Ser Asn Leu Gln Lys Asp Gly Thr Lys Thr Asp Lys Leu Glu Arg Leu
                405                 410                 415

Met Val Lys Ile Gly Val Phe Ser Val Leu Tyr Thr Val Pro Ala Thr
            420                 425                 430

Cys Val Ile Ala Cys Tyr Phe Tyr Glu Ile Ser Asn Trp Ala Leu Phe
            435                 440                 445

Arg Tyr Ser Ala Asp Asp Ser Asn Met Ala Val Glu Met Leu Lys Ile
450                 455                 460

Phe Met Ser Leu Leu Val Gly Ile Thr Ser Gly Met Trp Ile Trp Ser
465                 470                 475                 480

Ala Lys Thr Leu His Thr Trp Gln Lys Cys Ser Asn Arg Leu Val Asn
                485                 490                 495

Ser Gly Lys Val Lys Arg Glu Lys Arg Gly Asn Gly Trp Val Lys Pro
            500                 505                 510

Gly Lys Gly Ser Glu Thr Val Val Val His His His His His Gly
            515                 520                 525
```

Gly Gly Gly Ser Gly Ser Leu Gly Gly Ser Ser Gly Met Gly Asn Ile
530                 535                 540

Phe Lys Pro Ile Pro Lys Ala Asp Tyr Gln Ile Val Glu Thr Val Pro
545                 550                 555                 560

Gln Ser Leu Thr Ala Ile Asn Ser Thr Asn Leu Ser Thr Tyr Glu Cys
            565                 570                 575

Phe Lys Arg Leu Ile Asp Leu Ala Lys Lys Glu Ile Tyr Ile Ala Thr
            580                 585                 590

Phe Cys Cys Asn Leu Ser Thr Asn Pro Glu Gly Thr Asp Ile Leu Asn
        595                 600                 605

Arg Leu Ile Asp Val Ser Ser Lys Val Ser Val Tyr Ile Leu Val Asp
        610                 615                 620

Glu Ser Ser Pro His Lys Asp Tyr Glu Lys Ile Lys Ser Ser His Ile
625                 630                 635                 640

Ser Tyr Ile Lys Val Asp Ile Gly Val Leu Asn Asn Glu Ser Val Gly
                645                 650                 655

Asn Leu Leu Gly Asn Phe Trp Val Val Asp Lys Leu His Phe Tyr Ile
            660                 665                 670

Gly Ser Ala Ser Leu Met Gly Asn Ala Leu Thr Thr Ile Lys Asn Met
        675                 680                 685

Gly Ile Tyr Ser Glu Asn Asn Ser Leu Ala Met Asp Leu Tyr Phe Arg
        690                 695                 700

Ser Leu Asp Tyr Lys Ile Ile Ser Lys Lys Cys Leu Phe Phe Thr
705                 710                 715                 720

Arg Met Ala Thr Lys Tyr His Phe Phe Lys Asn His Asn Gly Ile Phe
                725                 730                 735

Phe Ser Asp Ser Pro Glu His Met Val Gly Arg Lys Arg Thr Phe Asp
            740                 745                 750

Leu Asp Cys Val Ile His Tyr Ile Asp Ala Ala Lys Ser Thr Ile Asp
        755                 760                 765

Leu Ala Ile Val Ser Leu Leu Pro Thr Lys Arg Thr Lys Asp Ser Ile
        770                 775                 780

Val Tyr Trp Pro Ile Ile Lys Asp Ala Leu Ile Arg Ala Val Leu Glu
785                 790                 795                 800

Arg Gly Val Lys Leu Arg Val Leu Leu Gly Phe Trp Lys Lys Thr Asp
                805                 810                 815

Val Ile Ser Lys Ala Ser Ile Lys Ser Leu Asn Glu Leu Gly Val Asp
            820                 825                 830

His Ile Asp Ile Ser Thr Lys Val Phe Arg Phe Pro Val Asn Ser Lys
        835                 840                 845

Val Asp Asp Ile Asn Asn Ser Lys Met Met Ile Asp Gly Arg Tyr
850                 855                 860

Ala His Val Met Thr Ala Asn Leu Asp Gly Ser His Phe Asn His His
865                 870                 875                 880

Ala Phe Val Ser Phe Asn Cys Met Asp Gln Gln Phe Thr Lys Lys Ile
                885                 890                 895

Ala Glu Val Phe Glu Arg Asp Trp Ile Ser Pro Tyr Ala Lys Glu Ile
            900                 905                 910

Asp Met Ser Gln Ile
            915

<210> SEQ ID NO 5
<211> LENGTH: 314
<212> TYPE: PRT

-continued

<213> ORGANISM: Vaccinia virus

<400> SEQUENCE: 5

Met Thr Arg Leu Pro Ile Leu Leu Leu Leu Ile Ser Leu Val Tyr Ala
1 5 10 15

Thr Pro Phe Pro Gln Thr Ser Lys Lys Ile Gly Asp Asp Ala Thr Leu
20 25 30

Ser Cys Asn Arg Asn Asn Thr Asn Asp Tyr Val Val Met Ser Ala Trp
35 40 45

Tyr Lys Glu Pro Asn Ser Ile Ile Leu Leu Ala Ala Lys Ser Asp Val
50 55 60

Leu Tyr Phe Asp Asn Tyr Thr Lys Asp Lys Ile Ser Tyr Asp Ser Pro
65 70 75 80

Tyr Asp Asp Leu Val Thr Thr Ile Thr Ile Lys Ser Leu Thr Ala Arg
85 90 95

Asp Ala Gly Thr Tyr Val Cys Ala Phe Phe Met Thr Ser Thr Thr Asn
100 105 110

Asp Thr Asp Lys Val Asp Tyr Glu Glu Tyr Ser Thr Glu Leu Ile Val
115 120 125

Asn Thr Asp Ser Glu Ser Thr Ile Asp Ile Ile Leu Ser Gly Ser Thr
130 135 140

His Ser Pro Glu Thr Ser Ser Lys Lys Pro Asp Tyr Ile Asp Asn Ser
145 150 155 160

Asn Cys Ser Ser Val Phe Glu Ile Ala Thr Pro Glu Pro Ile Thr Asp
165 170 175

Asn Val Glu Asp His Thr Asp Thr Val Thr Tyr Thr Ser Asp Ser Ile
180 185 190

Asn Thr Val Ser Ala Ser Ser Gly Glu Ser Thr Thr Asp Glu Thr Pro
195 200 205

Glu Pro Ile Thr Asp Lys Glu Asp His Thr Val Thr Asp Thr Val Ser
210 215 220

Tyr Thr Thr Val Ser Thr Ser Ser Gly Ile Val Thr Thr Lys Ser Thr
225 230 235 240

Thr Asp Asp Ala Asp Leu Tyr Asp Thr Tyr Asn Asp Asn Asp Thr Val
245 250 255

Pro Pro Thr Thr Val Gly Gly Ser Thr Thr Ser Ile Ser Asn Tyr Lys
260 265 270

Thr Lys Asp Phe Val Glu Ile Phe Gly Ile Thr Ala Leu Ile Ile Leu
275 280 285

Ser Ala Val Ala Ile Phe Cys Ile Thr Tyr Tyr Ile Tyr Asn Lys Arg
290 295 300

Ser Arg Lys Tyr Lys Thr Glu Asn Lys Val
305 310

<210> SEQ ID NO 6
<211> LENGTH: 935
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

Met Gly Trp Ser Cys Ile Ile Leu Phe Leu Val Ala Thr Ala Thr Gly
1 5 10 15

Ala His Ser Phe Ala Pro Ile Pro Arg Ile Thr Trp Glu His Arg Glu

-continued

```
            20                  25                  30
Val His Leu Val Gln Phe His Glu Pro Asp Ile Tyr Asn Tyr Ser Ala
             35                  40                  45
Leu Leu Leu Ser Glu Asp Lys Asp Thr Leu Tyr Ile Gly Ala Arg Glu
         50                  55                  60
Ala Val Phe Ala Val Asn Ala Leu Asn Ile Ser Glu Lys Gln His Glu
 65                  70                  75                  80
Val Tyr Trp Lys Val Ser Glu Asp Lys Lys Ala Lys Cys Ala Glu Lys
                 85                  90                  95
Gly Lys Ser Lys Gln Thr Glu Cys Leu Asn Tyr Ile Arg Val Leu Gln
            100                 105                 110
Pro Leu Ser Ala Thr Ser Leu Tyr Val Cys Gly Thr Asn Ala Phe Gln
            115                 120                 125
Pro Ala Cys Asp His Leu Asn Leu Thr Ser Phe Lys Phe Leu Gly Lys
            130                 135                 140
Asn Glu Asp Gly Lys Gly Arg Cys Pro Phe Asp Pro Ala His Ser Tyr
145                 150                 155                 160
Thr Ser Val Met Val Asp Gly Glu Leu Tyr Ser Gly Thr Ser Tyr Asn
                165                 170                 175
Phe Leu Gly Ser Glu Pro Ile Ile Ser Arg Asn Ser Ser His Ser Pro
            180                 185                 190
Leu Arg Thr Glu Tyr Ala Ile Pro Trp Leu Asn Glu Pro Ser Phe Val
            195                 200                 205
Phe Ala Asp Val Ile Arg Lys Ser Pro Asp Ser Pro Asp Gly Glu Asp
            210                 215                 220
Asp Arg Val Tyr Phe Phe Phe Thr Glu Val Ser Val Glu Tyr Glu Phe
225                 230                 235                 240
Val Phe Arg Val Leu Ile Pro Arg Ile Ala Arg Val Cys Lys Gly Asp
                245                 250                 255
Gln Gly Gly Leu Arg Thr Leu Gln Lys Lys Trp Thr Ser Phe Leu Lys
            260                 265                 270
Ala Arg Leu Ile Cys Ser Arg Pro Asp Ser Gly Leu Val Phe Asn Val
            275                 280                 285
Leu Arg Asp Val Phe Val Leu Arg Ser Pro Gly Leu Lys Val Pro Val
        290                 295                 300
Phe Tyr Ala Leu Phe Thr Pro Gln Leu Asn Asn Val Gly Leu Ser Ala
305                 310                 315                 320
Val Cys Ala Tyr Asn Leu Ser Thr Ala Glu Glu Val Phe Ser His Gly
                325                 330                 335
Lys Tyr Met Gln Ser Thr Thr Val Glu Gln Ser His Thr Lys Trp Val
            340                 345                 350
Arg Tyr Asn Gly Pro Val Pro Lys Pro Arg Pro Gly Ala Cys Ile Asp
            355                 360                 365
Ser Glu Ala Arg Ala Ala Asn Tyr Thr Ser Ser Leu Asn Leu Pro Asp
        370                 375                 380
Lys Thr Leu Gln Phe Val Lys Asp His Pro Leu Met Asp Asp Ser Val
385                 390                 395                 400
Thr Pro Ile Asp Asn Arg Pro Arg Leu Ile Lys Lys Asp Val Asn Tyr
                405                 410                 415
Thr Gln Ile Val Val Asp Arg Thr Gln Ala Leu Asp Gly Thr Val Tyr
            420                 425                 430
Asp Val Met Phe Val Ser Thr Asp Arg Gly Ala Leu His Lys Ala Ile
            435                 440                 445
```

```
Ser Leu Glu His Ala Val His Ile Glu Glu Thr Gln Leu Phe Gln
    450                 455                 460

Asp Phe Glu Pro Val Gln Thr Leu Leu Ser Ser Lys Lys Gly Asn
465                 470                 475                 480

Arg Phe Val Tyr Ala Gly Ser Asn Ser Gly Val Val Gln Ala Pro Leu
                    485                 490                 495

Ala Phe Cys Gly Lys His Gly Thr Cys Glu Asp Cys Val Leu Ala Arg
                500                 505                 510

Asp Pro Tyr Cys Ala Trp Ser Pro Pro Thr Ala Thr Cys Val Ala Leu
            515                 520                 525

His Gln Thr Glu Ser Pro Ser Arg Gly Leu Ile Gln Glu Met Ser Gly
        530                 535                 540

Asp Ala Ser Val Cys Pro Asp Lys Ser Lys Gly Ser Tyr Arg Gln His
545                 550                 555                 560

Phe Phe Lys His Gly Gly Thr Ala Glu Leu Lys Cys Ser Gln Lys Ser
                565                 570                 575

Asn Leu Ala Arg Val Phe Trp Lys Phe Gln Asn Gly Val Leu Lys Ala
                580                 585                 590

Glu Ser Pro Lys Tyr Gly Leu Met Gly Arg Lys Asn Leu Leu Ile Phe
            595                 600                 605

Asn Leu Ser Glu Gly Asp Ser Gly Val Tyr Gln Cys Leu Ser Glu Glu
            610                 615                 620

Arg Val Lys Asn Lys Thr Val Phe Gln Val Val Ala Lys His Val Leu
625                 630                 635                 640

Glu Val Lys Val Val Pro Lys Pro Val Val Ala Pro Thr Leu Ser Val
                    645                 650                 655

Val Gln Thr Glu Gly Ser Arg Ile Ala Thr Lys Val Leu Val Ala Ser
            660                 665                 670

Thr Gln Gly Ser Ser Pro Pro Thr Pro Ala Val Gln Ala Thr Ser Ser
            675                 680                 685

Gly Ala Ile Thr Leu Pro Pro Lys Pro Ala Pro Thr Gly Thr Ser Cys
            690                 695                 700

Glu Pro Lys Ile Val Ile Asn Thr Val Pro Gln Leu His Ser Glu Lys
705                 710                 715                 720

Thr Met Tyr Leu Lys Ser Ser Asp Thr Ser Thr Thr Asn Asp Thr Asp
                    725                 730                 735

Lys Val Asp Tyr Glu Glu Tyr Ser Thr Glu Leu Ile Val Asn Thr Asp
                740                 745                 750

Ser Glu Ser Thr Ile Asp Ile Ile Leu Ser Gly Ser Thr His Ser Pro
            755                 760                 765

Glu Thr Ser Ser Lys Lys Pro Asp Tyr Ile Asp Asn Ser Asn Cys Ser
        770                 775                 780

Ser Val Phe Glu Ile Ala Thr Pro Glu Pro Ile Thr Asp Asn Val Glu
785                 790                 795                 800

Asp His Thr Asp Thr Val Thr Tyr Thr Ser Asp Ser Ile Asn Thr Val
                    805                 810                 815

Ser Ala Ser Ser Gly Glu Ser Thr Thr Asp Glu Thr Pro Glu Pro Ile
                820                 825                 830

Thr Asp Lys Glu Asp His Thr Val Thr Asp Thr Val Ser Tyr Thr Thr
            835                 840                 845

Val Ser Thr Ser Ser Gly Ile Val Thr Thr Lys Ser Thr Thr Asp Asp
        850                 855                 860
```

```
Ala Asp Leu Tyr Asp Thr Tyr Asn Asp Asn Asp Thr Val Pro Pro Thr
865                 870                 875                 880

Thr Val Gly Gly Ser Thr Thr Ser Ile Ser Asn Tyr Lys Thr Lys Asp
            885                 890                 895

Phe Val Glu Ile Phe Gly Ile Thr Ala Leu Ile Ile Leu Ser Ala Val
        900                 905                 910

Ala Ile Phe Cys Ile Thr Tyr Tyr Ile Tyr Asn Lys Arg Ser Arg Lys
        915                 920                 925

Tyr Lys Thr Glu Asn Lys Val
        930                 935

<210> SEQ ID NO 7
<211> LENGTH: 855
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Trp Ser Cys Ile Ile Leu Phe Leu Val Ala Thr Ala Thr Gly
1               5                   10                  15

Ala His Ser Ser Thr Gln Val Cys Thr Gly Thr Asp Met Lys Leu Arg
            20                  25                  30

Leu Pro Ala Ser Pro Glu Thr His Leu Asp Met Leu Arg His Leu Tyr
        35                  40                  45

Gln Gly Cys Gln Val Val Gln Gly Asn Leu Glu Leu Thr Tyr Leu Pro
    50                  55                  60

Thr Asn Ala Ser Leu Ser Phe Leu Gln Asp Ile Gln Glu Val Gln Gly
65                  70                  75                  80

Tyr Val Leu Ile Ala His Asn Gln Val Arg Gln Val Pro Leu Gln Arg
                85                  90                  95

Leu Arg Ile Val Arg Gly Thr Gln Leu Phe Glu Asp Asn Tyr Ala Leu
            100                 105                 110

Ala Val Leu Asp Asn Gly Asp Pro Leu Asn Asn Thr Thr Pro Val Thr
        115                 120                 125

Gly Ala Ser Pro Gly Gly Leu Arg Glu Leu Gln Leu Arg Ser Leu Thr
    130                 135                 140

Glu Ile Leu Lys Gly Gly Val Leu Ile Gln Arg Asn Pro Gln Leu Cys
145                 150                 155                 160

Tyr Gln Asp Thr Ile Leu Trp Lys Asp Ile Phe His Lys Asn Asn Gln
                165                 170                 175

Leu Ala Leu Thr Leu Ile Asp Thr Asn Arg Ser Arg Ala Cys His Pro
            180                 185                 190

Cys Ser Pro Met Cys Lys Gly Ser Arg Cys Trp Gly Glu Ser Ser Glu
        195                 200                 205

Asp Cys Gln Ser Leu Thr Arg Thr Val Cys Ala Gly Gly Cys Ala Arg
    210                 215                 220

Cys Lys Gly Pro Leu Pro Thr Asp Cys Cys His Glu Gln Cys Ala Ala
225                 230                 235                 240

Gly Cys Thr Gly Pro Lys His Ser Asp Cys Leu Ala Cys Leu His Phe
                245                 250                 255

Asn His Ser Gly Ile Cys Glu Leu His Cys Pro Ala Leu Val Thr Tyr
            260                 265                 270

Asn Thr Asp Thr Phe Glu Ser Met Pro Asn Pro Glu Gly Arg Tyr Thr
        275                 280                 285
```

```
Phe Gly Ala Ser Cys Val Thr Ala Cys Pro Tyr Asn Tyr Leu Ser Thr
    290                 295                 300
Asp Val Gly Ser Cys Thr Leu Val Cys Pro Leu His Asn Gln Glu Val
305                 310                 315                 320
Thr Ala Glu Asp Gly Thr Gln Arg Cys Glu Lys Cys Ser Lys Pro Cys
                325                 330                 335
Ala Arg Val Cys Tyr Gly Leu Gly Met Glu His Leu Arg Glu Val Arg
            340                 345                 350
Ala Val Thr Ser Ala Asn Ile Gln Glu Phe Ala Gly Cys Lys Lys Ile
        355                 360                 365
Phe Gly Ser Leu Ala Phe Leu Pro Glu Ser Phe Asp Gly Asp Pro Ala
370                 375                 380
Ser Asn Thr Ala Pro Leu Gln Pro Glu Gln Leu Gln Val Phe Glu Thr
385                 390                 395                 400
Leu Glu Glu Ile Thr Gly Tyr Leu Tyr Ile Ser Ala Trp Pro Asp Ser
                405                 410                 415
Leu Pro Asp Leu Ser Val Phe Gln Asn Leu Gln Val Ile Arg Gly Arg
            420                 425                 430
Ile Leu His Asn Gly Ala Tyr Ser Leu Thr Leu Gln Gly Leu Gly Ile
        435                 440                 445
Ser Trp Leu Gly Leu Arg Ser Leu Arg Glu Leu Gly Ser Gly Leu Ala
450                 455                 460
Leu Ile His His Asn Thr His Leu Cys Phe Val His Thr Val Pro Trp
465                 470                 475                 480
Asp Gln Leu Phe Arg Asn Pro His Gln Ala Leu Leu His Thr Ala Asn
                485                 490                 495
Arg Pro Glu Asp Glu Cys Val Gly Glu Gly Leu Ala Cys His Gln Leu
            500                 505                 510
Cys Ala Arg Gly His Cys Trp Gly Pro Gly Pro Thr Gln Cys Val Asn
        515                 520                 525
Cys Ser Gln Phe Leu Arg Gly Gln Glu Cys Val Glu Glu Cys Arg Val
530                 535                 540
Leu Gln Gly Leu Pro Arg Glu Tyr Val Asn Ala Arg His Cys Leu Pro
545                 550                 555                 560
Cys His Pro Glu Cys Gln Pro Gln Asn Gly Ser Val Thr Cys Phe Gly
                565                 570                 575
Pro Glu Ala Asp Gln Cys Val Ala Cys Ala His Tyr Lys Asp Pro Pro
            580                 585                 590
Phe Cys Val Ala Arg Cys Pro Ser Gly Val Lys Pro Asp Leu Ser Tyr
        595                 600                 605
Met Pro Ile Trp Lys Phe Pro Asp Glu Glu Gly Ala Cys Gln Pro Cys
610                 615                 620
Pro Ile Asn Cys Thr His Ser Cys Val Asp Leu Asp Asp Lys Gly Cys
625                 630                 635                 640
Pro Ala Glu Gln Arg Ala Ser Pro Thr Ser Thr Asn Asp Thr Asp
                645                 650                 655
Lys Val Asp Tyr Glu Glu Tyr Ser Thr Glu Leu Ile Val Asn Thr Asp
            660                 665                 670
Ser Glu Ser Thr Ile Asp Ile Ile Leu Ser Gly Ser Thr His Ser Pro
        675                 680                 685
Glu Thr Ser Ser Lys Lys Pro Asp Tyr Ile Asp Asn Ser Asn Cys Ser
690                 695                 700
```

```
Ser Val Phe Glu Ile Ala Thr Pro Glu Pro Ile Thr Asp Asn Val Glu
705                 710                 715                 720

Asp His Thr Asp Thr Val Thr Tyr Thr Ser Asp Ser Ile Asn Thr Val
            725                 730                 735

Ser Ala Ser Ser Gly Glu Ser Thr Thr Asp Glu Thr Pro Glu Pro Ile
            740                 745                 750

Thr Asp Lys Glu Asp His Thr Val Thr Asp Thr Val Ser Tyr Thr Thr
            755                 760                 765

Val Ser Thr Ser Ser Gly Ile Val Thr Thr Lys Ser Thr Thr Asp Asp
            770                 775                 780

Ala Asp Leu Tyr Asp Thr Tyr Asn Asp Asn Asp Thr Val Pro Pro Thr
785                 790                 795                 800

Thr Val Gly Gly Ser Thr Thr Ser Ile Ser Asn Tyr Lys Thr Lys Asp
                805                 810                 815

Phe Val Glu Ile Phe Gly Ile Thr Ala Leu Ile Ile Leu Ser Ala Val
                820                 825                 830

Ala Ile Phe Cys Ile Thr Tyr Tyr Ile Tyr Asn Lys Arg Ser Arg Lys
            835                 840                 845

Tyr Lys Thr Glu Asn Lys Val
    850                 855

<210> SEQ ID NO 8
<211> LENGTH: 935
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Trp Ser Cys Ile Ile Leu Phe Leu Val Ala Thr Ala Thr Gly
1               5                   10                  15

Ala His Ser Phe Ala Pro Ile Pro Arg Ile Thr Trp Glu His Arg Glu
            20                  25                  30

Val His Leu Val Gln Phe His Glu Pro Asp Ile Tyr Asn Tyr Ser Ala
        35                  40                  45

Leu Leu Leu Ser Glu Asp Lys Asp Thr Leu Tyr Ile Gly Ala Arg Glu
    50                  55                  60

Ala Val Phe Ala Val Asn Ala Leu Asn Ile Ser Glu Lys Gln His Glu
65                  70                  75                  80

Val Tyr Trp Lys Val Ser Glu Asp Lys Lys Ala Lys Cys Ala Glu Lys
                85                  90                  95

Gly Lys Ser Lys Gln Thr Glu Cys Leu Asn Tyr Ile Arg Val Leu Gln
            100                 105                 110

Pro Leu Ser Ala Thr Ser Leu Tyr Val Cys Gly Thr Asn Ala Phe Gln
        115                 120                 125

Pro Ala Cys Asp His Leu Asn Leu Thr Ser Phe Lys Phe Leu Gly Lys
    130                 135                 140

Asn Glu Asp Gly Lys Gly Arg Cys Pro Phe Asp Pro Ala His Ser Tyr
145                 150                 155                 160

Thr Ser Val Met Val Asp Gly Glu Leu Tyr Ser Gly Thr Ser Tyr Asn
                165                 170                 175

Phe Leu Gly Ser Glu Pro Ile Ile Ser Arg Asn Ser Ser His Ser Pro
            180                 185                 190

Leu Arg Thr Glu Tyr Ala Ile Pro Trp Leu Asn Glu Pro Ser Phe Val
        195                 200                 205
```

```
Phe Ala Asp Val Ile Arg Lys Ser Pro Asp Ser Pro Asp Gly Glu Asp
    210                 215                 220

Asp Arg Val Tyr Phe Phe Thr Glu Val Ser Val Glu Tyr Glu Phe
225                 230                 235                 240

Val Phe Arg Val Leu Ile Pro Arg Ile Ala Arg Val Cys Lys Gly Asp
                245                 250                 255

Gln Gly Gly Leu Arg Thr Leu Gln Lys Lys Trp Thr Ser Phe Leu Lys
            260                 265                 270

Ala Arg Leu Ile Cys Ser Arg Pro Asp Ser Gly Leu Val Phe Asn Val
        275                 280                 285

Leu Arg Asp Val Phe Val Leu Arg Ser Pro Gly Leu Lys Val Pro Val
    290                 295                 300

Phe Tyr Ala Leu Phe Thr Pro Gln Leu Asn Asn Val Gly Leu Ser Ala
305                 310                 315                 320

Val Cys Ala Tyr Asn Leu Ser Thr Ala Glu Glu Val Phe Ser His Gly
                325                 330                 335

Lys Tyr Met Gln Ser Thr Thr Val Glu Gln Ser His Thr Lys Trp Val
            340                 345                 350

Arg Tyr Asn Gly Pro Val Pro Lys Pro Arg Pro Gly Ala Cys Ile Asp
        355                 360                 365

Ser Glu Ala Arg Ala Ala Asn Tyr Thr Ser Ser Leu Asn Leu Pro Asp
    370                 375                 380

Lys Thr Leu Gln Phe Val Lys Asp His Pro Leu Met Asp Asp Ser Val
385                 390                 395                 400

Thr Pro Ile Asp Asn Arg Pro Arg Leu Ile Lys Lys Asp Val Asn Tyr
                405                 410                 415

Thr Gln Ile Val Val Asp Arg Thr Gln Ala Leu Asp Gly Thr Val Tyr
            420                 425                 430

Asp Val Met Phe Val Ser Thr Asp Arg Gly Ala Leu His Lys Ala Ile
        435                 440                 445

Ser Leu Glu His Ala Val His Ile Ile Glu Glu Thr Gln Leu Phe Gln
    450                 455                 460

Asp Phe Glu Pro Val Gln Thr Leu Leu Leu Ser Ser Lys Lys Gly Asn
465                 470                 475                 480

Arg Phe Val Tyr Ala Gly Ser Asn Ser Gly Val Val Gln Ala Pro Leu
                485                 490                 495

Ala Phe Cys Gly Lys His Gly Thr Cys Glu Asp Cys Val Leu Ala Arg
            500                 505                 510

Asp Pro Tyr Cys Ala Trp Ser Pro Thr Ala Thr Cys Val Ala Leu
        515                 520                 525

His Gln Thr Glu Ser Pro Ser Arg Gly Leu Ile Gln Glu Met Ser Gly
    530                 535                 540

Asp Ala Ser Val Cys Pro Asp Lys Ser Lys Gly Ser Tyr Arg Gln His
545                 550                 555                 560

Phe Phe Lys His Gly Gly Thr Ala Glu Leu Lys Cys Ser Gln Lys Ser
                565                 570                 575

Asn Leu Ala Arg Val Phe Trp Lys Phe Gln Asn Gly Val Leu Lys Ala
            580                 585                 590

Glu Ser Pro Lys Tyr Gly Leu Met Gly Arg Lys Asn Leu Leu Ile Phe
        595                 600                 605

Asn Leu Ser Glu Gly Asp Ser Gly Val Tyr Gln Cys Leu Ser Glu Glu
    610                 615                 620
```

Arg Val Lys Asn Lys Thr Val Phe Gln Val Val Ala Lys His Val Leu
625                 630                 635                 640

Glu Val Lys Val Val Pro Lys Pro Val Val Ala Pro Thr Leu Ser Val
            645                 650                 655

Val Gln Thr Glu Gly Ser Arg Ile Ala Thr Lys Val Leu Val Ala Ser
        660                 665                 670

Thr Gln Gly Ser Ser Pro Pro Thr Pro Ala Val Gln Ala Thr Ser Ser
    675                 680                 685

Gly Ala Ile Thr Leu Pro Pro Lys Pro Ala Pro Thr Gly Thr Ser Cys
690                 695                 700

Glu Pro Lys Ile Val Ile Asn Thr Val Pro Gln Leu His Ser Glu Lys
705                 710                 715                 720

Thr Met Tyr Leu Lys Ser Ser Asp Thr Ser Thr Thr Asn Asp Thr Asp
            725                 730                 735

Lys Val Asp Tyr Glu Glu Tyr Ser Thr Glu Leu Ile Val Asn Thr Asp
        740                 745                 750

Ser Glu Ser Thr Ile Asp Ile Ile Leu Ser Gly Ser Thr His Ser Pro
    755                 760                 765

Glu Thr Ser Ser Lys Lys Pro Asp Tyr Ile Asp Asn Ser Asn Cys Ser
770                 775                 780

Ser Val Phe Glu Ile Ala Thr Pro Glu Pro Ile Thr Asp Asn Val Glu
785                 790                 795                 800

Asp His Thr Asp Thr Val Thr Tyr Thr Ser Asp Ser Ile Asn Thr Val
            805                 810                 815

Ser Ala Ser Ser Gly Glu Ser Thr Thr Asp Glu Thr Pro Glu Pro Ile
        820                 825                 830

Thr Asp Lys Glu Asp His Thr Val Thr Asp Thr Val Ser Tyr Thr Thr
    835                 840                 845

Val Ser Thr Ser Ser Gly Ile Val Thr Thr Lys Ser Thr Thr Asp Asp
850                 855                 860

Ala Asp Leu Tyr Asp Thr Tyr Asn Asp Asn Asp Thr Val Pro Pro Thr
865                 870                 875                 880

Thr Val Gly Gly Ser Thr Thr Ser Ile Ser Asn Tyr Lys Thr Lys Asp
            885                 890                 895

Phe Val Glu Ile Phe Gly Ile Thr Ala Leu Ile Ile Leu Ser Ala Val
        900                 905                 910

Ala Ile Phe Cys Ile Thr Tyr Tyr Ile Tyr Asn Lys Arg Ser Arg Lys
    915                 920                 925

Tyr Lys Thr Glu Asn Lys Val
930                 935

<210> SEQ ID NO 9
<211> LENGTH: 987
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

-continued

```
Phe Leu Thr Gly Ile Val Gly Asn Gly Leu Val Ile Leu Val Met Gly
    50                  55                  60
Tyr Gln Lys Lys Leu Arg Ser Met Thr Asp Lys Tyr Arg Leu His Leu
65                  70                  75                  80
Ser Val Ala Asp Leu Leu Phe Val Ile Thr Leu Pro Phe Trp Ala Val
                85                  90                  95
Asp Ala Val Ala Asn Trp Tyr Phe Gly Asn Phe Leu Cys Lys Ala Val
            100                 105                 110
His Val Ile Tyr Thr Val Asn Leu Tyr Ser Ser Val Leu Ile Leu Ala
        115                 120                 125
Phe Ile Ser Leu Asp Arg Tyr Leu Ala Ile Val His Ala Thr Asn Ser
    130                 135                 140
Gln Arg Pro Arg Lys Leu Leu Ala Glu Lys Val Val Tyr Val Gly Val
145                 150                 155                 160
Trp Ile Pro Ala Leu Leu Leu Thr Ile Pro Asp Phe Ile Phe Ala Asn
                165                 170                 175
Val Ser Glu Ala Asp Asp Arg Tyr Ile Cys Asp Arg Phe Tyr Pro Asn
            180                 185                 190
Asp Leu Trp Val Val Phe Gln Phe Gln His Ile Met Val Gly Leu
    195                 200                 205
Ile Leu Pro Gly Ile Val Ile Leu Ser Cys Tyr Cys Ile Ile Ser
    210                 215                 220
Lys Leu Ser His Ser Lys Gly His Gln Lys Arg Lys Ala Leu Lys Thr
225                 230                 235                 240
Thr Val Ile Leu Ile Leu Ala Phe Phe Ala Cys Trp Leu Pro Tyr Tyr
                245                 250                 255
Ile Gly Ile Ser Ile Asp Ser Phe Ile Leu Leu Glu Ile Ile Lys Gln
            260                 265                 270
Gly Cys Glu Phe Glu Asn Thr Val His Lys Trp Ile Ser Ile Thr Glu
        275                 280                 285
Ala Leu Ala Phe Phe His Cys Cys Leu Asn Pro Ile Leu Tyr Ala Phe
    290                 295                 300
Leu Gly Ala Lys Phe Lys Thr Ser Ala Gln His Ala Leu Thr Ser Val
305                 310                 315                 320
Ser Arg Gly Ser Ser Leu Lys Ile Leu Ser Lys Gly Lys Arg Gly Gly
                325                 330                 335
His Ser Ser Val Ser Thr Glu Ser Glu Ser Ser Phe His Ser Ser
            340                 345                 350
Val His His His His His His Gly Gly Gly Ser Gly Ser Leu Met
        355                 360                 365
Ser Lys Gly Glu Glu Leu Phe Thr Gly Val Val Pro Ile Leu Val Glu
370                 375                 380
Leu Asp Gly Asp Val Asn Gly His Lys Phe Ser Val Ser Gly Glu Gly
385                 390                 395                 400
Glu Gly Asp Ala Thr Tyr Gly Lys Leu Thr Leu Lys Phe Ile Cys Thr
                405                 410                 415
Thr Gly Lys Leu Pro Val Pro Trp Pro Thr Leu Val Thr Thr Leu Thr
            420                 425                 430
Tyr Gly Val Gln Cys Phe Ser Arg Tyr Pro Asp His Met Lys Arg His
        435                 440                 445
Asp Phe Phe Lys Ser Ala Met Pro Glu Gly Tyr Val Gln Glu Arg Thr
    450                 455                 460
```

-continued

```
Ile Ser Phe Lys Asp Asp Gly Asn Tyr Lys Thr Arg Ala Glu Val Lys
465                 470                 475                 480

Phe Glu Gly Asp Thr Leu Val Asn Arg Ile Glu Leu Lys Gly Ile Asp
                485                 490                 495

Phe Lys Glu Asp Gly Asn Ile Leu Gly His Lys Leu Glu Tyr Asn Tyr
                500                 505                 510

Asn Ser His Asn Val Tyr Ile Thr Ala Asp Lys Gln Lys Asn Gly Ile
            515                 520                 525

Lys Ala Asn Phe Lys Thr Arg His Asn Ile Glu Asp Gly Gly Val Gln
        530                 535                 540

Leu Ala Asp His Tyr Gln Gln Asn Thr Pro Ile Gly Asp Gly Pro Val
545                 550                 555                 560

Leu Leu Pro Asp Asn His Tyr Leu Ser Thr Gln Ser Ala Leu Ser Lys
                565                 570                 575

Asp Pro Asn Glu Lys Arg Asp His Met Val Leu Leu Glu Phe Val Thr
                580                 585                 590

Ala Ala Gly Ile Thr His Gly Met Asp Glu Leu Tyr Lys Gly Gly Ser
            595                 600                 605

Ser Gly Met Gly Asn Ile Phe Lys Pro Ile Pro Lys Ala Asp Tyr Gln
        610                 615                 620

Ile Val Glu Thr Val Pro Gln Ser Leu Thr Ala Ile Asn Ser Thr Asn
625                 630                 635                 640

Leu Ser Thr Tyr Glu Cys Phe Lys Arg Leu Ile Asp Leu Ala Lys Lys
                645                 650                 655

Glu Ile Tyr Ile Ala Thr Phe Cys Cys Asn Leu Ser Thr Asn Pro Glu
            660                 665                 670

Gly Thr Asp Ile Leu Asn Arg Leu Ile Asp Val Ser Ser Lys Val Ser
        675                 680                 685

Val Tyr Ile Leu Val Asp Glu Ser Ser Pro His Lys Asp Tyr Glu Lys
        690                 695                 700

Ile Lys Ser Ser His Ile Ser Tyr Ile Lys Val Asp Ile Gly Val Leu
705                 710                 715                 720

Asn Asn Glu Ser Val Gly Asn Leu Leu Gly Asn Phe Trp Val Val Asp
                725                 730                 735

Lys Leu His Phe Tyr Ile Gly Ser Ala Ser Leu Met Gly Asn Ala Leu
            740                 745                 750

Thr Thr Ile Lys Asn Met Gly Ile Tyr Ser Glu Asn Asn Ser Leu Ala
        755                 760                 765

Met Asp Leu Tyr Phe Arg Ser Leu Asp Tyr Lys Ile Ile Ser Lys Lys
770                 775                 780

Lys Cys Leu Phe Phe Thr Arg Met Ala Thr Lys Tyr His Phe Phe Lys
785                 790                 795                 800

Asn His Asn Gly Ile Phe Phe Ser Asp Ser Pro Glu His Met Val Gly
                805                 810                 815

Arg Lys Arg Thr Phe Asp Leu Asp Cys Val Ile His Tyr Ile Asp Ala
            820                 825                 830

Ala Lys Ser Thr Ile Asp Leu Ala Ile Val Ser Leu Leu Pro Thr Lys
        835                 840                 845

Arg Thr Lys Asp Ser Ile Val Tyr Trp Pro Ile Ile Lys Asp Ala Leu
        850                 855                 860

Ile Arg Ala Val Leu Glu Arg Gly Val Lys Leu Arg Val Leu Leu Gly
865                 870                 875                 880

Phe Trp Lys Lys Thr Asp Val Ile Ser Lys Ala Ser Ile Lys Ser Leu
```

```
                        885                 890                 895
Asn Glu Leu Gly Val Asp His Ile Asp Ile Ser Thr Lys Val Phe Arg
            900                 905                 910

Phe Pro Val Asn Ser Lys Val Asp Asp Ile Asn Asn Ser Lys Met Met
            915                 920                 925

Ile Ile Asp Gly Arg Tyr Ala His Val Met Thr Ala Asn Leu Asp Gly
            930                 935                 940

Ser His Phe Asn His His Ala Phe Val Ser Phe Asn Cys Met Asp Gln
945                 950                 955                 960

Gln Phe Thr Lys Lys Ile Ala Glu Val Phe Glu Arg Asp Trp Ile Ser
                965                 970                 975

Pro Tyr Ala Lys Glu Ile Asp Met Ser Gln Ile
            980                 985

<210> SEQ ID NO 10
<211> LENGTH: 694
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255
```

-continued

```
Lys Asn Glu Glu Asp Ile Glu Ile Ile Pro Ile Gln Glu Glu Glu
                260                 265                 270
Glu Glu Thr Glu Thr Asn Phe Pro Pro Gln Asp Gln Glu Ser
            275                 280                 285
Ser Pro Ile Glu Asn Asp Ser Ser Pro Val His His His His His
        290                 295                 300
Gly Gly Gly Gly Ser Gly Ser Leu Gly Gly Ser Ser Gly Met Gly Asn
305                 310                 315                 320
Ile Phe Lys Pro Ile Pro Lys Ala Asp Tyr Gln Ile Val Glu Thr Val
                325                 330                 335
Pro Gln Ser Leu Thr Ala Ile Asn Ser Thr Asn Leu Ser Thr Tyr Glu
            340                 345                 350
Cys Phe Lys Arg Leu Ile Asp Leu Ala Lys Lys Glu Ile Tyr Ile Ala
        355                 360                 365
Thr Phe Cys Cys Asn Leu Ser Thr Asn Pro Glu Gly Thr Asp Ile Leu
    370                 375                 380
Asn Arg Leu Ile Asp Val Ser Ser Lys Val Ser Val Tyr Ile Leu Val
385                 390                 395                 400
Asp Glu Ser Ser Pro His Lys Asp Tyr Glu Lys Ile Lys Ser His
                405                 410                 415
Ile Ser Tyr Ile Lys Val Asp Ile Gly Val Leu Asn Asn Glu Ser Val
            420                 425                 430
Gly Asn Leu Leu Gly Asn Phe Trp Val Val Asp Lys Leu His Phe Tyr
        435                 440                 445
Ile Gly Ser Ala Ser Leu Met Gly Asn Ala Leu Thr Thr Ile Lys Asn
    450                 455                 460
Met Gly Ile Tyr Ser Glu Asn Asn Ser Leu Ala Met Asp Leu Tyr Phe
465                 470                 475                 480
Arg Ser Leu Asp Tyr Lys Ile Ile Ser Lys Lys Lys Cys Leu Phe Phe
                485                 490                 495
Thr Arg Met Ala Thr Lys Tyr His Phe Phe Lys Asn His Asn Gly Ile
            500                 505                 510
Phe Phe Ser Asp Ser Pro Glu His Met Val Gly Arg Lys Arg Thr Phe
        515                 520                 525
Asp Leu Asp Cys Val Ile His Tyr Ile Asp Ala Ala Lys Ser Thr Ile
    530                 535                 540
Asp Leu Ala Ile Val Ser Leu Leu Pro Thr Lys Arg Thr Lys Asp Ser
545                 550                 555                 560
Ile Val Tyr Trp Pro Ile Ile Lys Asp Ala Leu Ile Arg Ala Val Leu
                565                 570                 575
Glu Arg Gly Val Lys Leu Arg Val Leu Leu Gly Phe Trp Lys Lys Thr
            580                 585                 590
Asp Val Ile Ser Lys Ala Ser Ile Lys Ser Leu Asn Glu Leu Gly Val
        595                 600                 605
Asp His Ile Asp Ile Ser Thr Lys Val Phe Arg Phe Pro Val Asn Ser
    610                 615                 620
Lys Val Asp Asp Ile Asn Asn Ser Lys Met Met Ile Ile Asp Gly Arg
625                 630                 635                 640
Tyr Ala His Val Met Thr Ala Asn Leu Asp Gly Ser His Phe Asn His
                645                 650                 655
His Ala Phe Val Ser Phe Asn Cys Met Asp Gln Gln Phe Thr Lys Lys
            660                 665                 670
Ile Ala Glu Val Phe Glu Arg Asp Trp Ile Ser Pro Tyr Ala Lys Glu
```

```
                    675                 680                 685

Ile Asp Met Ser Gln Ile
            690

<210> SEQ ID NO 11
<211> LENGTH: 907
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Asp Ile Lys Asp Ser Lys Val Lys Arg Phe Cys Ser Lys Asn
1               5                   10                  15

Ile Leu Ile Ile Leu Gly Phe Thr Ser Ile Leu Ala Val Ile Ala Leu
            20                  25                  30

Ile Ala Val Gly Leu Thr Gln Asn Lys Pro Leu Pro Glu Asn Val Lys
        35                  40                  45

Tyr Gly Ile Val Leu Asp Ala Gly Ser Ser His Thr Asn Leu Tyr Ile
    50                  55                  60

Tyr Lys Trp Pro Ala Glu Lys Glu Asn Asp Thr Gly Val Val Gln Gln
65                  70                  75                  80

Leu Glu Glu Cys Gln Val Lys Gly Pro Gly Ile Ser Lys Tyr Ala Gln
                85                  90                  95

Lys Thr Asp Glu Ile Gly Ala Tyr Leu Ala Glu Cys Met Glu Leu Ser
            100                 105                 110

Thr Glu Leu Ile Pro Thr Ser Lys His His Gln Thr Pro Val Tyr Leu
        115                 120                 125

Gly Ala Thr Ala Gly Met Arg Leu Leu Arg Met Glu Ser Glu Gln Ser
    130                 135                 140

Ala Asp Glu Val Leu Ala Ala Val Ser Thr Ser Leu Lys Ser Tyr Pro
145                 150                 155                 160

Phe Asp Phe Gln Gly Ala Lys Ile Ile Thr Gly Gln Glu Glu Gly Ala
                165                 170                 175

Tyr Gly Trp Ile Thr Ile Asn Tyr Leu Leu Gly Arg Phe Thr Gln Glu
            180                 185                 190

Gln Ser Trp Leu Ser Leu Ile Ser Asp Ser Gln Lys Gln Glu Thr Phe
        195                 200                 205

Gly Ala Leu Asp Leu Gly Gly Ala Ser Thr Gln Ile Thr Phe Val Pro
    210                 215                 220

Gln Asn Ser Thr Ile Glu Ser Pro Glu Asn Ser Leu Gln Phe Arg Leu
225                 230                 235                 240

Tyr Gly Glu Asp Tyr Thr Val Tyr Thr His Ser Phe Leu Cys Tyr Gly
                245                 250                 255

Lys Asp Gln Ala Leu Trp Gln Lys Leu Ala Lys Asp Ile Gln Val Ser
            260                 265                 270

Ser Gly Gly Val Leu Lys Asp Pro Cys Phe Asn Pro Gly Tyr Glu Lys
        275                 280                 285

Val Val Asn Val Ser Glu Leu Tyr Gly Thr Pro Cys Thr Lys Arg Phe
    290                 295                 300

Glu Lys Lys Leu Pro Phe Asp Gln Phe Arg Ile Gln Gly Thr Gly Asp
305                 310                 315                 320

Tyr Glu Gln Cys His Gln Ser Ile Leu Glu Leu Phe Asn Asn Ser His
                325                 330                 335
```

```
Cys Pro Tyr Ser Gln Cys Ala Phe Asn Gly Val Phe Leu Pro Pro Leu
                340                 345                 350

His Gly Ser Phe Gly Ala Phe Ser Ala Phe Tyr Phe Val Met Asp Phe
            355                 360                 365

Phe Lys Lys Val Ala Lys Asn Ser Val Ile Ser Gln Glu Lys Met Thr
        370                 375                 380

Glu Ile Thr Lys Asn Phe Cys Ser Lys Ser Trp Glu Glu Thr Lys Thr
385                 390                 395                 400

Ser Tyr Pro Ser Val Lys Glu Lys Tyr Leu Ser Glu Tyr Cys Phe Ser
                405                 410                 415

Gly Ala Tyr Ile Leu Ser Leu Leu Gln Gly Tyr Asn Phe Thr Asp Ser
            420                 425                 430

Ser Trp Glu Gln Ile His Phe Met Gly Lys Ile Lys Asp Ser Asn Ala
        435                 440                 445

Gly Trp Thr Leu Gly Tyr Met Leu Asn Leu Thr Asn Met Ile Pro Ala
450                 455                 460

Glu Gln Pro Leu Ser Pro Pro Leu Pro His Ser Thr Tyr Ile Gly Leu
465                 470                 475                 480

Met Val Leu Phe Ser Leu Leu Leu Val Ala Val Ala Ile Thr Gly Leu
                485                 490                 495

Phe Ile Tyr Ser Lys Pro Ser Tyr Phe Trp Lys Glu Ala Val Val His
            500                 505                 510

His His His His His Gly Gly Gly Ser Gly Ser Leu Gly Gly Ser
        515                 520                 525

Ser Gly Met Gly Asn Ile Phe Lys Pro Ile Pro Lys Ala Asp Tyr Gln
530                 535                 540

Ile Val Glu Thr Val Pro Gln Ser Leu Thr Ala Ile Asn Ser Thr Asn
545                 550                 555                 560

Leu Ser Thr Tyr Glu Cys Phe Lys Arg Leu Ile Asp Leu Ala Lys Lys
                565                 570                 575

Glu Ile Tyr Ile Ala Thr Phe Cys Cys Asn Leu Ser Thr Asn Pro Glu
            580                 585                 590

Gly Thr Asp Ile Leu Asn Arg Leu Ile Asp Val Ser Ser Lys Val Ser
        595                 600                 605

Val Tyr Ile Leu Val Asp Glu Ser Ser Pro His Lys Asp Tyr Glu Lys
610                 615                 620

Ile Lys Ser Ser His Ile Ser Tyr Ile Lys Val Asp Ile Gly Val Leu
625                 630                 635                 640

Asn Asn Glu Ser Val Gly Asn Leu Leu Gly Asn Phe Trp Val Val Asp
                645                 650                 655

Lys Leu His Phe Tyr Ile Gly Ser Ala Ser Leu Met Gly Asn Ala Leu
            660                 665                 670

Thr Thr Ile Lys Asn Met Gly Ile Tyr Ser Glu Asn Asn Ser Leu Ala
        675                 680                 685

Met Asp Leu Tyr Phe Arg Ser Leu Asp Tyr Lys Ile Ile Ser Lys Lys
690                 695                 700

Lys Cys Leu Phe Phe Thr Arg Met Ala Thr Lys Tyr His Phe Phe Lys
705                 710                 715                 720

Asn His Asn Gly Ile Phe Phe Ser Asp Ser Pro Glu His Met Val Gly
                725                 730                 735

Arg Lys Arg Thr Phe Asp Leu Asp Cys Val Ile His Tyr Ile Asp Ala
            740                 745                 750

Ala Lys Ser Thr Ile Asp Leu Ala Ile Val Ser Leu Leu Pro Thr Lys
```

```
                    755                 760                 765
Arg Thr Lys Asp Ser Ile Val Tyr Trp Pro Ile Ile Lys Asp Ala Leu
    770                 775                 780

Ile Arg Ala Val Leu Glu Arg Gly Val Lys Leu Arg Val Leu Leu Gly
785                 790                 795                 800

Phe Trp Lys Lys Thr Asp Val Ile Ser Lys Ala Ser Ile Lys Ser Leu
                805                 810                 815

Asn Glu Leu Gly Val Asp His Ile Asp Ile Ser Thr Lys Val Phe Arg
            820                 825                 830

Phe Pro Val Asn Ser Lys Val Asp Asp Ile Asn Asn Ser Lys Met Met
        835                 840                 845

Ile Ile Asp Gly Arg Tyr Ala His Val Met Thr Ala Asn Leu Asp Gly
    850                 855                 860

Ser His Phe Asn His His Ala Phe Val Ser Phe Asn Cys Met Asp Gln
865                 870                 875                 880

Gln Phe Thr Lys Lys Ile Ala Glu Val Phe Glu Arg Asp Trp Ile Ser
                885                 890                 895

Pro Tyr Ala Lys Glu Ile Asp Met Ser Gln Ile
            900                 905

<210> SEQ ID NO 12
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gly Trp Ser Cys Ile Ile Leu Phe Leu Val Ala Thr Ala Thr Gly
1               5                   10                  15

Ala His Ser Phe Gly Asp Glu Glu Arg Arg Cys Asp Pro Ile Arg
            20                  25                  30

Ile Ser Met Cys Gln Asn Leu Gly Tyr Asn Val Thr Lys Met Pro Asn
            35                  40                  45

Leu Val Gly His Glu Leu Gln Thr Asp Ala Glu Leu Gln Leu Thr Thr
        50                  55                  60

Phe Thr Pro Leu Ile Gln Tyr Gly Cys Ser Ser Gln Leu Gln Phe Phe
65                  70                  75                  80

Leu Cys Ser Val Tyr Val Pro Met Cys Thr Glu Lys Ile Asn Ile Pro
                85                  90                  95

Ile Gly Pro Cys Gly Gly Met Cys Leu Ser Val Lys Arg Arg Cys Glu
            100                 105                 110

Pro Val Leu Lys Glu Phe Gly Phe Ala Trp Pro Glu Ser Leu Asn Cys
        115                 120                 125

Ser Lys Phe Pro Pro Gln Asn Asp His Asn His Met Cys Met Glu Gly
130                 135                 140

Pro Gly Asp Glu Glu Val Pro Leu Pro His Lys Thr Pro Ile Gln Pro
145                 150                 155                 160

Gly Glu Glu Thr Ser Thr Thr Asn Asp Thr Asp Lys Val Asp Tyr Glu
                165                 170                 175

Glu Tyr Ser Thr Glu Leu Ile Val Asn Thr Asp Ser Glu Ser Thr Ile
            180                 185                 190

Asp Ile Ile Leu Ser Gly Ser Thr His Ser Pro Glu Thr Ser Ser Lys
        195                 200                 205
```

-continued

```
Lys Pro Asp Tyr Ile Asp Asn Ser Asn Cys Ser Ser Val Phe Glu Ile
    210                 215                 220
Ala Thr Pro Glu Pro Ile Thr Asp Asn Val Glu Asp His Thr Asp Thr
225                 230                 235                 240
Val Thr Tyr Thr Ser Asp Ser Ile Asn Thr Val Ser Ala Ser Ser Gly
                245                 250                 255
Glu Ser Thr Thr Asp Glu Thr Pro Glu Pro Ile Thr Asp Lys Glu Asp
            260                 265                 270
His Thr Val Thr Asp Thr Val Ser Tyr Thr Thr Val Ser Thr Ser Ser
        275                 280                 285
Gly Ile Val Thr Thr Lys Ser Thr Thr Asp Asp Ala Asp Leu Tyr Asp
    290                 295                 300
Thr Tyr Asn Asp Asn Asp Thr Val Pro Pro Thr Thr Val Gly Gly Ser
305                 310                 315                 320
Thr Thr Ser Ile Ser Asn Tyr Lys Thr Lys Asp Phe Val Glu Ile Phe
                325                 330                 335
Gly Ile Thr Ala Leu Ile Ile Leu Ser Ala Val Ala Ile Phe Cys Ile
            340                 345                 350
Thr Tyr Tyr Ile Tyr Asn Lys Arg Ser Arg Lys Tyr Lys Thr Glu Asn
        355                 360                 365
Lys Val
    370

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggaatttgc cctttttgag                                              20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagtagtcct tgaccaggca gcc                                          23

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5

<210> SEQ ID NO 16
<211> LENGTH: 372
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Ser, Lys, or Pro

<400> SEQUENCE: 16

Met Trp Pro Phe Ala Xaa Val Pro Ala Gly Ala Lys Cys Arg Leu Val
1               5                   10                  15

Glu Thr Leu Pro Glu Asn Met Asp Phe Arg Ser Asp His Leu Thr Thr
            20                  25                  30

Phe Glu Cys Phe Asn Glu Ile Ile Thr Leu Ala Lys Lys Tyr Ile Tyr
        35                  40                  45

Ile Ala Ser Phe Cys Cys Asn Pro Leu Ser Thr Thr Arg Gly Ala Leu
    50                  55                  60

Ile Phe Asp Lys Leu Lys Glu Ala Ser Glu Lys Gly Ile Lys Ile Ile
65                  70                  75                  80

Val Leu Leu Asp Glu Arg Gly Lys Arg Asn Leu Gly Glu Leu Gln Ser
                85                  90                  95

His Cys Pro Asp Ile Asn Phe Ile Thr Val Asn Ile Asp Lys Lys Asn
            100                 105                 110

Asn Val Gly Leu Leu Leu Gly Cys Phe Trp Val Ser Asp Asp Glu Arg
        115                 120                 125

Cys Tyr Val Gly Asn Ala Ser Phe Thr Gly Gly Ser Ile His Thr Ile
    130                 135                 140

Lys Thr Leu Gly Val Tyr Ser Asp Tyr Pro Pro Leu Ala Thr Asp Leu
145                 150                 155                 160

Arg Arg Arg Phe Asp Thr Phe Lys Ala Phe Asn Ser Ala Lys Asn Ser
                165                 170                 175

Trp Leu Asn Leu Cys Ser Ala Ala Cys Cys Leu Pro Val Ser Thr Ala
            180                 185                 190

Tyr His Ile Lys Asn Pro Ile Gly Gly Val Phe Phe Thr Asp Ser Pro
        195                 200                 205

Glu His Leu Leu Gly Tyr Ser Arg Asp Leu Asp Thr Asp Val Val Ile
    210                 215                 220

Asp Lys Leu Lys Ser Ala Lys Thr Ser Ile Asp Ile Glu His Leu Ala
225                 230                 235                 240

Ile Val Pro Thr Thr Arg Val Asp Gly Asn Ser Tyr Tyr Trp Pro Asp
                245                 250                 255

Ile Tyr Asn Ser Ile Ile Glu Ala Ala Ile Asn Arg Gly Val Lys Ile
            260                 265                 270

Arg Leu Leu Val Gly Asn Trp Asp Lys Asn Asp Val Tyr Ser Met Ala
        275                 280                 285

Thr Ala Arg Ser Leu Asp Ala Leu Cys Val Gln Asn Asp Leu Ser Val
    290                 295                 300

Lys Val Phe Thr Ile Gln Asn Asn Thr Lys Leu Leu Ile Val Asp Asp
305                 310                 315                 320

Glu Tyr Val His Ile Thr Ser Ala Asn Phe Asp Gly Thr His Tyr Gln
                325                 330                 335

Asn His Gly Phe Val Ser Phe Asn Ser Ile Asp Lys Gln Leu Val Ser
            340                 345                 350

```
Glu Ala Lys Lys Ile Phe Glu Arg Asp Trp Val Ser Ser His Ser Lys
            355                 360                 365
Ser Leu Lys Ile
    370
```

INTEGRAL MEMBRANE PROTEIN DISPLAY ON POXVIRUS EXTRACELLULAR ENVELOPED VIRIONS

CROSS REFERENCE TO RELATED APPLICATIONS

This is a non-provisional of pending U.S. provisional application Ser. No. 63/020,818, filed May 6, 2020, the entirety of which application is incorporated by reference herein.

SEQUENCE LISTING

The instant application contains a Sequence Listing which has been submitted electronically in ASCII format and is hereby incorporated by reference in its entirety. Said ASCII copy, created on Apr. 30, 2021, is named 8555_037_SL.txt and is 74,144 bytes in size.

BACKGROUND

Antibodies of defined specificity are being employed in an increasing number of diverse therapeutic applications. A number of methods have been used to obtain useful antibodies for human therapeutic use. These include chimeric and humanized antibodies, and fully human antibodies selected from libraries, e.g., phage display libraries, or from transgenic animals. Immunoglobulin libraries constructed in bacteriophage can derive from antibody producing cells of naïve or specifically immunized individuals and could, in principle, include new and diverse pairings of human immunoglobulin heavy and light chains. Although this strategy does not suffer from an intrinsic repertoire limitation, it requires that complementarity determining regions (CDRs) of the expressed immunoglobulin fragment be synthesized and fold properly in bacterial cells. Many antigen binding regions, however, are difficult to assemble correctly as a fusion protein in bacterial cells. In addition, the protein will not undergo normal eukaryotic post-translational modifications. As a result, this method imposes a different selective filter on the antibody specificities that can be obtained. Alternatively, fully human antibodies can be isolated from libraries in eukaryotic systems, e.g., yeast display, retroviral display, or expression in DNA viruses such as poxviruses. See, e.g., U.S. Pat. No. 7,858,559, and U.S. Patent Appl. Publication No. 2013-028892, which are incorporated herein by reference in their entireties.

Many important targets for therapeutic antibodies are integral membrane proteins (IMPs), e.g., multi-pass membrane proteins (GPCRs, Ion Channels, etc.) that are difficult to express and purify in a conformationally-intact state. The absence of properly folded target proteins in an isolated state makes the identification and selection of antibodies to these targets challenging. While certain IMPs can be expressed on the surface of cells, e.g., mammalian cells, whole cells are problematic for use in antibody discovery because they are complex antigen mixtures, target expression can be low, and because certain display packages used to construct antibody libraries (e.g., vaccinia virus antibody libraries) can bind to whole cells non-specifically. There remains a need for new methods to express and display target IMPs of interest in their native conformation at a sufficient concentration and with minimal competition from other cell proteins to allow for identification and selection of therapeutic antibodies and antibody-like molecules from display libraries and from animal-based systems.

SUMMARY

This disclosure provides compositions and methods for expressing and displaying isolated integral membrane proteins (IMPs) or fragments thereof in a native conformation for use in the screening, selecting, and identifying of antibodies or antibody-like molecules that bind to a target IMP of interest.

In certain embodiments, the disclosure provides an isolated polynucleotide that includes: a first nucleic acid fragment that encodes an integral membrane protein (IMP) or fragment thereof, where the IMP or fragment thereof includes at least one extra-membrane region, at least one transmembrane domain and at least one intra-membrane region, and where a portion of the first nucleic acid fragment encoding at least one intra-membrane region is situated at the 5' or 3' end of the first nucleic acid fragment; and a second nucleic acid fragment that encodes a fowlpox virus FPV108 protein or functional fragment thereof or a rabbit pox virus RBXV041 protein of functional fragment thereof, where the second nucleic acid fragment is fused in frame to a portion of the first nucleic acid fragment that encodes an intra-membrane region of the IMP. According to these embodiments, a poxvirus infected cell containing the polynucleotide can express an IMP-FPV108 or IMP-RBXV041 fusion protein as part of the outer envelope membrane of an extracellular enveloped virion (EEV). In certain aspects the IMP is a multi-pass membrane protein comprising at least two, at least three, at least four, at least five, at least six or at least seven transmembrane domains. In certain aspects the IMP is a multi-pass membrane protein listed in Table 1.

In certain aspects the multi-pass IMP can have an odd number of transmembrane domains, the 5' end of the first nucleic acid fragment can encode an extra-membrane region, and the 3' end of the first nucleic acid fragment can encode an intra-membrane region fused to the 5' end of the second nucleic acid fragment. In certain aspects the first nucleic acid fragment of this type can encode, e.g., a G-protein coupled receptor (GPCR). In certain aspects the GPCR can be the human frizzled-4 protein (FZD4), or a fragment thereof, and the polynucleotide can encode a polypeptide that includes amino acids 20 to 892 of SEQ ID NO: 2. In certain aspects the polypeptide can further include a signal peptide, e.g., amino acids 1 to 19 of SEQ ID NO: 2. In certain aspects the GPCR can be a CXC chemokine receptor, e.g., CXCR4, or a fragment thereof, and the polynucleotide can encode a polypeptide that includes the amino acid sequence SEQ ID NO: 3.

In certain aspects the multi-pass IMP can have an even number of transmembrane domains, and both the 5' and 3' ends of the first nucleic acid fragment can encode intra-membrane regions. In certain aspects, the second nucleic acid fragment can be fused to 3' end of the first nucleic acid fragment. In certain aspects the IMP can be, e.g., human CD20 protein, or CD39 or a fragment thereof.

In certain aspects, the first and second nucleic acid fragments of a polynucleotide provided herein can be directly fused. In certain aspects the polynucleotide as provided herein can include a third nucleic acid fragment encoding a heterologous peptide, e.g., a linker sequence, an amino acid tag or label, or a peptide or polypeptide sequence that facilitates purification, such as a histidine tag. In certain aspects a polynucleotide as provided here can be operably associated with a poxvirus promoter, e.g., a p7.5, a T7, or H5 promoter.

The disclosure further provides an FPV108 or RBXV041 fusion protein encoded by a polynucleotide as provided herein. The disclosure further provides a poxvirus genome, e.g., a fowlpox virus genome or rabbit pox virus genome, that includes a polynucleotide as provided herein. The disclosure further provides a recombinant fowlpox virus EEV that includes a poxvirus genome as provided herein and a recombinant rabbit pox virus EEV that includes a poxvirus genome as provided herein.

The disclosure further provides a method of producing a recombinant pox virus EEV, such as a fowlpox virus EEV as provided herein where the method includes infecting a host cell permissive for fowlpox virus infectivity with a fowlpox virus comprising a poxvirus genome as provided herein, and recovering EEV released from the host cell. Similarly, the disclosure provides a method of producing a recombinant rabbit pox virus EEV as provided herein where the method includes infecting a host cell permissive for rabbit pox virus infectivity with a rabbit pox virus comprising a poxvirus genome as provided herein, and recovering EEV released from the host cell.

The disclosure further provides a method to display an integral membrane protein (IMP) or fragment thereof in a native conformation where the method includes infecting host cells permissive for poxvirus infectivity with a recombinant poxvirus that expresses an IMP or fragment thereof as a fusion protein with poxvirus EEV-specific protein or membrane-associated fragment thereof, where EEV produced by the infected host cell comprise the IMP fusion protein as part of the EEV outer envelope membrane and recovering EEV released from the host cell. In certain aspects the IMP or fragment thereof displays on the surface of the EEV in a native conformation. In certain aspects the EEV-specific protein can be the fowlpox virus FPV018 protein or the rabbit pox virus RBXV041 protein, any membrane-associated fragment thereof, or any combination thereof.

In certain aspects the EEV-specific protein is F13L (SEQ ID NO: 1) or a functional fragment thereof. In certain aspects the EEV-specific protein is FPV108 (SEQ ID NO: 2) or RBXV041 (SEQ ID NO:3). In certain aspects the IMP is a multi-pass membrane protein that includes at least two, at least three, at least four, at least five, at least six or at least seven transmembrane domains. In certain aspects the IMP can be a G-protein coupled receptor (GPCR), e.g., human FZD4 or CXCR4 as described above, that includes seven transmembrane domains, and the F13L, FPV108, or RBXV041 protein can be fused to the C-terminus of the IMP. In certain aspects the IMP or fragment thereof can have an even number of transmembrane domains, e.g., human CD20 or CD39 as described above, where both the N-terminus and the C-terminus of the IMP or fragment thereof are intra-membrane, and the membrane-associated EEV-specific protein, e.g., FPV108 or RBXV041 can be fused to the N-terminus or the C-terminus of the IMP.

In certain aspects the membrane-associated EEV specific protein fragment can include or consist of the stalk, transmembrane, and intra-membrane domains of the vaccinia virus A56R protein, e.g., amino acids 108 to 314 of SEQ ID NO: 5.

A fusion protein as provided, when expressed by a recombinant poxvirus, e.g., a vaccinia virus, fowlpox virus, or rabbit pox virus can appear on the surface of the poxvirus extracellular enveloped virion (EEV) in a native conformation. A recombinant poxvirus EEV comprising the fusion protein is also provided. The disclosure further provides a recombinant poxvirus EEV that includes a heterologous IMP or fragment thereof fused to a poxvirus EEV-specific protein or membrane-associated fragment thereof, where the fusion protein is situated in the EEV outer envelope membrane, and where the IMP or fragment thereof displays on the surface of the EEV in its native conformation. In certain aspects the recombinant poxvirus EEV is a fowlpox virus or rabbit pox virus EEV.

The disclosure also provides a method to select antibodies that bind to a multi-pass membrane protein (IMP) comprising: (a) providing a first and second recombinant poxvirus EEV as described herein, wherein the first and second recombinant poxvirus EEV are each generated in a different recombinant poxvirus; (b) immunizing a mammal with the first recombinant poxvirus; (c) contacting a display library that that comprises display packages displaying a plurality of antigen binding domains with the second recombinant poxvirus such that the display packages displaying antigen binding domains that specifically bind to the IMP expressed on the EEV can bind thereto, wherein said display library is generated from B cells isolated from the immunized mammal; (d) removing unbound display packages; and (e) recovering display packages that display an antigen binding domain specific for the IMP expressed on the second recombinant EEV.

BRIEF DESCRIPTION OF THE DRAWINGS/FIGURES

FIG. 1A-D: Diagrammatic depiction of integral membrane proteins (IMPs) or fragment thereof fused to fowlpox virus extracellular enveloped virion (EEV)-specific proteins or fragments thereof. The parallel horizontal lines are a diagram of the EEV outer membrane. "6×His" is disclosed as SEQ ID NO: 15.

FIG. 1A-1D diagrams the extracellular domain (ECD) of an IMP fused to a fragment of the vaccinia A56R protein that includes the transmembrane domain and the intra-membrane domain. FIG. 1B diagrams the topology of a typical G protein-coupled receptor fused to the fowlpox virus EEV-specific protein FPV108. The FPV108 as well as the RBXV041 protein are associated with the inner side of the EEV outer membrane. FIG. 1C diagrams the topology of an IMP with an even number of transmembrane domains, e.g., CD20, fused to FPV108. FIG. 1D diagrams the topology of an ion channel fused to the fowlpox virus EEV-specific protein FPV108.

Figure 2:
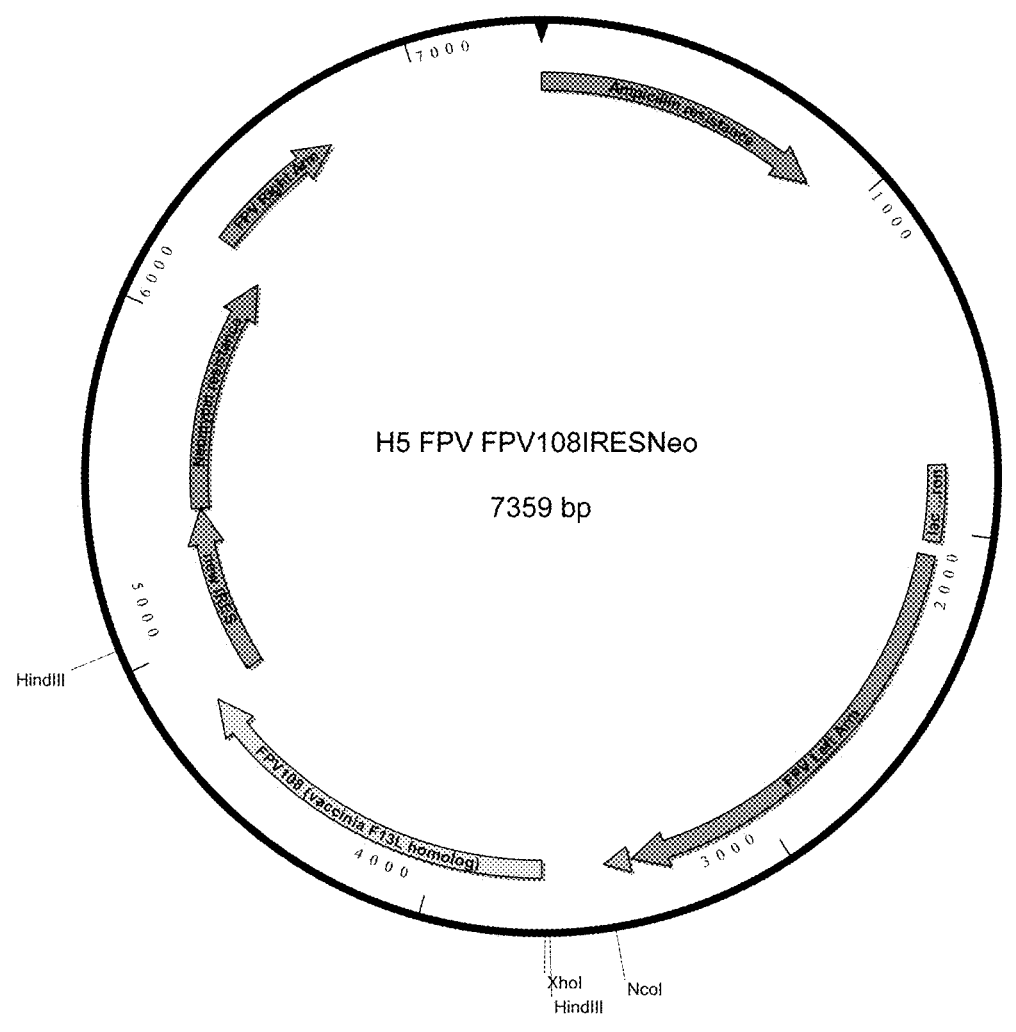

FIG. 2: Diagrammatic depiction of a fowlpox vector used herein.

Figure 3:
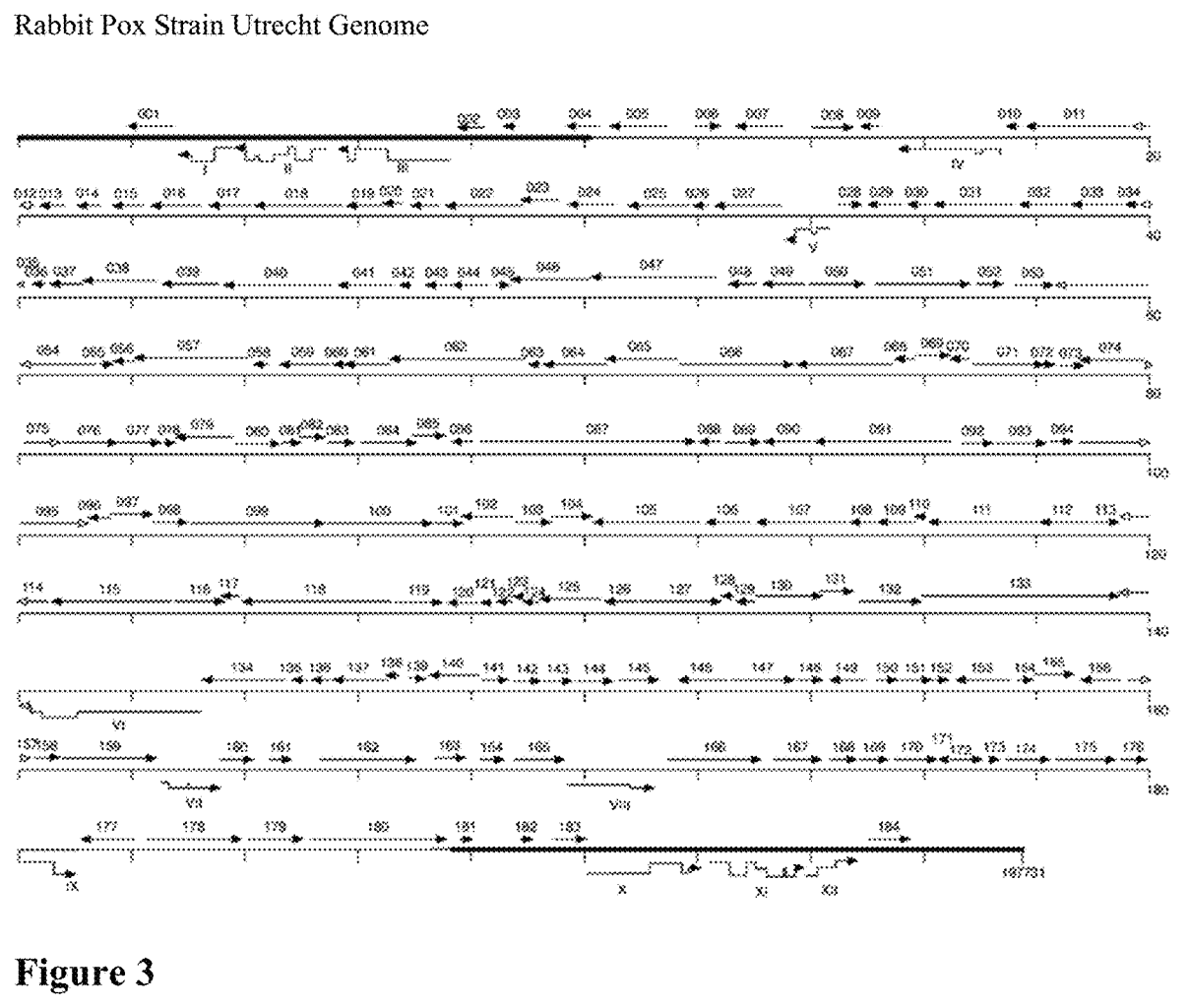

FIG. 3: Depiction of the rabbit pox coding regions.

Figure 4:
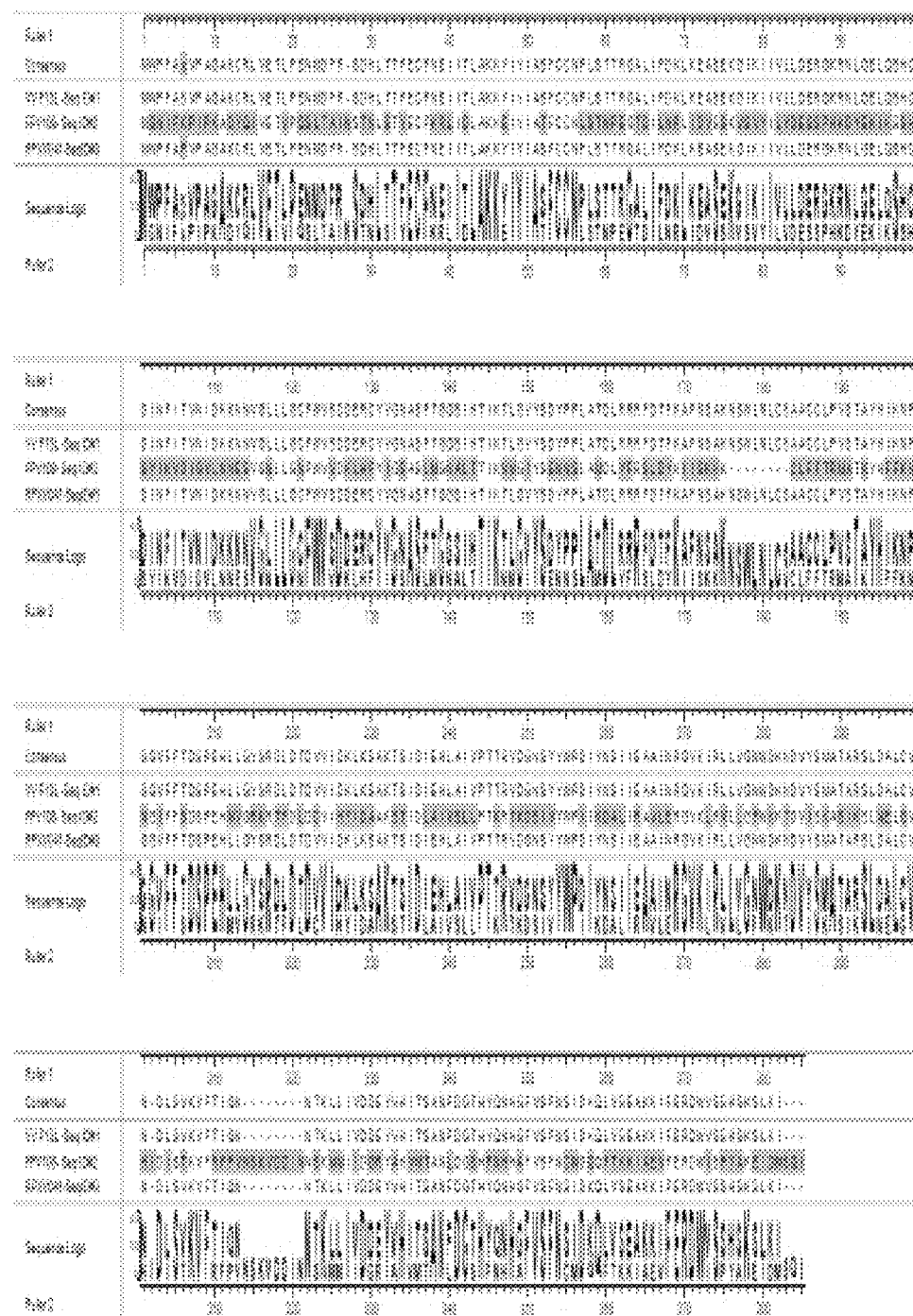

FIG. 4: Alignment of VVF13L, FPV108, and RBXV041 sequences (SEQ ID NOS 16 and 1-3, respectively, in order of appearance).

FIG. 5: Percent identity between VVF13L, FPV108, and RBXV041.

Figure 6:
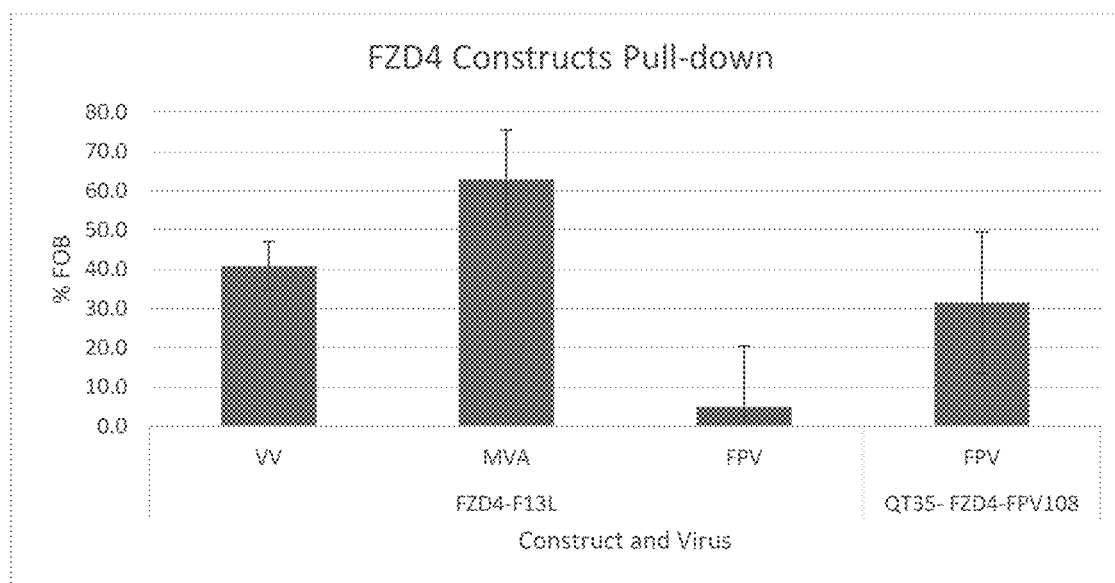

FIG. 6: Pulldown of various viruses: VV/FZD4-F13L, MVA/FZD4-F13L, FPV/FZD4-F13L and FPV/FZD4-FPV108 using an anti-FZD4 antibody coupled to ProG beads followed by plaque assay to titer. Data shows % of each virus pulled down with anti-FZD4 antibody after subtracting the amount pulled down with a control antibody.

Figure 7:
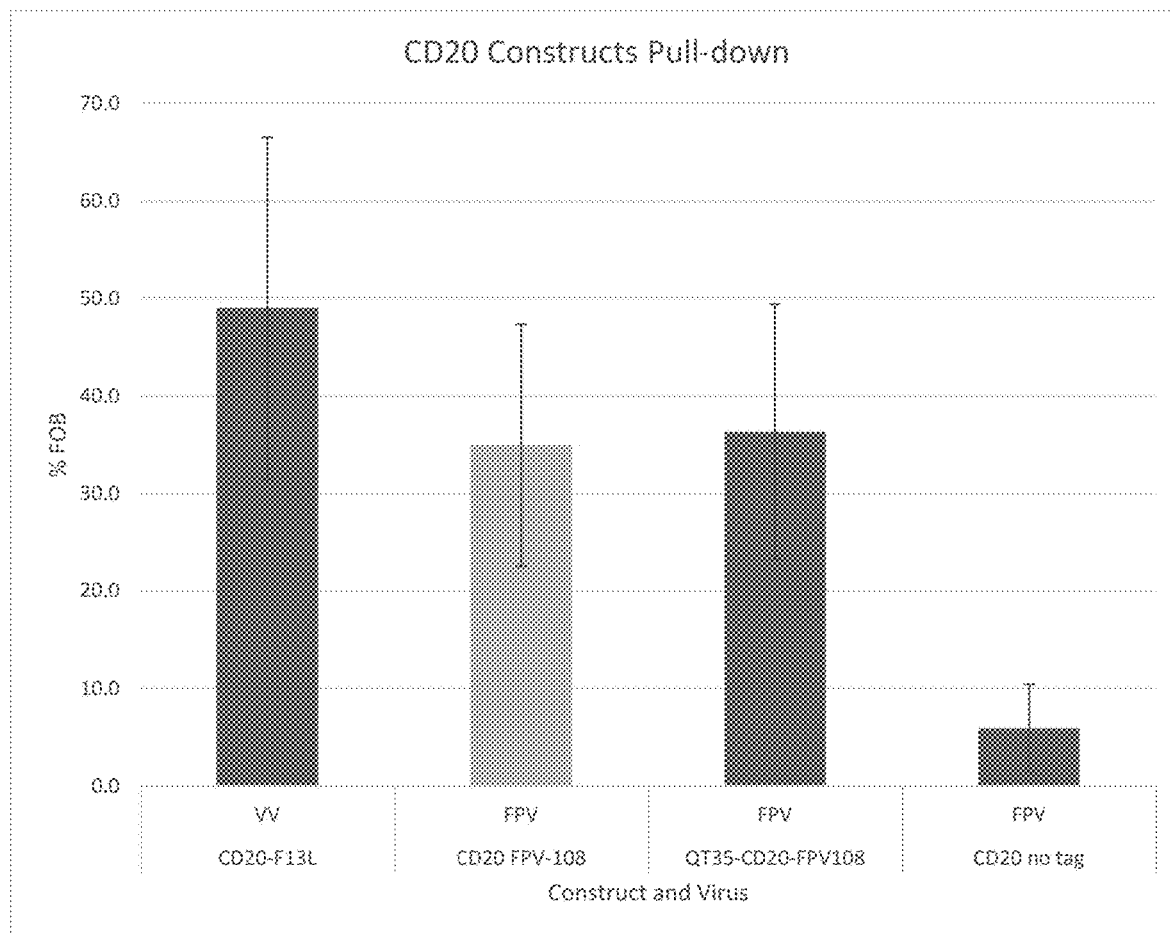

FIG. 7: Pulldown of various viruses: VV/CD20-F13, FPV/CD20-FPV108 and FPV/CD20 (no tag) as well as FPV generated by pseudotyping by infecting QT35/CD20-FPV108 expressing cells with wild type FPV. Pull down was carried out using an anti-CD20 antibody coupled to ProG beads followed by plaque assay to titer. Data shows % of each virus pulled down with anti-CD20 antibody after subtracting the amount pulled down with a control antibody.

Figure 8:
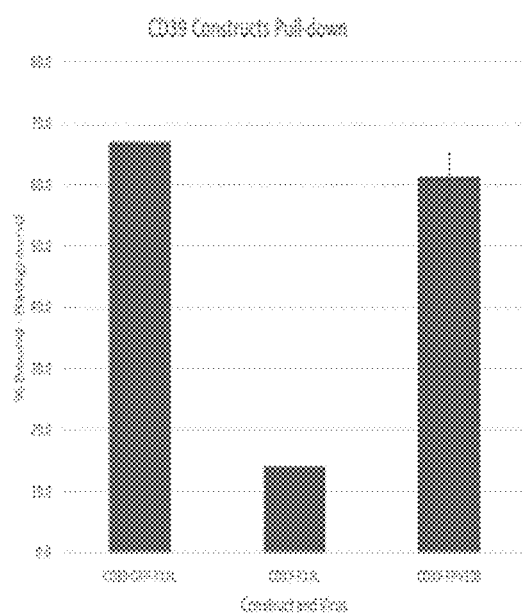
Figure 10A:
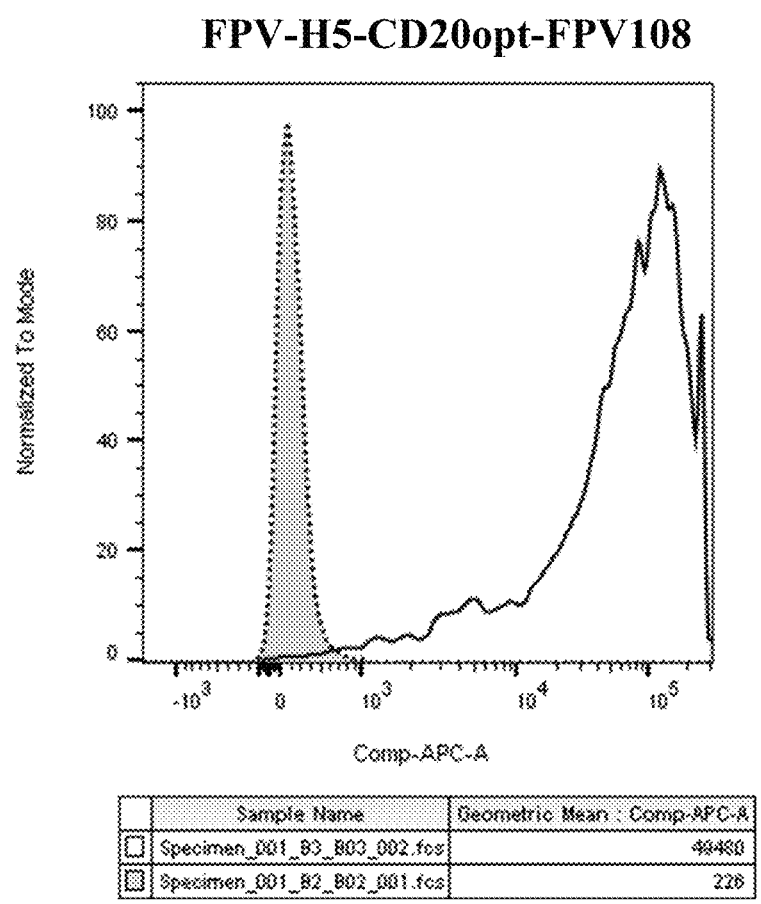
Figure 10B:
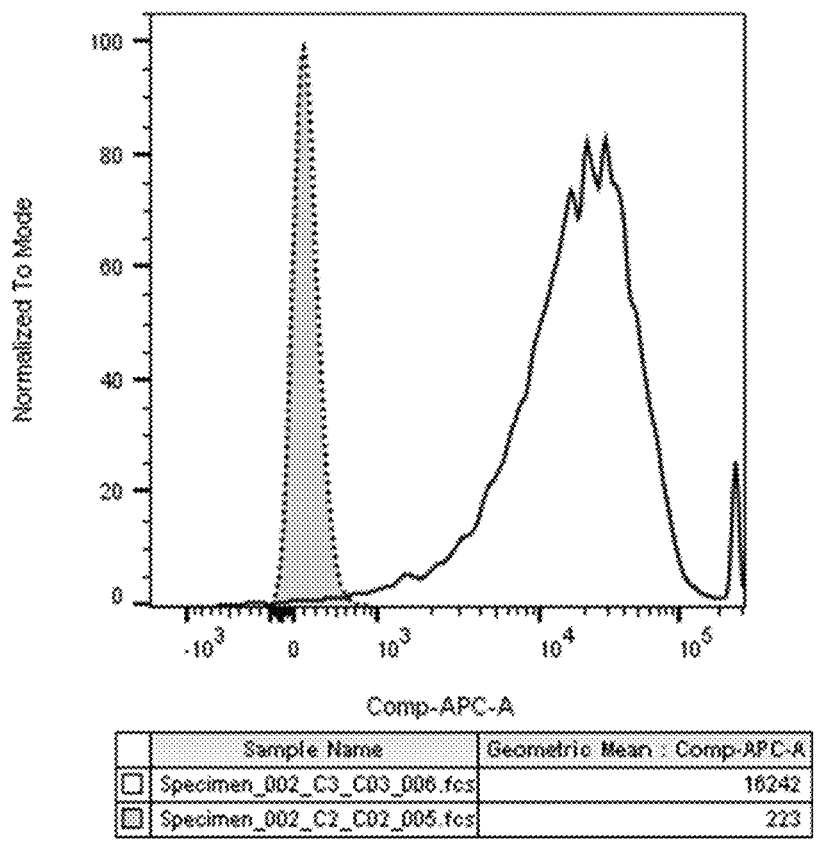
Figure 10C:
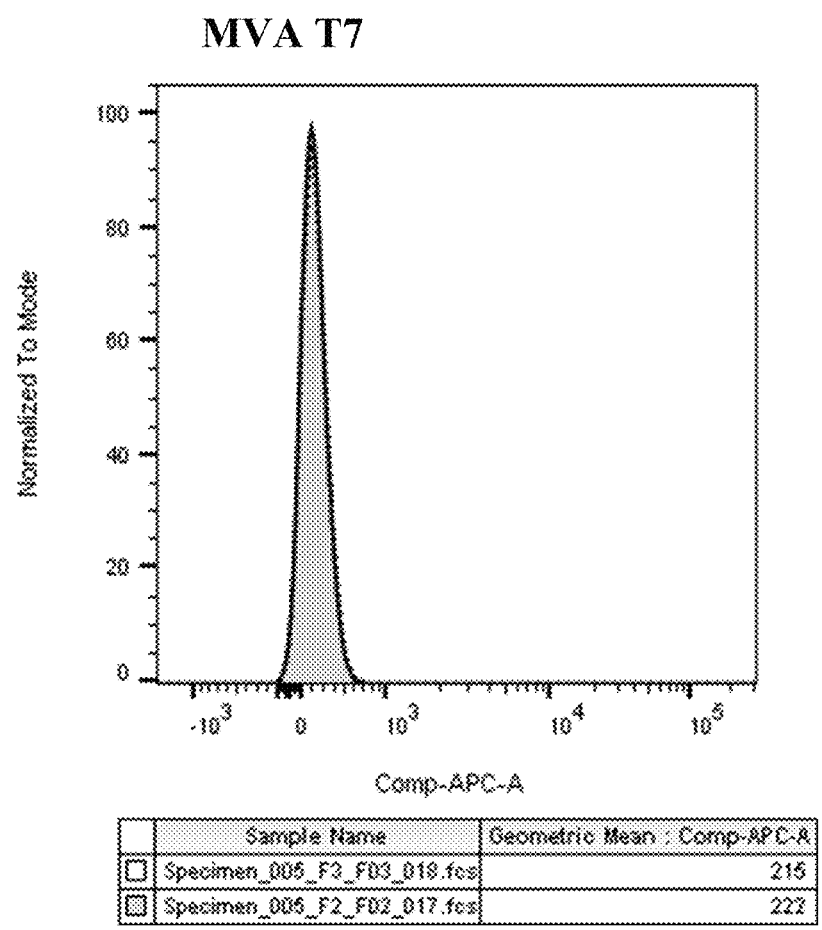

FIG. 8: Pulldown of various viruses: VV/CD39-F13, FPV/CD39-F13L and FPV/CD39-FPV108. Pull down was carried out using an anti-CD39 antibody coupled to ProG beads followed by plaque assay to titer. Data shows % of each virus pulled down with anti-CD39 antibody after subtracting the amount pulled down with a control antibody FIG. 9: Pulldown of various viruses: VV/Sema-A56R, MVA/Sema-A56R, as well as FPV generated by pseudotyping by infecting QT35/CD20-FPV108 expressing cells with wild type FPV or transfecting QT35 cells with transfer plasmid expressing Sema-A56R and infecting with wild type FPV. Pull down was carried out using an anti-Sema antibody coupled to ProG beads followed by plaque assay to titer. Data shows % of each virus pulled down with anti-Sema antibody after subtracting the amount pulled down with a control antibody FIG. 10A-C: Flow cytometry histograms showing expression of CD20 following infection with FPV-CD20-FPV108 (10A), MVA-CD20-F13L (10B) and Control MVA (T7 strain 10C). Open histograms show staining with anti-CD20 and closed histograms show staining with control IgG.

Figure 11A:
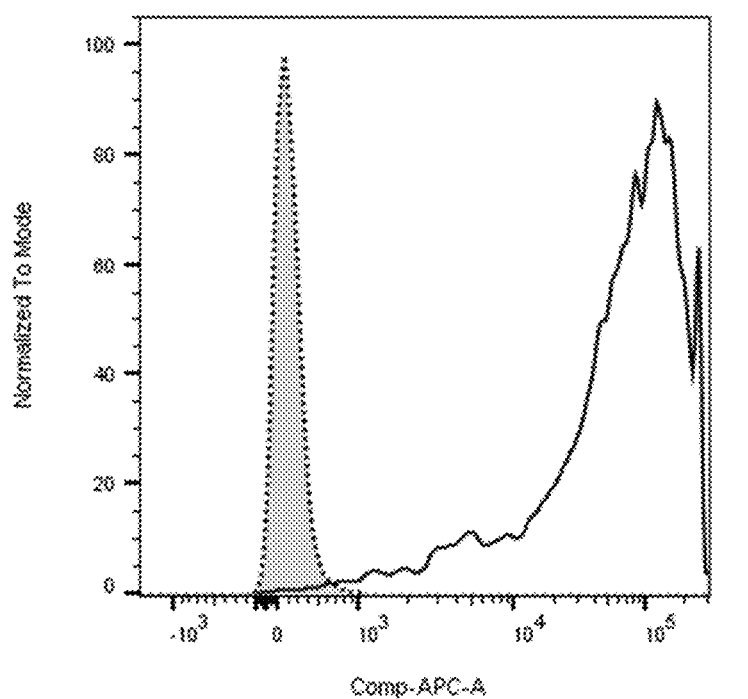
Figure 11B:
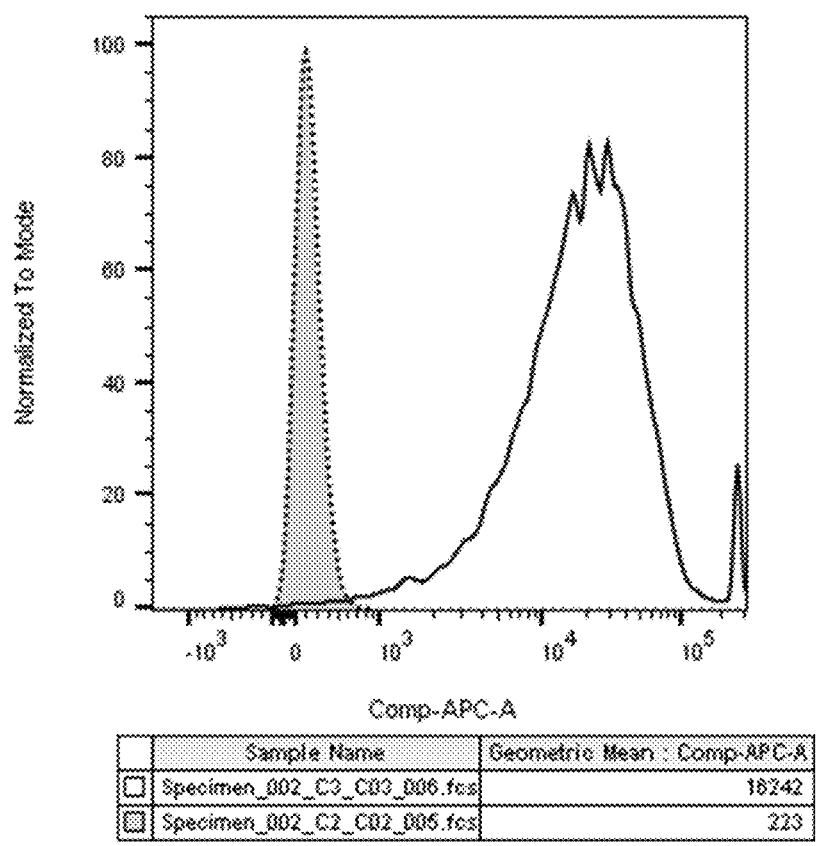
Figure 11C:
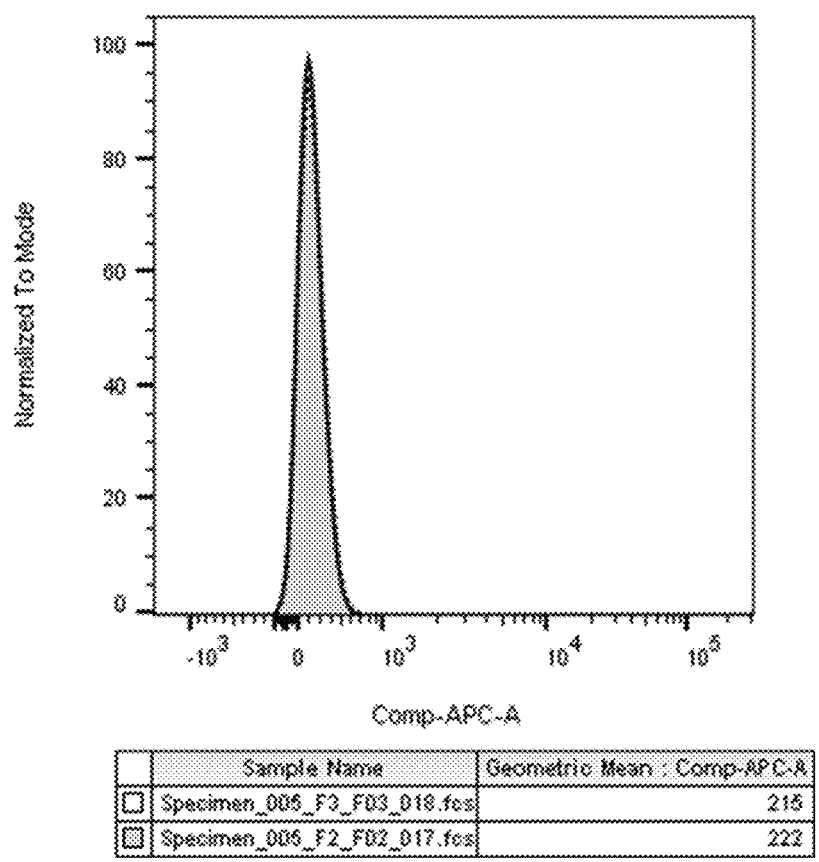

FIG. 11A-C: Flow cytometry histograms showing expression of CD39 following infection with FPV-CD39-FPV108 (11A), MVA-CD39-F13L (11B) and Control MVA (T7 strain 11C). Open histograms show staining with anti-CD39 and closed histograms show staining with control IgG.

Figure 12A:
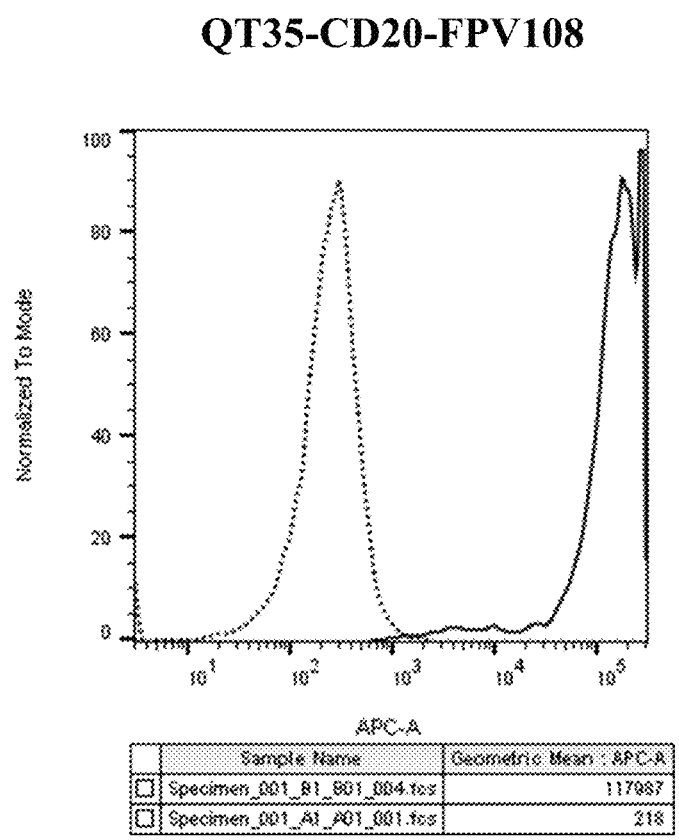
Figure 12B:
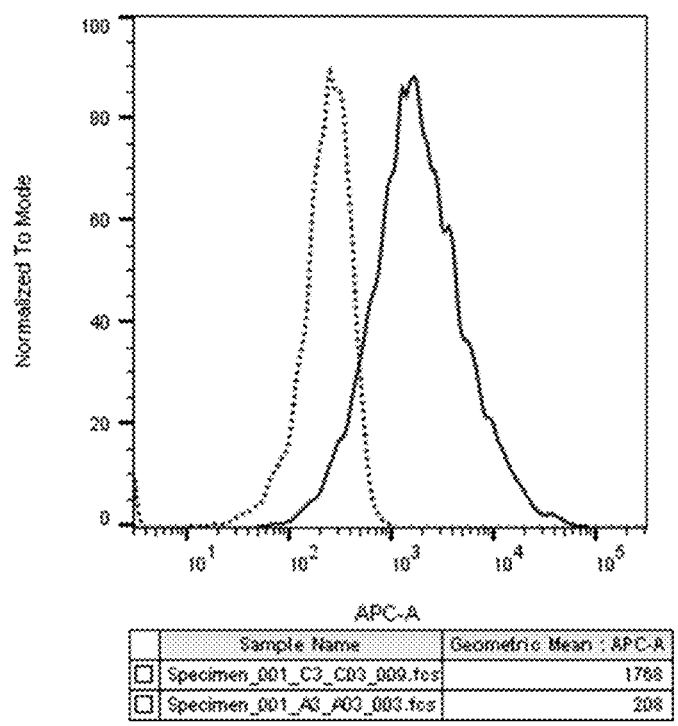
Figure 12C:
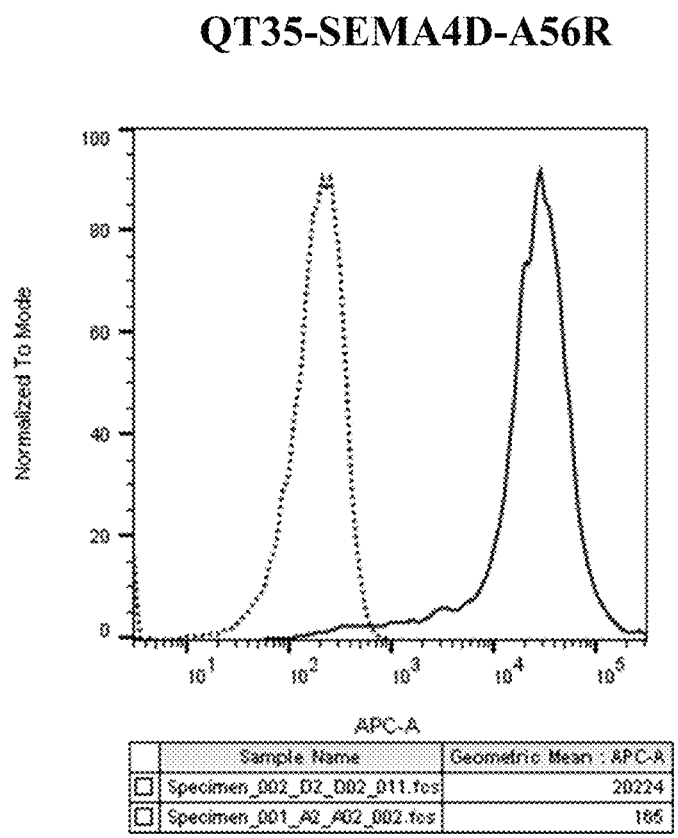

FIG. 12A-C: Flow cytometry histograms showing expression of CD20-FPV108 (12A), FZD4-FPV108 (12B) and Sema-A56R (12C) on stably transfected QT35 cells used for pseudotyping FIG. 13: Bar graph showing anti-CD20serum antibody binding on CD20-expressing Wil2S cells after initial immunization in BALB/c mice and following a booster dose of an MVA/CD20 EEV or FPV/CD20-FPV108 EEV.

FIG. 14: Table of five anti-CD20 antibodies selected from B cells of mice immunized with a MVA/CD20EEV and panning on FPV/CD20-FPV108. Table shows binding to CD20-expressing Wil2S cells and absence of binding to CD20 negative cells.

FIG. 15: Table of five anti-CD20 antibodies selected using the in vitro selection protocol described herein with a MVA/CD20-F13L and FPV/CD20-FPV108 EEV showing binding to CD20-expressing Wil2S cells.

DETAILED DESCRIPTION

This disclosure provides methods and compositions for expressing and displaying integral membrane proteins (IMPs), e.g., multi-pass (IMPs), in a conformationally intact or native state on the surface of extracellular enveloped virion particles (EEV) of poxviruses, e.g., vaccinia virus, fowlpox virus or rabbit pox virus, as a fusion with a polypeptide segment of an EEV-specific membrane-associated protein, e.g., F13L, FPV108 or RPXV041.

Definitions

The term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides that retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can comprise conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule binds. Methods of identifying nucleotide and amino acid conservative substitutions that do not eliminate antigen binding are well-known in the art (see, e.g., Brummell et al., *Biochem.* 32:1180-1 187 (1993); Kobayashi et al., *Protein Eng.* 12(10):879-884 (1999); and Burks et al., *Proc. Natl. Acad. Sci. USA* 94: 412-417 (1997)).

As used herein the term "integral membrane protein" or "IMP" refers to a protein or polypeptide that is attached to a biological membrane. One example of an IMP is a transmembrane protein, which spans the lipid bilayer of the biological membrane one or more times. Single-pass membrane proteins cross the membrane only once, while multipass membrane proteins weave in and out, crossing several times. Type I single-pass proteins are positioned with their amino terminus on the outer side of the membrane or "extra-membrane" and their carboxyl-terminus on the interior side of the membrane, or "intra-membrane." Type II single-pass proteins have their amino-terminus on the intra-membrane side. Multi-pass transmembrane proteins pass through the membrane two or more times and can have a variety of different topologies. Those proteins with an even number of transmembrane domains will have both their amino terminus and carboxy terminus on the same side of the membrane. One example of such a protein is CD20, which is expressed on B cells. Another example of an IMP with an even number of transmembrane domains is CD39, which phosphohydrolyzes ATP, and less efficiently ADP, in a $Ca^{2+}$- and $Mg^{2+}$-dependent fashion, to yield AMP. CD39 has two transmembrane domains. Those proteins with an odd number of transmembrane domains will have their amino- and carboxy termini on opposite sides of the membrane. Examples include G-protein coupled receptors, which typically have 7 transmembrane domains, with the amino terminus on the extra-membrane side and the carboxy terminus on the intra-membrane side. Certain IMPs do not have transmembrane domains and are instead anchored to the membrane, e.g., via a lipid such as glycosylphosphatidylinositol or palmitoyl group. IMPs have myriad biological functions including, but not limited to transporters, linkers, channels, receptors, enzymes, energy transduction or cell adhesion.

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, that has been engineered to have restriction sites for cloning is considered to be "isolated."

Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

As used herein, a "coding region" is a portion of nucleic acid that consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Poxvirus promoters (e.g. p7.5 or H5) or the bacteriophage T7 promoter can also be used as transcription control regions. When employing a T7 promoter, an inducible vaccinia expression system can be utilized. The vaccinia expression system can include, but is not limited, to a first recombinant vaccinia virus that encodes the entire bacteriophage T7 gene 1 coding region for T7 RNA polymerase, and a second recombinant vaccinia virus that encodes a gene of interest flanked by a T7 promoter and termination regulatory elements. Dual infection of eukaryotic cells with both recombinant vaccinia viruses results in synthesis of the T7 RNA polymerase and expression of the gene of interest controlled by the T7 promoter.

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions that encode secretory or signal peptides, which direct the secretion of a polypeptide encoded by a polynucleotide as disclosed herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

As used herein, a "library" is a representative genus of polynucleotides, e.g., a group of polynucleotides related through, for example, their origin from a single animal species, tissue type, organ, or cell type, where the library collectively comprises at least two different species within a given genus of polynucleotides. A library of polynucleotides can include, e.g., at least two, at least 5, at least 10, 100, $10^3$, $10^4$, $10^5$, $10^6$, $10^7$, $10^8$, or $10^9$ different species within a given genus of polynucleotides. In certain aspects, a library of polynucleotides as provided herein can encode a plurality of polypeptides that contains a polypeptide of interest. In certain aspects, a library of polynucleotides as provided herein can encode a plurality of immunoglobulin subunit polypeptides, e.g., heavy chain subunit polypeptides or light chain subunit polypeptides. In this context, a "library" as provided herein comprises polynucleotides of a common genus, the genus being polynucleotides encoding immunoglobulin subunit polypeptides of a certain type and class e.g., a library might encode a human, γ-1, γ-2, γ-3, γ-4, α-1, α-2, ε, or δ heavy chain, or a human κ or λ light chain. Although each member of any one library constructed according to the methods provided herein can encode the same heavy or light chain constant region and/or a membrane anchoring domain, the library can collectively comprise at least two, at least 5, or at least 10, 100, $10^1$, $10^4$, $10^5$, $10^6$, $10^7$, $10^8$, or $10^9$ different variable region associated with the common constant region.

In other embodiments, the library can contain a plurality of immunoglobulin single-chain fragments that comprise a variable region, such as a light chain variable region or a heavy chain variable region, and/or both a light chain variable region and a heavy chain variable region, e.g., an ScFv fragment.

As used herein, a "display library" is a library of polynucleotides each carried in a "display package" that expresses the polypeptide encoded by the library polynucleotide on its surface. An antibody display library, for example, can include a plurality of display packages, each displaying an antigen binding domain of an antibody on its surface. When the display library is permitted to interact with an antigen of interest, e.g., immobilized on a solid surface, those display packages that bind the antigen can be isolated from the rest of the library and recovered. The polynucleotide encoding the antigen binding domain displayed on the surface of the display package can then be isolated. Display libraries include, without limitation, phage display libraries in bacteria or libraries in eukaryotic systems, e.g., yeast display, retroviral display, or expression in DNA viruses such as poxviruses. See, e.g., U.S. Pat. Nos. 7,858,559, and 8,637,031, which are incorporated herein by reference in their entireties. In certain aspects, an antibody display library can be prepared in a poxvirus, e.g., vaccinia virus vector, fowlpox virus (FPV) vector or rabbit pox virus (RBXV) vector, as fusion proteins with an EEV-specific protein, such that the "display packages" are EEV particles. See U.S. Pat. No. 8,637,031.

Such display libraries can be screened against the IMP fusion proteins displayed on the surface of fowlpox or rabbit pox EEV as provided herein.

By "recipient cell" or "host cell" or "cell" is meant a cell or population of cells in which a recombinant protein can be expressed, a virus can be propagated, or polynucleotide libraries as provided herein can be constructed and/or propagated. A host cell as provided herein is typically a eukaryotic cell or cell line, e.g., a vertebrate, mammalian, rodent, mouse, primate, or human cell or cell line. By "a population of host cells" is meant a group of cultured cells in which a "library" as provided herein can be constructed, propagated, and/or expressed. Any host cell which is permissive for vaccinia virus, FPV or rabbit pox virus infectivity, as appropriate, is suitable for the methods provided by this disclosure. Host cells for use in the methods provided herein can be adherent, e.g., host cells that grow attached to a solid substrate, or, alternatively, the host cells can be in suspension.

Host cells as provided herein can comprise a constitutive secretory pathway, where proteins, e.g., proteins of interest expressed by the cell or by a library, are secreted from the interior of the cell either to be expressed on a cell or viral membrane surface or to be fully secreted as soluble polypeptides. In certain aspects, proteins of interest expressed on or in a biological membrane, e.g., an IMP, are expressed on the surface of an enveloped virus produced by the host cell, e.g., an extracellular enveloped vaccinia, fowlpox or rabbit virus, or EEV. IMPs can follow the same pathway as fully secreted forms or proteins, passing through to the ER lumen, except that they can be retained in the ER membrane by the presence of one or more stop-transfer signals, or "transmembrane domains." Transmembrane domains are hydrophobic stretches of about 20 amino acids that adopt an alpha-helical conformation as they transverse the membrane. Membrane embedded proteins are anchored in the phospholipid bilayer of the plasma membrane. Transmembrane forms of polypeptides of interest, e.g., membrane-anchored immunoglobulin heavy chain polypeptides typically utilize amino terminal signal peptides as do fully secreted forms.

Signal peptides, transmembrane domains, and cytosolic or "intra-membrane" domains are known for a wide variety of membrane bound and/or fully secreted proteins.

Suitable transmembrane domains can include but are not limited to the TM domain of the vaccinia virus EEV-specific protein A56R, or the FPV EEV-specific proteins or the EEV-specific FPV transmembrane proteins FPV108, FPV109, or FPV198, or rabbit pox virus transmembrane proteins RPXV041. In certain aspects the EEV specific protein can be anchored to the inner surface of the viral envelope, e.g., FPV108, or RBXV041, or VV F13L, the latter of which is anchored to the inner surface of the viral envelope via a palmitoyl group, discussed in more detail elsewhere herein.

As used herein, the term "binding molecule" refers in its broadest sense to a molecule that specifically binds to a receptor, e.g., an epitope or an antigenic determinant. As described further herein, a binding molecule can comprise one or more "antigen binding domains" described herein. A non-limiting example of a binding molecule is an antibody or fragment thereof that retains antigen-specific binding.

The terms "binding domain" and "antigen binding domain" are used interchangeably herein and refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain."

Other antigen binding domains include, without limitation, the variable heavy chain (VHH) of an antibody derived from a camelid species, or six immunoglobulin complementarity determining regions (CDRs) expressed in a fibronectin scaffold.

The terms "antibody" and "immunoglobulin" can be used interchangeably herein. An antibody (or a fragment, variant, or derivative thereof as disclosed herein) includes at least the variable region of a heavy chain (e.g., for camelid species) or at least the variable regions of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen binding fragment of an antibody to a full sized antibody, e.g., an IgG antibody that includes two complete heavy chains and two complete light chains.

The term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4 or α1-α2)). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, $IgA_2$, etc. are well characterized and are known to confer functional specialization.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have three dimensional structural characteristics, and or specific charge characteristics. An epitope is a region of a target that is bound by an antibody.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that comprises an epitope bound that can be bound by a binding molecule.

Both the light and heavy chains are divided into regions of structural and functional homology. The terms "constant" and "variable" are used functionally. In this regard, it will be appreciated that the variable regions (which can be called "variable domains" interchangeably herein) of both the variable light (VL) and variable heavy (VH) chain portions determine antigen recognition and specificity. Conversely, the constant domains of the light chain (CL) and the heavy chain (e.g., CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains are at the carboxy-terminus of the heavy and light chain, respectively.

The six "complementarity determining regions" or "CDRs" present in an antibody antigen binding domain are short, non-contiguous sequences of amino acids that are specifically positioned to form the antigen binding domain as the antibody assumes its three dimensional configuration in an aqueous environment. The remainder of the amino acids in the antigen binding domain, referred to as "framework" regions, show less inter-molecular variability. The framework regions largely adopt a j-sheet conformation and the CDRs form loops that connect, and in some cases form part of, the j-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.,* 196:901-917 (1987), which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. Immunoglobulin variable domains can also be analyzed, e.g., using the IMGT information system (www://imgt.cines.fr/) (IMGT®/V-Quest) to identify variable region segments, including CDRs. (See, e.g., Brochet et al., *Nucl. Acids Res.,* 36:W503-508, 2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), single domain antibodies such as camelid VHH antibodies, fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule. Also contemplated are immunoglobulin new antigen receptor (IgNAR) isotypes that are bivalent and comprise a single chain that includes an IgNAR variable domain (VNAR). (See, Walsh et al., *Virology* 411: 132-141, 2011).

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

As used herein, the term "affinity" refers to a measure of the strength of the binding of an individual epitope with one or more antigen binding domains, e.g., of an immunoglobulin molecule. See, e.g., Harlow et al., Antibodies: A Laboratory Manual, (Cold Spring Harbor Laboratory Press, 2nd ed. 1988) at pages 2γ-28. As used herein, the term "avidity" refers to the overall stability of the complex between a population of antigen binding domains and an antigen. See, e.g., Harlow at pages 29-34. Avidity is related to both the affinity of individual antigen binding domains in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

As used herein, the term "heavy chain subunit" or "heavy chain domain" includes amino acid sequences derived from an immunoglobulin heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof.

As used herein, the term "light chain subunit" or "light chain domain" includes amino acid sequences derived from an immunoglobulin light chain. The light chain subunit includes at least one of a VL or CL (e.g., Cκ or Cλ) domain.

Binding molecules, e.g., antibodies or antigen binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments can be physically or spatially separated by, for example, in-frame linker sequence. For example, polynucleotides encoding an IMP and a vaccinia virus EEV-specific protein can be fused, in-frame, but be separated by a polynucleotide encoding a linker or spacer, as long as the "fused" open reading frames are co-translated as part of a continuous polypeptide.

As used herein, the term "hemagglutinin tag" or "HA tag" is a protein derived from a human influenza hemagglutinin surface glycoprotein (HA) corresponding to amino acids 98-106. The HA tag is extensively used as a general epitope tag in expression vectors. Recombinant proteins can be engineered to express the HA tag, which does not appear to interfere with the bioactivity or the biodistribution of the recombinant protein. This tag facilitates the detection, isolation, and purification of the protein of interest.

In the context of polypeptides, a "linear sequence" or a "sequence" is an order of amino acids in a polypeptide from the amino or N-terminus to the carboxyl or C-terminus, in which amino acids that neighbor each other in the sequence are contiguous in the primary structure of the polypeptide.

A portion of a polypeptide that is "amino-terminal" or "N-terminal" to another portion of a polypeptide is that portion that comes earlier in the sequential polypeptide chain. Similarly, a portion of a polypeptide that is "carboxy-terminal" or "C-terminal" to another portion of a polypeptide is that portion that comes later in the sequential polypeptide chain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "eukaryote" or "eukaryotic organism" is intended to encompass all organisms in the animal, plant, and protist kingdoms, including protozoa, fungi, yeasts, green algae, single celled plants, multi celled plants, and all animals, both vertebrates and invertebrates. The term does not encompass bacteria or viruses. A "eukaryotic cell" is intended to encompass a singular "eukaryotic cell" as well as plural "eukaryotic cells," and comprises cells derived from a eukaryote.

The term "vertebrate" is intended to encompass a singular "vertebrate" as well as plural "vertebrates," and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In certain aspects, the mammal is a human subject.

The terms "tissue culture" or "cell culture" or "culture" or "culturing" refer to the maintenance or growth of plant or animal tissue or cells in vitro under conditions that allow preservation of cell architecture, preservation of cell function, further differentiation, or all three. "Primary tissue cells" are those taken directly from tissue, i.e., a population of cells of the same kind performing the same function in an organism. Treating such tissue cells with the proteolytic enzyme trypsin, for example, dissociates them into individual primary tissue cells that grow or maintain cell architecture when seeded onto culture plates. Cell cultures arising from multiplication of primary cells in tissue culture are called "secondary cell cultures." Most secondary cells divide a finite number of times and then die. A few secondary cells, however, can pass through this "crisis period," after which they are able to multiply indefinitely to form a continuous "cell line." The liquid medium in which cells are cultured is referred to herein as "culture medium" or "culture media." Culture medium into which desired molecules, e.g., viruses or proteins, e.g., immunoglobulin molecules, have been secreted during culture of the cells therein can be referred to as "conditioned medium."

As used herein, the term "identify" refers to methods in which a desired molecule, e.g., a polynucleotide encoding a protein of interest with a desired characteristics or function, is differentiated from a plurality or library of such molecules. Identification methods include "selection" and "screening" or "panning." As used herein, "selection" methods are those in which the desired molecules can be directly separated from the library, e.g., via drug resistance. As used herein, "screening" or "panning" methods are those in which pools comprising the desired molecules are subjected to an assay in which the desired molecule can be detected. Aliquots of the pools in which the molecule is detected are then divided into successively smaller pools which are likewise assayed, until a pool which is highly enriched from the desired molecule is achieved.

Poxviruses, e.g., Vaccinia, Fowlpox or Rabbit Pox Virus EEV Vectors

IMP fusion proteins as provided herein are produced in poxvirus vectors, e.g., vaccinia, fowl pox or rabbit pox virus vectors. The term "poxvirus" includes any member of the family Poxviridae. See, for example, B. Moss in: Virology, 2d Edition, B. N. Fields, D. M. Knipe et al., Eds., Raven Press, p. 2080 (1990). The genus of orthopoxvirus includes, e.g., vaccinia virus, variola virus (the virus that causes smallpox), and raccoon poxvirus. Vaccinia virus is the prototype orthopoxvirus. Fowlpox virus (FPV) belongs to the genus Avipoxvirus (APV), subfamily Chordopoxvirinae, of the family Poxviridae. The genus Avipoxvirus (APV) consists of a cluster of poxviruses that infect fowl, turkey, pigeon and many wild birds. Rabbit pox virus belongs to the genus Leporipoxvirus, which infects rabbits, hares, and squirrels. Rabbitpox virus is antigenically related to vaccinia virus. The first commercially available virus vector vaccine was a fowlpox virus, which, like vaccinia virus, is well-characterized as a vector for the expression of heterologous proteins.

Poxvirus vectors, in particular vaccinia, FPV or rabbit pox virus vectors, are used to express IMP fusion proteins as provided herein. In certain aspects, the location of a gene encoding an IMP fusion protein can be in a region of the pox virus vector that is non-essential for growth and replication of the virus so that infectious viruses are produced. The FPV genome has been sequenced and each of the open reading frames have been identified by a number. The most widely used locus for insertion of foreign genes into the FPV genome is between FPV 086 and 087, which represent the junction of the FPV left arm (FPV 084, 085, and 086) and right arm (FPV 087 and 088), respectively. The FPV vector map is shown in FIG. 2.

In the case of rabbit pox virus, the complete coding region has been sequenced. See FIG. 3. The predicted genes are numbered and shown as straight arrows; regions containing fragments of genes present in other OPVs are shown with staggered arrows to represent frame changes and have been given roman numerals. Open arrowheads indicate that an ORF is split over two lines of the diagram. The scale is shown in kb; thickened lines represent the ITRs of the genome: *, Stop codon. (Journal of General Virology, 86 (Pt 11):2969-77. December 2005)

Although a variety of non-essential regions of the vaccinia virus genome have been characterized, the most widely used locus for insertion of foreign genes is the thymidine kinase locus, located in the HindIII J fragment in the genome.

In certain FPV vectors, the sequence between 086 and 087 has been engineered to contain one or two unique restriction enzyme sites, allowing for convenient use of the trimolecular recombination method recombinant virus production, as described elsewhere herein. In certain vaccinia virus vectors, the tk locus has been engineered to contain one or two unique restriction enzyme sites, allowing for convenient use of the trimolecular recombination method recombinant virus production, as described elsewhere herein.

Polynucleotides encoding IMP fusion proteins as provided herein can be inserted into pox virus vectors, such as vaccinia, FPV, and rabbit pox virus vectors, under operable association with a transcriptional control region which functions in the cytoplasm of a poxvirus-infected cell.

Poxvirus transcriptional control regions comprise a promoter and a transcription termination signal. Gene expression in poxviruses is temporally regulated, and promoters for early, intermediate, and late genes possess varying structures. Certain poxvirus genes are expressed constitutively, and promoters for these "early-late" genes bear hybrid structures. Synthetic early-late promoters have also been developed. Suitable poxvirus promoters for expressing IMP fusion proteins as provided herein include, but are not limited to late promoters such as the 7.5-kD promoter, the MIL promoter, the 37-kD promoter, the 11-kD promoter, the 11L promoter, the 12L promoter, the 13L promoter, the 15L promoter, the 17L promoter, the 28-kD promoter, the H1L promoter, the H3L promoter, the H5L promoter, the H6L promoter, the H8L promoter, the D11L promoter, the D12L promoter, the D13L promoter, the A1L promoter, the A2L promoter, the A3L promoter, and the P4b promoter. See, e.g., Moss, B., "Poxviridae and their Replication" IN Virology, 2d Edition, B. N. Fields, D. M. Knipe et al., Eds., Raven Press, p. 2090 (1990).

Suitable poxvirus vectors include wild-type vaccinia virus, e.g., strain Western Reserve or WR, or attenuated vaccinia virus, e.g., modified vaccinia Ankara (MVA) (Mayr, A. et al., Infection 3:6-14 (1975)), wild-type fowlpox virus, and wild-type rabbit pox virus and attenuated or modified versions thereof.

During its replication cycle, a poxvirus, e.g., vaccinia virus, FPV or rabbit pox virus, produces four infectious forms which differ in their membrane structure: intracellular mature virion (IMV), the intracellular enveloped virion (IEV), the cell-associated enveloped virion (CEV) and the extracellular enveloped virion (EEV). The prevailing view is that the IMV have a single lipoprotein membrane, while the CEV and EEV are both surrounded by two membrane layers and the IEV has three envelopes. EEV is shed from the plasma membrane of the host cell and the EEV membrane is derived from the trans-Golgi.

After infection, the virus loses its membrane(s) and the DNA/protein core is transported along microtubules into the cell. The proteins encoded by early vaccinia mRNAs, fowlpox mRNAs, and rabbit pox mRNAs ("early" is defined as pre-DNA replication) lead to uncoating of the viral core and subsequent DNA replication. This replication occurs in what are termed "viral factories" which are located essentially on top of the ER. Within the viral factory, immature virions (IV) assemble and are processed to form IMV (Intracellular Mature Virus). IMVs contain a membrane that is derived from the ER. The majority of IMVs are released from the cell by cell lysis. Some IMVs are transported on microtubules to sites of wrapping by membranes of the trans-Golgi network or early endosomes. The wrapping of the IMV particles by a double membrane creates a form of vaccinia called IEVs (Intracellular Enveloped Virus). The IEVs are then transported to the cell surface on microtubules. The outer IEV membrane fuses with the plasma membrane to expose a CEV (Cell Associated Enveloped Virus) at the cell surface. Actin polymerization from the host cell can drive the CEV to infect neighboring cells, or the virus can be released as an EEV. See, e.g., Kim L. Roberts and Geoffrey L. Smith. Trends in Microbiology 16(10):472-479 (2008); Geoffrey L. Smith, et al., Journal of General Virology 83:2915-2931 (2002).

At least six virus-encoded proteins have been reported as components of the EEV envelope membrane of vaccinia virus. Of these, four proteins (A33R, A34R, A56R, and B5R) are glycoproteins, one (A36R) is a nonglycosylated transmembrane protein, and one (F13L) is a palmitoylated peripheral membrane protein. See, e.g., Lorenzo et al., Journal of Virology 74(22):10535 (2000). During infection, these proteins localize to the Golgi complex, where they are incorporated into infectious virus that is then transported and released into the extracellular medium.

FPV contains three genes that encode proteins associated with EEVs (Moss B.

Poxviridae: the viruses and their replication. In: Fields B N, Knipe D M, Howley P M, et al., editors. Fields virology. Philadelphia, Pa.: Lippincott-Raven; 1996. pp. 263γ-2671; Ogawa R, Calvert J G, Yanagida N, Nazerian K. Insertional inactivation of a fowlpox virus homologue of the vaccinia virus F12L gene inhibits the release of enveloped virions. J Gen Virol. 1993; 74: 55-64.). EEV specific proteins FPV108, FPV109, and FPV198 are similar to Vaccinia virus F13L, F12L, and A34R, respectively (Calvert J G, Ogawa R, Yanagida N, Nazerian K., Identification and functional analysis of the fowlpox virus homolog of the vaccinia virus p37K major envelope antigen gene. Virology. 1992; 191: 783-792). Missing from FPV are obvious homologues of vaccinia virus EEV genes B5R, A33R, A36R, and A56R. However, as discussed below, vaccinia A56R functions in recombinant fowlpox virus.

As provided herein, IMP fusion proteins are directed to and expressed on the EEV membrane as a fusion protein with an EEV-specific protein, e.g., vaccinia virus F13L or A56R, FPV108 (the FPV homolog of F13L), FPV109, and FPV198, rabbit pox virus RBXV041 (the rabbit pox virus homolog of F13L). The F13L (SEQ ID NO: 1), FPV108 (SEQ ID NO: 2), and RBPV041 (SEQ ID NO: 3) proteins are associated with the interior surface of the outermost EEV membrane of vaccinia virus, FPV, or rabbit pox virus, respectively. The amino acid sequence of each of these proteins and their alignment with one another is shown in FIG. 4. The percent identity between these three EEV proteins is shown in FIG. 5.

The amino acid sequence of the F13L protein from vaccinia virus strain WR is presented as SEQ ID NO: 1. The two palmitoylated cysteine residues (amino acids 85 and 86 of SEQ ID NO: 1) are underlined. Since F13L does not cross the membrane, it does not have a transmembrane domain or signal peptide.

>F13L
(SEQ ID NO: 1)
MWPFASVPAGAKCRLVETLPENMDFRSDHLTTFECFNEIITLAKKYIYIA

SFCCNPLSTTRGALIFDKLKEASEKGIKIIVLLDERGKRNLGELQSHCPD

INFITVNIDKKNNVGLLLGCFWVSDDERCYVGNASFTGGSIHTIKTLGVY

SDYPPLATDLRRRFDTFKAFNSAKNSWLNLCSAACCLPVSTAYHIKNPIG

GVFFTDSPEHLLGYSRDLDTDVVIDKLKSAKTSIDIEHLAIVPTTRVDGN

SYYWPDIYNSIIEAAINRGVKIRLLVGNWDKNDVYSMATARSLDALCVQN

DLSVKVFTIQNNTKLLIVDDEYVHITSANFDGTHYQNHGFVSFNSIDKQL

VSEAKKIFERDWVSSHSKSLKI

The A56R protein is the vaccinia virus hemagglutinin, and is a standard type I integral membrane protein comprising an amino-terminal extracellular ("extra-membrane") domain, a single transmembrane domain, and a cytoplasmic ("intra-membrane") domain. A56R comprises an N-terminal signal peptide of about 33 amino acids, an Ig-like domain extending from about amino acid 34 to about amino acid 103, a stalk region extending from about amino acid 121 to about amino acid 275, a transmembrane domain extending from about amino acid 276 to about amino acid 303, and an cytoplasmic ("inter-membrane") domain extending from about amino acid 304 to amino acid 314. See DeHaven et al., J. Gen Virol. 92:1971-1980 (2011). A56R is presented as SEQ ID NO: 5.

>A56R
(SEQ ID NO: 5)
MTRLPILLLLISLVYATPFPQTSKKIGDDATLSCNRNNTNDYVVMSAWYK

EPNSIILLAAKSDVLYFDNYTKDKISYDSPYDDLVTTITIKSLTARDAGT

YVCAFFMTSTTNDTDKVDYEEYSTELIVNTDSESTIDIILSGSTHSPETS

SKKPDYIDNSNCSSVFEIATPEPITDNVEDHTDTVTYTSDSINTVSASSG

ESTTDETPEPITDKEDHTVTDTVSYTTVSTSSGIVTTKSTTDDADLYDTY

NDNDTVPPTTVGGSTTSISNYKTKDFVEIFGITALIILSAVAIFCITYYI

YNKRSRKYKTENKV

The FPV108 protein is an F13L homolog. EEV membrane proteins are involved with EEV formation, release, and infectivity. The sequence of FPV108 is shown below:

>FPV108

(SEQ ID NO: 2)

MGNIFKPIPKADYQIVETVPQSLTAINSTNLSTYECFKRLIDLAKKEIYI

ATFCCNLSTNPEGTDILNRLIDVSSKVSVYILVDESSPHKDYEKIKSSHI

SYIKVDIGVLNNESVGNLLGNFWVVDKLHFYIGSASLMGNALTTIKNMGI

YSENNSLAMDLYFRSLDYKIISKKKCLFFTRMATKYHFFKNHNGIFFSDS

PEHMVGRKRTFDLDCVIHYIDAAKSTIDLAIVSLLPTKRTKDSIVYWPII

KDALIRAVLERGVKLRVLLGFWKKTDVISKASIKSLNELGVDHIDISTKV

FRFPVNSKVDDINNSKMMIIDGRYAHVMTANLDGSHFNHHAFVSFNCMDQ

QFTKKIAEVF ERDWISPYAK EIDMSQI

IMP fusion proteins as provided herein can be expressed in any suitable vaccinia, fowlpox virus, or rabbit pox virus. In certain embodiments, the DNA encoding an EEV fusion protein can be inserted into a region of the vaccinia, FPV or rabbit pox virus genome which is non-essential for growth and replication of the vector so that infectious viruses are produced. Although a variety of non-essential regions of the vaccinia and fowlpox virus genomes have been characterized, the most widely used locus for insertion of foreign genes is the thymidine kinase locus, located in the HindIII J fragment in the vaccinia virus genome and in the non-coding region between FPV 086 and 087 for fowlpox virus. IMP fusion proteins as provided herein can be inserted into vaccinia, rabbit pox or FPV vectors under operable association with a transcriptional control region which functions in the cytoplasm of a poxvirus-infected cell.

Suitable promoters for use in the methods described herein include, without limitation, the early/late 7.5-kD promoter, or the early/late H5 promoter (or variants thereof). Suitable FPV promoters include those disclosed in WO1989003879, for example, which is incorporated herein by reference.

The Tri-Molecular Recombination Method

Tri-molecular recombination, as disclosed in Zauderer, PCT Publication No. WO 00/028016 and in U.S. Pat. No. 7,858,559, is a high efficiency, high titer-producing method for expressing proteins of interest and or producing libraries in vaccinia virus. The tri-molecular recombination method allows the generation of recombinant viruses at efficiencies of at least 90%, and titers at least at least 2 orders of magnitude higher than those obtained by direct ligation.

In certain aspects, IMP fusion proteins for expression in vaccinia, FPV or rabbit pox virus and display on EEV as described herein can be constructed in poxvirus vectors, e.g., vaccinia virus vectors, fowlpox virus vectors or rabbit pox virus vectors, by tri-molecular recombination.

In certain embodiments, a transfer plasmid for IMP fusion proteins for expression in EEV is provided, which comprises polynucleotide flanking regions in the vaccinia virus Tk gene, the vaccinia virus H5 promoter, and NcoI and BsiWI restriction sites for inserting coding regions for desired fusion proteins. In certain embodiments, a transfer plasmid for IMP fusion proteins for expression in EEV is provided, which comprises polynucleotide flanking regions in the sequence between locus 086 and 087 of the fowlpox virus genome, the vaccinia virus H5 promoter, and XhoI and NcoI restriction sites for inserting coding regions for desired fusion proteins, and the H5 promoter.

Integral Membrane Proteins

The disclosure provides a method for expressing integral membrane proteins (IMPs) in a conformationally intact state that approaches the native conformation of the protein as it would appear in a cell in which the protein is naturally expressed. According to the disclosure, IMPs are expressed as fusion proteins with poxvirus proteins that are expressed on poxvirus, e.g., vaccinia, FPV or rabbit pox virus EEVs. IMP fusion proteins as provided herein, when expressed and displayed on the surface of EEVs, are useful as target antigens for screening libraries of binding molecules, e.g., antibody display libraries.

Any IMP can be constructed as a fusion protein according to the methods provided herein. In certain aspects the IMP is a target for immunotherapy. In certain aspects the IMP is a multi-pass IMP such as CD20, CD39, an ion channel protein or a G-protein coupled receptor (GPCR). Suitable multi-pass human IMPs for use in the construction of IMP fusion proteins as provided herein include, without limitation, the proteins listed in Table 1.

TABLE 1

Exemplary Human Multi-Pass Integral Membrane Proteins

| Protein Name | ENTREZ_gene_ID | ENTREZ gene symbol | # predicted TM domains |
|---|---|---|---|
| Poliovirus receptor-related protein 3 | 25945 | PVRL3 | 2 |
| Prominin-1 | 8842 | PROM1 | 5 |
| FL cytokine receptor | 2322 | FLT3 | 2 |
| Scavenger receptor cysteine-rich type 1 protein M130 | 9332 | CD163 | 2 |
| C-X-C chemokine receptor type 1 | 3577 | CXCR1 | 6 |
| C-X-C chemokine receptor type 3 | 2833 | CXCR3 | 7 |
| C-X-C chemokine receptor type 5 | 643 | CXCR5 | 7 |
| C-C chemokine receptor type 4 | 1233 | CCR4 | 7 |
| C-C chemokine receptor type 7 | 1236 | CCR7 | 7 |
| B-lymphocyte antigen CD20 | 931 | MS4A1 | 4 |
| Major prion protein | 5621 | PRNP | 2 |
| Plexin-C1 | 10154 | PLXNC1 | 2 |
| Multidrug resistance protein 1 | 5243 | ABCB1 | 12 |
| Putative G-protein coupled receptor 44 | 11251 | GPR44 | 7 |
| EGF-like module-containing mucin-like hormone receptor-like 2 | 30817 | EMR2 | 7 |
| Frizzled-4 | 8322 | FZD4 | 9 |
| Leukocyte surface antigen CD47 | 961 | CD47 | 5 |
| CD63 antigen | 967 | CD63 | 4 |
| Choline transporter-like protein 1 | 23446 | SLC44A1 | 9 |
| CD97 antigen | 976 | CD97 | 7 |

TABLE 1-continued

Exemplary Human Multi-Pass Integral Membrane Proteins

| Protein Name | ENTREZ_gene_ID | ENTREZ gene symbol | # predicted TM domains |
|---|---|---|---|
| Multidrug resistance-associated protein 1 | 4363 | ABCC1 | 16 |
| CAS1 domain-containing protein 1 | 64921 | CASD1 | 14 |
| Solute carrier family 12 member 6 | 9990 | SLC12A6 | 14 |
| Sodium/hydrogen exchanger 1 | 6548 | SLC9A1 | 13 |
| Solute carrier family 12 member 9 | 56996 | SLC12A9 | 13 |
| Solute carrier family 2, facilitated glucose transporter member 1 | 6513 | SLC2A1 | 12 |
| Sodium- and chloride-dependent taurine transporter | 6533 | SLC6A6 | 12 |
| Solute carrier organic anion transporter family member 4A1 | 28231 | SLCO4A1 | 12 |
| Solute carrier family 23 member 2 | 9962 | 5LC23A2 | 12 |
| Solute carrier organic anion transporter family member 3A1 | 28232 | SLCO3A1 | 12 |
| Prestin | 375611 | 5LC26A5 | 11 |
| Equilibrative nucleoside transporter 2 | 3177 | 5LC29A2 | 11 |
| Equilibrative nucleoside transporter 1 | 2030 | SLC29A1 | 11 |
| Sodium-coupled neutral amino acid transporter 1 | 81539 | SLC38A1 | 11 |
| Sodium bicarbonate cotransporter 3 | 9497 | SLC4A7 | 11 |
| Urea transporter 1 | 6563 | SLC14A1 | 10 |
| Transmembrane and coiled-coil domain-containing protein 3 | 55002 | TMC03 | 10 |
| Signal peptide peptidase-like 2A | 84888 | SPPL2A | 9 |
| Transmembrane 9 superfamily member 3 | 56889 | TM9SF3 | 9 |
| Anoctamin-9 | 338440 | ANO9 | 8 |
| Sodium/potassium-transporting ATPase subunit alpha-1 | 476 | ATP1A1 | 8 |
| Sodium/potassium-transporting ATPase subunit alpha-3 | 478 | ATP1A3 | 8 |
| Anoctamin-6 | 196527 | ANO6 | 8 |
| V-type proton ATPase 116 kDa subunit a isoform 2 | 23545 | ATP6V0A2 | 8 |
| Putative P2Y purinoceptor 10 | 27334 | P2RY10 | 7 |
| G-protein coupled receptor 39 | 2863 | GPR39 | 7 |
| Sphingosine 1-phosphate receptor 2 | 9294 | S1PR2 | 7 |
| Latrophilin-2 | 23266 | LPHN2 | 7 |
| Beta-2 adrenergic receptor | 154 | ADRB2 | 7 |
| Alpha-2C adrenergic receptor | 152 | ADRA2C | 7 |
| Thromboxane A2 receptor | 6915 | TBXA2R | 7 |
| Platelet-activating factor receptor | 5724 | PTAFR | 7 |
| Proteinase-activated receptor 1 | 2149 | F2R | 7 |
| Neuropeptide Y receptor type 1 | 4886 | NPY1R | 7 |
| Type-1 angiotensin II receptor | 185 | AGTR1 | 7 |
| Neurotensin receptor type 1 | 4923 | NTSR1 | 7 |
| Cannabinoid receptor 2 | 1269 | CNR2 | 7 |
| Prostaglandin E2 receptor EP2 subtype | 5732 | PTGER2 | 7 |
| Calcitonin gene-related peptide type 1 receptor | 10203 | CALCRL | 7 |
| Protein GPR107 | 57720 | GPR107 | 7 |
| G-protein coupled receptor 126 | 57211 | GPR126 | 7 |
| P2Y purinoceptor 8 | 286530 | P2RY8 | 7 |
| Probable G-protein coupled receptor 125 | 166647 | GPR125 | 7 |
| Transmembrane protein 87A | 25963 | TMEM87A | 7 |
| Mas-related G-protein coupled receptor member F | 116535 | MRGPRF | 7 |
| Transmembrane protein 87B | 84910 | TMEM87B | 7 |
| Proteinase-activated receptor 4 | 9002 | F2RL3 | 7 |
| Smoothened homolog | 6608 | SMO | 7 |
| EGF-like module-containing mucin-like hormone receptor-like 3 | 84658 | EMR3 | 7 |
| Neuromedin-U receptor 1 | 10316 | NMUR1 | 7 |
| EGF, latrophilin and seven transmembrane domain-containing protein 1 | 64123 | ELTD1 | 7 |
| Transmembrane protein 8A | 58986 | TMEM8A | 7 |
| Cadherin EGF LAG seven-pass G-type receptor 2 | 1952 | CELSR2 | 7 |
| Cadherin EGF LAG seven-pass G-type receptor 1 | 9620 | CELSR1 | 7 |
| Cadherin EGF LAG seven-pass G-type receptor 3 | 1951 | CELSR3 | 7 |
| Cysteinyl leukotriene receptor 1 | 10800 | CYSLTR1 | 7 |
| G-protein coupled receptor 56 | 9289 | GPR56 | 7 |

TABLE 1-continued

Exemplary Human Multi-Pass Integral Membrane Proteins

| Protein Name | ENTREZ_gene_ID | ENTREZ gene symbol | # predicted TM domains |
|---|---|---|---|
| Lipid phosphate phosphohydrolase 1 | 8611 | PPAP2A | 6 |
| Potassium voltage-gated channel subfamily A member 3 | 3738 | KCNA3 | 6 |
| Zinc transporter ZIP6 | 25800 | SLC39A6 | 6 |
| Zinc transporter ZIP14 | 23516 | SLC39A14 | 6 |
| P2Y purinoceptor 11 | 5032 | P2RY11 | 6 |
| Zinc transporter ZIP10 | 57181 | SLC39A10 | 6 |
| Cytochrome b-245 heavy chain | 1536 | CYBB | 5 |
| Prominin-2 | 150696 | PROM2 | 5 |
| Protein tweety homolog 2 | 94015 | TTYH2 | 5 |
| Protein tweety homolog 3 | 80727 | TTYH3 | 5 |
| Gamma-aminobutyric acid receptor subunit beta-3 | 2562 | GABRB3 | 4 |
| Glutamate receptor, ionotropic kainate 3 | 2899 | GRIK3 | 4 |
| Neuronal membrane glycoprotein M6-b | 2824 | GPM6B | 4 |
| Metal transporter CNNM4 | 26504 | CNNM4 | 4 |
| Metal transporter CNNM3 | 26505 | CNNM3 | 3 |
| Discoidin, CUB and LCCL domain-containing protein 2 | 131566 | DCBLD2 | 3 |
| Transmembrane protein 131-like | 23240 | KIAA0922 | 2 |
| Leucine-rich repeat transmembrane protein FLRT2 | 23768 | FLRT2 | 2 |
| Attractin | 8455 | ATRN | 2 |
| Receptor-type tyrosine-protein phosphatase gamma | 5793 | PTPRG | 2 |
| Interferon alpha/beta receptor 2 | 3455 | IFNAR2 | 2 |
| Ephrin type-A receptor 5 | 2044 | EPHA5 | 2 |
| Tyrosine-protein kinase transmembrane receptor ROR1 | 4919 | ROR1 | 2 |
| Tomoregulin-1 | 8577 | TMEFF1 | 2 |
| P2X purinoceptor 7 | 5027 | P2RX7 | 2 |
| TM2 domain-containing protein 3 | 80213 | TM2D3 | 2 |
| TM2 domain-containing protein 1 | 83941 | TM2D1 | 2 |
| G-protein coupled receptor 64 | 10149 | GPR64 | 8 |
| Psychosine receptor | 8477 | GPR65 | 6 |
| Large neutral amino acids transporter small subunit 1 | 8140 | SLC7A5 | 12 |
| Sphingosine 1-phosphate receptor 3 | 1903 | S1PR3 | 7 |
| Solute carrier organic anion transporter family member 2A1 | 6578 | SLCO2A1 | 12 |
| Type-2 angiotensin II receptor | 186 | AGTR2 | 7 |
| UPF0513 transmembrane protein | 79583 | UNQ870/PRO1886 | 2 |
| Lipid phosphate phosphohydrolase 3 | 8613 | PPAP2B | 5 |
| Blood vessel epicardial substance | 11149 | BVES | 3 |
| Sodium/potassium/calcium exchanger 6 | 80024 | 5LC24A6 | 13 |
| 5-hydroxytryptamine receptor 2B | 3357 | HTR2B | 7 |
| Mucolipin-1 | 57192 | MCOLN1 | 6 |
| Cadherin-8 | 1006 | CDH8 | 2 |
| Adenosine receptor A1 | 134 | ADORA1 | 7 |
| Probable G-protein coupled receptor 110 | 266977 | GPR110 | 7 |
| Chemokine receptor-like 1 | 1240 | CMKLR1 | 7 |
| Proton-coupled folate transporter | 113235 | SLC46A1 | 11 |
| Sphingosine 1-phosphate receptor 4 | 8698 | S1PR4 | 7 |
| Protein FAM171A2 | 284069 | FAM171A2 | 2 |
| Alpha-2A adrenergic receptor | 150 | ADRA2A | 7 |
| C-X-C chemokine receptor type 7 | 57007 | CXCR7 | 7 |
| Apelin receptor | 187 | APLNR | 7 |
| Probable G-protein coupled receptor 116 | 221395 | GPR116 | 7 |
| Metalloreductase STEAP4 | 79689 | STEAP4 | 6 |
| Solute carrier organic anion transporter family member 4C1 | 353189 | SLCO4C1 | 12 |
| ATP-binding cassette sub-family A member 8 | 10351 | ABCA8 | 14 |
| Vasoactive intestinal polypeptide receptor 1 | 7433 | VIPR1 | 7 |
| SID1 transmembrane family member 2 | 51092 | SIDT2 | 11 |
| Equilibrative nucleoside transporter 4 | 222962 | 5LC29A4 | 10 |
| Succinate receptor 1 | 56670 | SUCNR1 | 7 |
| Metal transporter CNNM2 | 54805 | CNNM2 | 4 |
| Probable palmitoyltransferase ZDHHC5 | 25921 | ZDHHC5 | 4 |
| Solute carrier family 22 member 16 | 85413 | 5LC22A16 | 12 |
| Leukotriene B4 receptor 1 | 1241 | LTB4R | 7 |
| Pannexin-1 | 24145 | PANX1 | 4 |
| Sodium-dependent glucose transporter 1 | 91749 | NAGLT1 | 11 |
| Sodium/calcium exchanger 1 | 6546 | SLC8A1 | 10 |
| Neuronal acetylcholine receptor subunit alpha-3 | 1136 | CHRNA3 | 4 |

TABLE 1-continued

Exemplary Human Multi-Pass Integral Membrane Proteins

| Protein Name | ENTREZ_gene_ID | ENTREZ gene symbol | # predicted TM domains |
|---|---|---|---|
| Retinoic acid-induced protein 3 | 9052 | GPRC5A | 7 |
| Lysophosphatidic acid receptor 5 | 57121 | LPAR5 | 7 |
| Probable G-protein coupled receptor 132 | 29933 | GPR132 | 7 |
| Sphingosine 1-phosphate receptor 5 | 53637 | S1PR5 | 7 |
| Endothelin-1 receptor | 1909 | EDNRA | 7 |
| Probable G-protein coupled receptor 124 | 25960 | GPR124 | 7 |
| Solute carrier family 12 member 7 | 10723 | SLC12A7 | 12 |
| Thyrotropin receptor | 7253 | TSHR | 7 |
| Transient receptor potential cation channel subfamily V member 2 | 51393 | TRPV2 | 6 |
| Glutamate receptor delta-1 subunit | 2894 | GRID1 | 4 |
| Gamma-aminobutyric acid receptor subunit alpha-2 | 2555 | GABRA2 | 4 |
| Sphingosine 1-phosphate receptor 1 | 1901 | S1PR1 | 7 |
| Prostaglandin E2 receptor EP3 subtype | 5733 | PTGER3 | 7 |
| Probable G-protein coupled receptor 174 | 84636 | GPR174 | 7 |
| Glutamate receptor 2 | 2891 | GRIA2 | 3 |
| Amiloride-sensitive sodium channel subunit delta | 6339 | SCNN1D | 2 |
| 5-hydroxytryptamine receptor 1D | 3352 | HTR1D | 7 |
| Goliath homolog | 55819 | RNF130 | 2 |
| ATP-binding cassette sub-family A member 7 | 10347 | ABCA7 | 11 |
| Prostacyclin receptor | 5739 | PTGIR | 7 |
| Probable G-protein coupled receptor 176 | 11245 | GPR176 | 7 |
| Thyrotropin-releasing hormone receptor | 7201 | TRHR | 7 |
| Claudin-12 | 9069 | CLDN12 | 4 |
| Protein FAM38A | 9780 | FAM38A | 29 |
| Niemann-Pick C1 protein | 4864 | NPC1 | 13 |
| Synaptic vesicle glycoprotein 2A | 9900 | SV2A | 12 |
| Signal peptide peptidase-like 2B | 56928 | SPPL2B | 9 |
| Rhomboid family member 2 | 79651 | RHBDF2 | 7 |
| Immunoglobulin superfamily member 1 | 3547 | IGSF1 | 4 |
| Dolichyl-diphosphooligosaccharide--protein glycosyltransferase subunit 2 | 6185 | RPN2 | 3 |
| Transmembrane emp24 domain-containing protein 9 | 54732 | TMED9 | 2 |
| Steryl-sulfatase | 412 | STS | 2 |
| Transmembrane 9 superfamily member 1 | 10548 | TM9SF1 | 9 |
| Melanoma inhibitory activity protein 3 | 375056 | MIA3 | 2 |
| Arylsulfatase F | 416 | ARSF | 2 |
| Solute carrier family 2, facilitated glucose transporter member 4 | 6517 | SLC2A4 | 12 |
| Anoctamin-5 | 203859 | ANU5 | 8 |
| Nicalin | 56926 | NCLN | 2 |

In certain aspects, the multi-pass IMP is a G protein-coupled receptor (GPCR), e.g., FZD4, CXCR4, leucine rich repeat containing G protein-coupled receptor 5 or leucine rich repeat containing G protein-coupled receptor 4. In certain aspects the multi-pass IMP is CD20; purinergic receptor P2X 2; frizzled class receptor 7, or C-X-C motif chemokine receptor 4.

In other aspects, the multi-pass IMP is CD39. In certain aspects, the multi-pass IMP is an ion channel protein such as any of the chloride channels, which comprise a superfamily of channels that consists of approximately 13 members including ClCs, CLICs, Bestrophins and CFTRs; potassium channels; voltage-gated potassium channels e.g., Kvs, Kirs, etc.; calcium-activated potassium channels, e.g., BKCa or MaxiK, SK, etc.; inward-rectifier potassium channels; two-pore-domain potassium channels (leak channels); sodium channels; voltage-gated sodium channels (NaVs); epithelial sodium channels (ENaCs); calcium channels (CaVs); proton channels; voltage-gated proton channels; non-selective cation channels; transient receptor potential channels; endoplasmic reticulum channels: RyR, SERCA, ORAi; mitochondrial channels: mPTP, KATP, BK, IK, CLIC5, Kv7.4 at the inner membrane and VDAC and CLIC4 as outer membrane channels; transient receptor potential channels; sodium voltage-gated channel alpha subunit 5; sodium voltage-gated channel alpha subunit 9; sodium voltage-gated channel alpha subunit 10; potassium voltage-gated channel subfamily A member 1; potassium voltage-gated channel subfamily A member 2; hyperpolarization activated cyclic nucleotide gated potassium channel 1; hyperpolarization activated cyclic nucleotide gated potassium and sodium channel 2; hyperpolarization activated cyclic nucleotide gated potassium channel 3; hyperpolarization activated cyclic nucleotide gated potassium channel 4; potassium voltage-gated channel subfamily H member 1; parathyroid hormone 1 receptor;

Polynucleotides Encoding IMP Fusion Proteins for Expression on Poxvirus EEV

This disclosure provides an isolated polynucleotide for expression of an integral membrane protein or fragment thereof in a conformationally-intact form in the context of a biological membrane, as a fusion with a protein or fragment thereof specific for vaccinia virus EEV. By "conformationally intact" is meant that the protein appears, or is displayed, in a native or close to native conformation in the context of a biological lipid bilayer membrane, much as the protein would appear in its native state.

In one aspect, the disclosure provides an isolated polynucleotide that includes a first nucleic acid fragment that encodes an integral membrane protein (IMP) or fragment thereof, e.g., a multi-pass IMP, where the IMP or fragment thereof comprises at least one extra-membrane region, at least one transmembrane domain and at least one intra-membrane region, and where a portion of the first nucleic acid fragment encoding at least one intra-membrane region is situated at the 5' or 3' end of the first nucleic acid fragment; and a second nucleic acid fragment that encodes a vaccinia virus F13L protein (SEQ ID NO: 1) or functional fragment thereof, FPV108 (SEQ ID NO: 2) or functional fragment thereof, or RPXV041 (SEQ ID NO: 3) or functional fragment thereof, where the second nucleic acid fragment is fused in frame to a portion of the first nucleic acid fragment that encodes an intra-membrane region of the IMP. The first nucleic acid fragment and the second nucleic acid fragment can, in some instances, be separated by a nucleic acid encoding a linker or other spacer. The polynucleotide can further include a poxvirus promoter operably associated with the first and second nucleic acid fragments, allowing expression of the polynucleotide in the cytoplasm of a poxvirus-infected cell. According to this aspect, a poxvirus-infected cell that contains the polynucleotide can express an IMP-F13L fusion protein, an IMP-FPV108 fusion protein, or IMP-RPXV041 fusion protein, respectively, as part of the outer envelope membrane of an extracellular enveloped virion (EEV), such as a vaccinia virus EEV, a fowlpox virus EEV, or a rabbit pox virus EEV. Schematic diagrams showing expression of an IMP as a fusion with FPV108 are shown in FIG. 1B, FIG. 1C and FIG. 1D.

In certain aspects, the IMP or fragment thereof can be a multi-pass membrane protein comprising at least two, at least three, at least four, at least five, at least six, at least seven, at least eight, at least nine, at least ten, at least eleven, at least twelve, or even more transmembrane (TM) domains, such as ion channel proteins and those proteins listed in Table 1.

Where the IMP has an odd number of TM domains, one end of the IMP, either the N-terminus or the C-terminus, will be naturally situated on the extra-membrane side of the biological membrane and the other end of the IMP will be situated on the intra-membrane side of the IMP. Since the F13L protein, FPV108 protein, and RPXV041 proteins are wholly internal to the outer membrane of poxvirus EEVs, the end of the IMP, the N-terminus or the C-terminus that is situated internal to the membrane can be fused to F13L, FPV108, or RPXV041, for example. Thus for an IMP such as a typical 7-TM domain GPCR in which the N-terminus of the protein is extra-membrane and the C-terminus is intra-membrane, the N-terminus of F13L, FPV108, or RPXV041 can be fused to the C-terminus of the GPCR as shown in FIG. 1B for these EEV-specific proteins, for example. Accordingly, a polynucleotide as above is provided where the first nucleic acid fragment encodes an IMP with an odd number of transmembrane domains, where the 5' end of the first nucleic acid fragment encodes the extra-membrane region, and the 3' end of the first nucleic acid fragment encodes the intra-membrane region of the IMP, the latter being fused to the 5' end of the nucleic acid fragment encoding F13L, or the FPV homolog FPV108 or RPXV041 or a fragment thereof.

In an exemplary polynucleotide of this type, the first polynucleotide can encode the human frizzled-4 protein (FZD4), or a fragment thereof, a target for immunotherapy of certain human cancers, fused to the N-terminus of F13L, FPV108 or RPXV041. Accordingly, a polynucleotide which encodes an FZD4-FPV108 fusion protein is provided. An exemplary polynucleotide according to this aspect encodes the mature fusion protein, amino acids 20 to 892 of SEQ ID NO: 4, as shown below. The polynucleotide can further encode a signal peptide, e.g., the signal peptide of FZD4, amino acids 1 to 19 of SEQ ID NO: 4.

>FZD (FL) - FPV108

(SEQ ID NO: 4)

MGWSCIILFLVATATGAHS FGDEEERRCDPIRISMCQNLGYNVTK

MPNLVGHELQTDAELQLTTFTPLIQYGCSSQLQFFLCSVYVPMCTEKINI

PIGPCGGMCLSVKRRCEPVLKEFGFAWPESLNCSKFPPQNDHNHMCMEGP

GDEEVPLPHKTPIQPGEECHSVGTNSDQYIWVKRSLNCVLKCGYDAGLYS

RSAKEFTDIWMAVWASLCFISTAFTVLTFLIDSSRFSYPERPIIFLSMCY

NIYSIAYIVRLTVGRERISCDFEEAAEPVLIQEGLKNTGCAIIFLLMYFF

GMASSIWWVILTLTWFLAAGLKWGHEAIEMHSSYFHIAAWAIPAVKTIVI

LIMRLVDADELTGLCYVGNQNLDALTGFVVAPLFTYLVIGTLFIAAGLVA

LFKIRSNLQKDGTKTDKLERLMVKIGVFSVLYTVPATCVIACYFYEISNW

ALFRYSADDSNMAVEMLKIFMSLLVGITSGMWIWSAKTLHTWQKCSNRLV

NSGKVKREKRGNGWVKPGKGSETVVVHHHHHHGGGGSGSLGGSSG*MGNIF*

*KPIPKADYQIVETVPQSLTAINSTNLSTYECFKRLIDLAKKEIYIATFCC*

*NLSTNPEGTDILNRLIDVSSKVSVYILVDESSPHKDYEKIKSSHISYIKV*

*DIGVLNNESVGNLLGNFWVVDKLHFYIGSASLMGNALTTIKNMGIYSENN*

*SLAMDLYFRSLDYKIISKKKCLFFTRMATKYHFFKNHNGIFFSDSPEHMV*

*GRKRTFDLDCVIHYIDAAKSTIDLAIVSLLPTKRTKDSIVYWPIIKDALI*

*RAVLERGVKLRVLLGFWKKTDVISKASIKSLNELGVDHIDISTKVFRFPV*

*NSKVDDINNSKMMIIDGRYAHVMTANLDGSHFNHHAFVSFNCMDQQFTKK*

*IAEVFERDWISPYAKEIDMSQI.*

Underline = his tag and linker
Bold = FZD4
Italics = FPV108
Large font = Signal Sequence In another exemplary polynucleotide of this type, the first polynucleotide can encode A CXC chemokine receptor, or a fragment thereof, fused to the N-terminus of FPV108. CXC chemokine receptors are likewise targets for immunotherapy of certain human cancers. An exemplary CXC chemokine receptor is CXCR4, or a fragment thereof. Accordingly, a polynucleotide which encodes a CXC chemokine receptor-FP108 fusion protein, e.g., a CXCR4-FPV108 fusion protein is provided. An exemplary polynucleotide according to this aspect encodes SEQ ID NO: 9, as shown below.

>CSWCR4 - FPV108

(SEQ ID NO: 9)

MEGISIYTSDNYTEEMGSGDYDSMKEPCFREENANFNKIFLPTIYSIIFLTGIVGNGLV

ILVMGYQKKLRSMTDKYRLHLSVADLLFVITLPFWAVDAVANWYFGNFLCKAVHVIYTVNLYSS

```
VLILAFISLDRYLAIVHATNSQRPRKLLAEKVVYVGVWIPALLLTIPDFIFANVSEADDRYICD

RFYPNDLWVVVFQFQHIMVGLILPGIVILSCYCIIISKLSHSKGHQKRKALKTTVILILAFFAC

WLPYYIGISIDSFILLEIIKQGCEFENTVHKWISITEALAFFHCCLNPILYAFLGAKFKTSAQH

ALTSVSRGSSLKILSKGKRGGHSSVSTESESSSFHSSVHHHHHHGGGGSGSLMSKGEELFTGVV

PILVELDGDVNGHKFSVSGEGEGDATYGKLTLKFICTTGKLPVPWPTLVTTLTYGVQCFSRYPD

HMKRHDFFKSAMPEGYVQERTISFKDDGNYKTRAEVKFEGDTLVNRIELKGIDFKEDGNILGHK

LEYNYNSHNVYITADKQKNGIKANFKTRHNIEDGGVQLADHYQQNTPIGDGPVLLPDNHYLSTQ

SALSKDPNEKRDHMVLLEFVTAAGITHGMDELYKGGSSGMGNIFKPIPKADYQIVETVPQSLTA

INSTNLSTYECFKRLIDLAKKEIYIATFCCNLSTNPEGTDILNRLIDVSSKVSVYILVDESSPH

KDYEKIKSSHISYIKVDIGVLNNESVGNLLGNFWVVDKLHFYIGSASLMGNALTTIKNMGIYSE

NNSLAMDLYFRSLDYKIISKKKCLFFTRMATKYHFFKNHNGIFFSDSPEHMVGRKRTFDLDCVI

HYIDAAKSTIDLAIVSLLPTKRTKDSIVYWPIIKDALIRAVLERGVKLRVLLGFWKKTDVISKA

SIKSLNELGVDHIDISTKVFRFPVNSKVDDINNSKMMIIDGRYAHVMTANLDGSHFNHHAFVSF

NCMDQQFTKKIAEVFERDWISPYAKEIDMSQI.
Underline = his tag and linker
Bold = CXCr4
Italics = FPV108
Dotted underline = GFP
```

As will be evident to a person of ordinary skill in the art, a multi-pass membrane protein having an even number of transmembrane domains will be inserted into a biological membrane such that its N-terminus and its C-terminus are on the same side of the membrane, either on the extra-membrane side of the membrane, or on the intra-membrane side of the membrane. Since the F13L, FPV108, and RPXV041 proteins are situated entirely on the intra-membrane side of poxvirus EEVs, formation of an IMP-F13L, IMP-FPV108, or RPXV041 fusion protein properly embedded in the membrane would need at least one of the N-terminus or the C-terminus of the IMP or fragment thereof to be internal to the membrane. Where the IMP has an even number of TM domains and both are situated internally, the poxvirus EEV-specific protein, e.g., F13L, FPV108, or RPXV041 can be fused either to the N-terminus of the IMP or to the C-terminus of the IMP. If the full-length IMP is situated such that both the N- and C-terminus are extra-membrane, a fragment of the IMP having an odd number of TM domains can be fused to the poxvirus EEV-specific protein.

Accordingly, the disclosure provides a polynucleotide as described above that encodes an IMP with an even number of transmembrane domains, where both the 5' and 3' ends of the first nucleic acid fragment encode intra-membrane regions. In certain aspects the 3' end of the nucleic acid fragment encoding the poxvirus EEV-specific protein, e.g., F13L, FPV108, or RPXV041, can be fused to the 5' end of the nucleic acid fragment encoding the IMP, in certain aspects the 5' end of the nucleic acid fragment encoding the poxvirus EEV-specific protein can be fused to the 3' end of the nucleic acid fragment encoding the IMP.

An exemplary IMP of this type is human CD20, a 4-TM domain IMP expressed on human B cells, which is a target for immunotherapy of B cell leukemias, lymphomas, and myelomas. A diagram of a CD20-FPV108 fusion protein in which the C-terminus of CD20 is fused to the N-terminus of FPV108 is shown in FIG. 1C. Accordingly, a polynucleotide which encodes a CD20-FPV108 fusion protein is provided. An exemplary polynucleotide according to this aspect encodes SEQ ID NO: 10, as shown below.

```
>CD20-FPV108
                                          (Seq ID NO: 10)
MA TPRNSVNGTFPAEPMKGPIAMQSGPKPLFRRMSSLVGPTQSFFMRE

SKTLGAVQIMNGLFHIALGGLLMIPAGIYAPICVTVWYPLWGGIMYIISG

SLLAATEKNSRKCLVKGKMIMNSLSLFAAISGMILSIMDILNIKISHFLK

MESLNFIRAHTPYINIYNCEPANPSEKNSPSTQYCYSIQSLFLGILSVML

IFAFFQELVIAGIVENEWKRTCSRPKSNIVLLSAEEKKEQTIEIKEEVVG

LTETSSQPKNEEDIEIIPIQEEEEEETETNFPEPPQDQESSPIENDSSPV

HHHHHHGGGGSGSLGGSSGMGNIFKPIPKADYQIVETVPQSLTAINSTNL

STYECFKRLIDLAKKEIYIATFCCNLSTNPEGTDILNRLIDVSSKVSVYI

LVDESSPHKDYEKIKSSHISYIKVDIGVLNNESVGNLLGNFWVVDKLHFY

IGSASLMGNALTTIKNMGIYSENNSLAMDLYFRSLDYKIISKKKCLFFTR

MATKYHFFKNHNGIFFSDSPEHMVGRKRTFDLDCVIHYIDAAKSTIDLAI

VSLLPTKRTKDSIVYWPIIKDALIRAVLERGVKLRVLLGFWKKTDVISKA

SIKSLNELGVDHIDISTKVFRFPVNSKVDDINNSKMMIIDGRYAHVMTAN

LDGSHFNHHAFVSFNCMDQQFTKKIAEVFERDWISPYAKEIDMSQI.
Underline = his tag and linker
Bold = CD20
Italics = FPV108
Large font = change from native sequence to accommodate NcoI
site
```

In another exemplary polynucleotide of this type, the first polynucleotide can encode CD39, a protein having two transmembrane domains, or a fragment thereof, fused to the N-terminus of FPV108. CD39 is a target which promotes an anti-tumor immune response immunotherapy of certain human cancers. Accordingly, a polynucleotide which encodes a CD39-FPV108 fusion protein is provided. An exemplary polynucleotide according to this aspect encodes SEQ ID NO: 11 shown below.

>CD39-FPV108
(SEQ ID NO: 11)
MEDIKDSKVKRFCSKNILIILGFTSILAVIALIAVGLTQNKPLPENVKYGI

VLDAGSSHTNLYIYKWPAEKENDTGVVQQLEECQVKGPGISKYAQKTDEIG

AYLAECMELSTELIPTSKHHQTPVYLGATAGMRLLRMESEQSADEVLAAVS

TSLKSYPFDFQGAKIITGQEEGAYGWITINYLLGRFTQEQSWLSLISDSQK

QETFGALDLGGASTQITFVPQNSTIESPENSLQFRLYGEDYTVYTHSFLCY

GKDQALWQKLAKDIQVSSGGVLKDPCFNPGYEKVVNVSELYGTPCTKRFEK

KLPFDQFRIQGTGDYEQCHQSILELFNNSHCPYSQCAFNGVFLPPLHGSFG

AFSAFYFVMDFFKKVAKNSVISQEKMTEITKNFCSKSWEETKTSYPSVKEK

YLSEYCFSGAYILSLLQGYNFTDSSWEQIHFMGKIKDSNAGWTLGYMLNLT

NMIPAEQPLSPPLPHSTYIGLMVLFSLLLVAVAITGLFIYSKPSYFWKEAV

VHHHHHHGGGGSGSLGGSSGMGNIFKPIPKADYQIVETVPQSLTAINSTNL

STYECFKRLIDLAKKEIYIATFCCNLSTNPEGTDILNRLIDVSSKVSVYIL

VDESSPHKDYEKIKSSHISYIKVDIGVLNNESVGNLLGNFWVVDKLHFYIG

SASLMGNALTTIKNMGIYSENNSLAMDLYFRSLDYKIISKKKCLFFTRMAT

KYHFFKNHNGIFFSDSPEHMVGRKRTFDLDCVIHYIDAAKSTIDLAIVSLL

PTKRTKDSIVYWPIIKDALIRAVLERGVKLRVLLGFWKKTDVISKASIKSL

NELGVDHIDISTKVFRFPVNSKVDDINNSKMMIIDGRYAHVMTANLDGSHF

NHHAFVSFNCMDQQFTKKIAEVFERDWISPYAKEIDMSQI.
Underline = his tag and linker
Bold = CD39
Italics = FPV108

The disclosure also provides a polynucleotide as described above that encodes an IMP with a single transmembrane domain, where the 5' end of the first nucleic acid fragment encodes an intra-membrane region. In certain aspects the 3' end of the nucleic acid fragment encoding the poxvirus EEV-specific protein, e.g., F13L, FPV108, or RPXV041, can be fused to the 5' end of the nucleic acid fragment encoding the IMP, in certain aspects the 5' end of the nucleic acid fragment encoding the poxvirus EEV-specific protein can be fused to the 3' end of the nucleic acid fragment encoding the IMP.

An exemplary IMP of this type is a human semaphorin, SEMA, a single TM domain IMP, which is a target for immunotherapy of various cancers, inflammatory disorders, and neurodegenerative disorders and diseases. A diagram of a SEMA-A56R fusion protein, e.g., semaphoring 4D (SEMA4D), in which the C-terminus of SEMA4D is fused to the N-terminus of VV A56R is shown in FIG. 1A. Accordingly, a polynucleotide which encodes a SEMA-A56R fusion protein is provided. An exemplary polynucleotide according to this aspect encodes SEQ ID NO: 6, as shown below.

>SEMA-A56R (SEQ ID NO: 6)

*MGWSCHLFLVATATGAHS*FAPIPRITWEHREVHLVQFHEPDIYNYSALLL

SEDKDTLYIGAREAVFAVNALNISEKQHEVYWKVSEDKKAKCAEKGKSKQ

TECLNYIRVLQPLSATSLYVCGTNAFQPACDHLNLTSFKFLGKNEDGKGR

CPFDPAHSYTSVMVDGELYSGTSYNFLGSEPIISRNSSHSPLRTEYAIPW

LNEPSFVFADVIRKSPDSPDGEDDRVYFFFTEVSVEYEFVFRVLIPRIAR

VCKGDQGGLRTLQKKWTSFLKARLICSRPDSGLVFNVLRDVFVLRSPGLK

VPVFYALFTPQLNNVGLSAVCAYNLSTAEEVFSHGKYMQSTTVEQSHTKW

VRYNGPVPKPRPGACIDSEARAANYTSSLNLPDKTLQFVKDHPLMDDSVT

PIDNRPRLIKKDVNYTQIVVDRTQALDGTVYDVMFVSTDRGALHKAISLE

HAVHIIEETQLFQDFEPVQTLLLSSKKGNRFVYAGSNSGVVQAPLAFCGK

HGTCEDCVLARDPYCAWSPPTATCVALHQTESPSRGLIQEMSGDASVCPD

KSKGSYRQHFFKHGGTAELKCSQKSNLARVFWKFQNGVLKAESPKYGLMG

RKNLLIFNLSEGDSGVYQCLSEERVKNKTVFQVVAKHVLEVKVVPKPVVA

PTLSVVQTEGSRIATKVLVASTQGSSPPTPAVQATSSGAITLPPKPAPTG

TSCEPKIVINTVPQLHSEKTMYLKSSDTSTTNDTDKVDYEEYSTELIVNT

DSESTIDIILSGSTHSPETSSKKPDYIDNSNCSSVFEIATPEPITDNVED

HTDTVTYTSDSINTVSASSGESTTDETPEPITDKEDHTVTDTVSYTTVST

SSGIVTTKSTTDDADLYDTYNDNDTVPPTTVGGSTTSISNYKTKDFVEIF

GITALIILSAVAIFCITYYIYNKRSRKYKTENKV.

Underline = A56R tag

Bold = SEMA4D

Italics = signal sequence

In polynucleotides as provided above, the first and second nucleic acid fragments can be directly fused, or alternatively they can be separated by a nucleic acid fragment encoding a linker or spacer or other polypeptide fragment. In certain aspects, a polynucleotide as provided above can further include a third nucleic acid fragment that encodes a heterologous peptide polypeptide, either between the first and second nucleic acid fragments, or on either side. The heterologous peptide can be, for example, a linker sequence, an amino acid tag or label, or a peptide or polypeptide sequence that facilitates purification. In certain aspects the heterologous peptide is a 6-histidine tag (SEQ ID NO: 15) fused, e.g., to the C-terminus of the fusion protein.

In certain aspects, a polynucleotide as provided herein is operably associated with a poxvirus promoter. Suitable promoters are described elsewhere herein. In certain aspects the promoter is a poxvirus p7.5 promoter or a poxvirus H5 promoter. Alternatively, fowlpox virus promoters including those disclosed in WO 198900379, which is incorporated herein by reference, can be used.

A polynucleotide as provided herein can be or can be part of, a poxvirus genome, where the poxvirus genome, upon introduction into a suitable permissive host cell, can produce infectious EEV that display the IMP-F13L, -FPV108, or -RPXV041 fusion protein on their surface. In certain aspects the poxvirus genome is a vaccinia virus genome, e.g., a vaccinia virus WR genome or an MVA genome. In other aspects the poxvirus genome is a fowlpox virus or rabbit pox virus genome. A poxvirus genome comprising a polynucleotide as described can be produced by standard molecular biological and virology techniques, for example by using tri-molecular recombination as described herein. A poxvirus genome as provided herein can be introduced into permissive cells as part of a recombinant poxvirus, or as naked DNA accompanied by suitable helper viruses, e.g., fowlpox virus. The disclosure further provides a recombinant poxvirus, e.g., a recombinant vaccinia virus, fowlpox virus, or rabbit pox virus comprising the provided poxvirus genome.

IMP-EEV Fusion Proteins, Recombinant Poxvirus EEVs, and Methods of Making

This disclosure further provides an IMP-EEV-specific fusion protein such as those encoded by the polynucleotides described above. Moreover, the IMP-EEV-specific fusion protein can be expressed on the surface of a recombinant poxvirus EEV, e.g., a recombinant vaccinia virus EEV, recombinant fowlpox virus or recombinant rabbit pox virus. A recombinant poxvirus EEV, e.g., a recombinant vaccinia virus EEV, fowlpox virus EEV or rabbit pox virus EEV, comprising the provided fusion protein is provided by the disclosure. For example, a vaccinia virus EEV can express an IMP fusion protein comprising an IMP fusion with a fowlpox virus EEV specific protein such as FPV108 or a rabbit pox virus EEV-specific protein such as RBXV041. Similarly, a recombinant fowlpox virus EEV can express on its surface an IMP-EEV-specific fusion protein comprising an IMP fused to a fowlpox virus, vaccinia virus or rabbit pox virus EEV-specific protein.

A recombinant poxvirus EEV can be produced by a method that includes infecting a host cell permissive for vaccinia virus, fowlpox virus or rabbit pox virus infectivity with an appropriate pox virus comprising a poxvirus genome as provided above, and recovering EEV released from the infected host cell. Accordingly, an IMP-pox virus EEV-specific fusion protein encoded by a polynucleotide as described above, is provided.

Moreover the disclosure provides fusion proteins comprising an IMP or fragment thereof, which can be a multi-pass IMP, and single pass IMP, or even just the extracellular domain (ECD) of the IMP, fused to a poxvirus protein, e.g., a vaccinia virus protein, specific for EEV, such as F13L, A56R, or a fowlpox virus protein, specific for EEV, such as FPV108, FPV109, or FPV148, or a rabbit pox virus protein specific for EEV, such as RBXV041, an "IMP-EEV fusion protein." Exemplary ECD fusion proteins are described below. An IMP-EEV fusion protein as provided herein can display the IMP, e.g., a multi-pass IMP, single-pass IMP or ECD of an IMP, in a conformationally intact form on the surface of poxvirus EEV. For use in screening antibody display libraries for antigen binding domains that specifically bind to a target IMP, display of IMPs on the surface of poxvirus EEV offers many advantages over displaying IMPs on the surface of recombinant cells, e.g., CHO cells, as is typical. For example the IMP can be expressed at higher density on EEV than on cells. Moreover, pox virus EEV express only about six or fewer different poxvirus proteins on their surface (e.g., vaccinia virus F13L, A56R, B5R, 33R, A34R, and A36R; fowlpox virus FPV108, FPV109 and FPV148) as opposed to hundreds that might be expressed on the surface of cells. Finally, inactivated EEV expressing IMP-F13L, IMP-FPV108, or RBXV041 fusion proteins as provided herein can be attached to solid supports, offering convenience in library screening.

Accordingly, this disclosure provides a method to display an integral membrane protein (IMP) or fragment thereof in a native conformation for use, e.g., in screening antibody display libraries for antigen binding domains specific for the IMP. The method includes: infecting host cells permissive for poxvirus infectivity with a recombinant poxvirus that expresses the IMP or fragment thereof as a fusion protein with poxvirus EEV-specific protein or membrane-associated fragment thereof, where EEV produced by the infected host cell comprise the IMP as part of the EEV outer envelope membrane; and recovering EEV released from the host cell. IMP. In certain aspects, the EEV-specific protein or fragment thereof can be the vaccinia virus, A56R protein, F13L protein, any membrane-associated fragment thereof, or any combination thereof, or FPV 108, FPV109, or FPV148 or RBXV041 protein, any membrane-associated fragment thereof, or any combination thereof.

In certain aspects, the EEV-specific protein is F13L (SEQ ID NO: 1) or a functional fragment thereof, or FPV108 (SEQ ID NO: 2) or a functional fragment thereof, or RBXV041 (SEQ ID NO: 3) or a functional fragment thereof and the fusion protein can be one expressed by a polynucleotide as provided above, e.g., where the IMP is a multi-pass membrane protein comprising at least two, at least three, at least four, at least five, at least six or at least seven transmembrane domains.

In certain aspects, the membrane-associated EEV specific protein fragment includes the stalk, transmembrane, and intra-membrane domains of the vaccinia virus A56R protein, a fragment comprising, consisting of, or consisting essentially of amino acids 108 to 314 of SEQ ID NO: 5. One of several exemplary fusion partners includes the ECD of human FZD4, shown in bold in SEQ ID NO: 12 below. According to this exemplary aspect the disclosure provides a method to display a conformationally intact fragment of human FZD4 on the surface of a poxvirus EEV comprising infecting host cells permissive for poxvirus infectivity with a recombinant poxvirus encoding a fusion protein comprising amino acids 20 to 370 of SEQ ID NO: 12. In certain aspects the fusion protein can further comprise a signal peptide, e.g., amino acids 1 to 19 of SEQ ID NO: 12.

>FZD-ECD-A56R
(Seq ID NO: 12)
MGWSCIILFLVATATGAHSFGDEEERRCDPIRISMCQNLGYNVTKMPNLV

GHELQTDAELQLTTFTPLIQYGCSSQLQFFLCSVYVPMCTEKINIPIGPC

GGMCLSVKRRCEPVIKEFGFAWPESLNCSKFPPQNDHNHMCMEGPGDEEV

PLPHKTPIQPGEE_TSTTNDTDKVDYEEYSTELIVNTDSESTIDIILSGST_

_HSPETSSKKPDYIDNSNCSSVFEIATPEPITDNVEDHTDTVTYTSDSINT_

_VSASSGESTTDETPEPITDKEDHTVTDTVSYTTVSTSSGIVTTKSTTDDA_

_DLYDTYNDNDTVPPTTVGGSTTSISNYKTKDFVEIFGITALIILSAVAIF_

_CITYYIYNKRSRKYKTENKV_.
Single Underline - leader peptide (amino acids 1-19)
Bold - human FZD4 extracellular domain (amino acids 20-163)
Italics - A56R stalk, transmembrane, and intra-membrane (amino acids 164 to 370)

Another exemplary fusion partner includes the ECD of human ErbB2 (Her2), shown in bold in SEQ ID NO: 7 below. According to this exemplary aspect the disclosure provides a method to display a conformationally intact fragment of human Her2 on the surface of a poxvirus EEV comprising infecting host cells permissive for poxvirus infectivity with a recombinant poxvirus encoding a fusion protein comprising amino acids 20 to 855 of SEQ ID NO: 7. In certain aspects the fusion protein can further comprise a signal peptide, e.g., amino acids 1 to 19 of SEQ ID NO: 7.

>Her2-A56R (SEQ ID NO: 7)

MGWSCIILFLVATATGAHSSTQVCTGTDMKLRLPASPETHLDMLRHLYQG

CQVVQGNLELTYLPTNASLSFLQDIQEVQGYVLIAHNQVRQVPLQRLRIV

RGTQLFEDNYALAVLDNGDPLNNTTPVTGASPGGLRELQLRSLTEILKGG

VLIQRNPQLCYQDTILWKDIFHKNNQLALTLIDTNRSRACHPCSPMCKGS

RCWGESSEDCQSLTRTVCAGGCARCKGPLPTDCCHEQCAAGCTGPKHSDC

LACLHFNHSGICELHCPALVTYNTDTFESMPNPEGRYTFGASCVTACPYN

YLSTDVGSCTLVCPLHNQEVTAEDGTQRCEKCSKPCARVCYGLGMEHLRE

VRAVTSANIQEFAGCKKIFGSLAFLPESFDGDPASNTAPLQPEQLQVFET

LEEITGYLYISAWPDSLPDLSVFQNLQVIRGRILHNGAYSLTLQGLGISW

LGLRSLRELGSGLALIHHNTHLCFVHTVPWDQLFRNPHQALLHTANRPED

ECVGEGLACHQLCARGHCWGPGPTQCVNCSQFLRGQECVEECRVLQGLPR

EYVNARHCLPCHPECQPQNGSVTCFGPEADQCVACAHYKDPPFCVARCPS

GVKPDLSYMPIWKFPDEEGACQPCPINCTHSCVDLDDKGCPAEQRASP*TS*

*TTNDTDKVDYEEYSTELIVNTDSESTIDIILSGSTHSPETSSKKFDYIDN*

*SNCSSVFEIATPEPITDNVEDHTDTVTYTSDSINTVSASSGESTTDETPE*

*PITDKEDHTVTDTVSYTTVSTSSGIVTTKSTTDDADLYDTYNDNDTVPPT*

*TVGGSTTSISNYKTKDFVEIFGITALIILSAVAIFCITYYIYNKRSRKYK*

*TENKV.*

Single Underline - leader peptide (amino acids 1-19)
Bold - human ERBB2 (HER2) extracellular domain (amino acids 20-648)
Italics - A56R stalk, transmembrane, and intra-membrane (amino acids 649 to 855)

Another exemplary fusion partner includes the ECD of human CD100 (Semaphorin 4D), shown in bold in SEQ ID NO: 8 below. According to this exemplary aspect the disclosure provides a method to display a conformationally intact fragment of human CD100 on the surface of a poxvirus EEV comprising infecting host cells permissive for poxvirus infectivity with a recombinant poxvirus encoding a fusion protein comprising amino acids 20 to 935 of SEQ ID NO: 8. In certain aspects the fusion protein can further comprise a signal peptide, e.g., amino acids 1 to 19 of SEQ ID NO: 8.

>CD100-A56R (SEQ ID NO: 8)

MGWSCIILFLVATATGAHSFAPIPRITWEHREVHLVQFHEPDIYNYSALL

LSEDKDTLYIGAREAVFAVNALNISEKQHEVYWKVSEDKKAKCAEKGKSK

QTECLNYIRVLQPLSATSLYVCGTNAFQPACDHLNLTSFKFLGKNEDGKG

RCPFDPAHSYTSVMVDGELYSGTSYNFLGSEPIISRNSSHSPLRTEYAIP

WLNEPSFVFADVIRKSPDSPDGEDDRVYFFFTEVSVEYEFVFRVLIPRIA

RVCKGDQGGLRTLQKKWTSFLKARLICSRPDSGLVFNVLRDVFVLRSPGL

KVPVFYALFTPQLNNVGLSAVCAYNLSTAEEVFSHGKYMQSTTVEQSHTK

WVRYNGPVPKPRPGACIDSEARAANYTSSLNLPDKTLQFVKDHPLMDDSV

TPIDNRPRLIKKDVNYTQIVVDRTQALDGTVYDVMFVSTDRGALHKAISL

EHAVHIIEETQLFQDFEPVQTLLLSSKKGNRFVYAGSNSGVVQAPLAFCG

KHGTCEDCVLARDPYCAWSPPTATCVALHQTESPSRGLIQEMSGDASVCP

DKSKGSYRQHFFKHGGTAELKCSQKSNLARVFWKFQNGVLKAESPKYGLM

GRKNLLIFNLSEGDSGVYQCLSEERVKNKTVFQVVAKHVLEVKVVPKPVV

APTLSVVQTEGSRIATKVLVASTQGSSPPTPAVQATSSGAITLPPKPAPT

GTSCEPKIVINTVPQLHSEKTMYLKSSD*TSTTNDTDKVDYEEYSTELIVN*

*TDSESTIDIILSGSTHSPETSSKKPDYIDNSNCSSVFEIATPEPITDNVE*

*DHTDTVTYTSDSINTVSASSGESTTDETPEPITDKEDHTVTDTVSYTTVS*

*TSSGIVTTKSTTDDADLYDTYNDNDTVPPTTVGGSTTSISNYKTKDFVEI*

*FGITALIILSAVAIFCITYYIYNKRSRKYKTENKV.*

Single Underline - leader peptide (amino acids 1-19)
Bold - human CD100 extracellular domain (amino acids 20-728)
Italics - A56R stalk, transmembrane, and intra-membrane (amino acids 729 to 935)

The disclosure further provides a fusion protein comprising: amino acids 20 to 892 of SEQ ID NO: 4; SEQ ID NO: 9; SEQ ID NO: 4; amino acids 20 to 370 of SEQ ID NO: 12; amino acids 20 to 935 of SEQ ID NO: 8; any combination thereof, any fragment thereof, or any variant thereof, where the fusion protein, when expressed by a recombinant fowlpox virus, appears on the surface of the fowlpox virus extracellular enveloped virion (EEV) in a native conformation.

A recombinant poxvirus EEV, such as a recombinant fowlpox virus or recombinant rabbit pox virus comprising any EEV fusion protein as provided herein is also provided.

Method of Selecting Antibodies

This disclosure further provides a method to select binding molecules, e.g., antibodies, antigen-binding antibody fragments, or antibody like binding molecules that bind to a multi-pass membrane protein interest. The method comprises generating a first and second recombinant poxvirus EEV using a recombinant poxvirus genome as described herein, wherein the first and second recombinant poxvirus EEV are each generated in a different poxvirus, e.g., vaccinia virus and fowlpox virus polypeptides that encode the same IMP on a fusion protein. Each of the resulting recombinant poxvirus EEVs expresses the IMP in native form on its surface. The first recombinant poxvirus EEV is used to immunize a mammal, e.g., a mouse. A display library that displays a plurality of antigen binding domains is then generated from B cells isolated from the immunized mammal and contacted with the second recombinant poxvirus EEV which is attached to a solid support so that display packages that specifically bind to the IMP expressed on the second recombinant poxvirus EEV can bind thereto. Any unbound display packages are then removed and display packages that display an antigen binding domain specific for the IMP expressed on the second recombinant EEV are recovered. Because vaccinia virus and fowlpox virus are antigenically distinct, any antibodies that recognize and bind to the virus rather than the IMP are thus eliminated.

Any display library generated from B cells isolated from the immunized mammal that comprise a plurality of binding domains, e.g., antibodies, antibody-like molecules or other binding molecules is suitable for this method. For example, the display library can be a phage display library, a yeast display library or a library constructed in a vaccinia virus vector or a fowlpox virus vector as described elsewhere herein.

In certain aspects, the second recombinant EEV can be inactivated prior to attachment to the solid support. For example, the EEV can be inactivated by incubation with Psoralen (Trioxsalen, 4'-aminomethyl-, hydrochloride) in the presence of UV irradiation.

Any suitable solid support can be used. As used herein, a "solid support" is any support capable of binding an EEV, which can be in any of various forms, as is known in the art. Well-known supports include tissue culture plastic, glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of this disclosure. The support material can have virtually any structural configuration as long as the coupled EEV is capable of binding to a displayed binding molecule such as an antibody. Thus, the support configuration can be spherical, as in a bead, or cylindrical, as in the inside surface of a test tube, or the external surface of a rod. Alternatively, the surface can be flat such as a sheet, test strip, etc. Typical supports include beads, e.g., magnetic polystyrene beads such as DYNABEADS® that can be pulled out of suspension by a magnet. The support configuration can include a tube, bead, microbead, well, plate, tissue culture plate, petri plate, microplate, microtiter plate, flask, stick, strip, vial, paddle, etc., etc. A solid support can be magnetic or non-magnetic. Those skilled in the art will know many other suitable carriers for binding EEV as provided herein, or will be able to readily ascertain the same. In certain aspects, EEV as provided herein can be attached to the solid support via reaction with, e.g., tosyl groups, epoxy groups, carboxylic acid groups, or amino groups attached to the surface. For example, EEV can be attached to the surface of tosyl-activated magnetic beads, e.g., MYONE™ tosylactivated beads. Alternatively, the EEV can be biotinylated and attached to a streptavidin solid surface, e.g., streptavidin coated magnetic beads.

In another aspect, the disclosure provides an animal-based system for selecting binding molecules, e.g., antibodies, antigen-binding antibody fragments, or antibody like binding molecules that bind to a multi-pass membrane protein of interest. The method comprises immunizing a mammal, e.g., a mouse with a recombinant poxvirus EEV as described herein that expresses the IMP of interest in native form on its surface. Immunization can be by any route, e.g., intraperitoneal injection. The immunized mammal can be administered one or more booster dosages of the recombinant poxvirus EEV to enhance production of antibodies to the IMP. An optional first booster dose can be administered within five to fourteen days following the first immunization dose, such as at five days, six days, seven days, eight days, nine days, ten days, eleven days, thirteen days or fourteen days or more following administration of the first immunization dose. An optional second booster dose can be administered within one week to two weeks following the first booster dose. The immunized animal can be bled at various times after the first immunization or post-boost to test for the presence of anti-IMP antigen binding molecules, for example by flow cytometry on cells expressing the antigen of interest. Anti-IMP antigen-binding molecules are isolated from immunized animal serum as described herein above.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; H. Freeman & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties. The following examples are offered by way of illustration and not by way of limitation.

Examples Example 1: Fusion Protein Construction

IMPs were incorporated into poxvirus EEVs using the EEV-specific proteins F13L, A56R, and FPV108, by the following methods. Generally, the extracellular domains of HER2, CD100 (semaphorin 4D), and FZD4 were incorporated as fusions with the single-pass EEV-specific membrane protein A56R as diagrammed in FIG. 1A. The mature FZD4-ECD-A56R fusion protein comprises amino acids 20 to 370 of SEQ ID NO: 12, the mature HER2-ECD-A56R fusion protein comprises amino acids 20 to 855 of SEQ ID NO: 7, and the mature CD100-ECD-A56R fusion protein comprises amino acids 20 to 935 SEQ ID NO: 8. The mature CD100-ECD-A56R fusion protein comprises amino acids 20 to 935 SEQ ID NO: 8. FIG. 1B and FIG. 1C show diagrammatically how the multi-pass proteins such as GPCRs, CD39 and CD20 can be incorporated into EEVs as multi-pass membrane proteins as a fusion with the EEV membrane-associated protein F13L, FPV108, or RBXV041.

IMPs were incorporated into fowlpox virus EEVs using the EEV-specific protein FPV108 or VV A56R by the following methods. QT35 cells in 6-well plate were infected with FPV at MOI 1.5 for 2 hours and then transfected with the FPV transfer vector H5-FPV-CD100-A56R-Iresneo, H5-FPV-CD20-FPV108-IresNeo or H5-FPV-muCD39-FPV108-IresNeo. After 48 hours, virus was harvested and titered. The bulk virus was used to infect QT35 cells in 6-well plate overnight than the cells were stained with antigen specific antibody and sorted. Virus was extracted from the sorted cells by freeze/thaw and amplified for 3-4 days in QT35 cells and titered for a $2^{nd}$ or $3^{rd}$ sort. After 2 or 3 rounds of sorting, the sorted virus was amplified and plated for plaque picking. Amplified plaques were PCR checked with vector specific and gene specific primers. Clones with mixed inserts were picked and further plaqued out for additional rounds until only the correct inserts remained.

FPV was also generated by Pseudotyping using Stable Cell line. QT35 cells were transfected using lipofectamine with a mammalian expression vector encoding either Sema-A56 or CD20-FPV108. Both vectors also have G418 resistance. After drug selection, cells were sorted for surface expression of Sema4D or CD20 and expanded. Antigen expressing cells were seeded into 6 well plates or T175 flasks and infected with FPV. After 48 hours the EEV in the supernatant was harvested and the FPV was tested for antigen incorporation using pulldown assay.

Antigen incorporation into FPV was also done by infection/transfection. Infection/transfection: QT35 cells in 6 well plates were infected at moi=1 with FPV. Two hours later the cells were washed and then transfected using lipofectamine with a vaccinia transfer plasmid where expression of Sema ECD-A56 is controlled by the vaccinia H5 promoter. Two days following transfection the EEV was harvested from the cell supernatant and tested in a pulldown assay using anti-SEMA4D mab conjugated to ProG beads.

FZD4, CD20 and CD39 were incorporated into fowlpox EEVs and/or vaccinia virus EEVs as multi-pass membrane fusions with FPV108 and/or F13L and Sema-ECD was incorporated into fowlpox EEV and vaccinia virus and MVA EEVs as single-pass membrane fusions with A56R.

Protein G Dynabeads (ThermoFisher) were mixed by vortexing and the needed volume (25 ul per sample) was dispensed into 1 ml Phosphate Buffered Saline (PBS) in a 1.2 ml screw cap tube. The tubes were place on the Dynal magnet (ThermoFisher) and the bead were allowed to pellet. The supernatant was removed, and the beads were washed once in 1 ml of PBS. The beads were then resuspended in 0.5 ml of PBS with anti-antigen antibodies (5 μg of antibody per 25 μl of beads) and mixed. The beads were allowed to rotate at room temperature for one hour to couple the antibody to the magnetic bead. The beads were then washed using the Dynal magnet twice with 1 ml of PBS and then resuspended in 25 μl of PBS per 25 μl of initial bead volume. EEV samples were either used neat (supernatant) or diluted to approximately $2\times10^6$ pfu/ml in EMEM+10% FBS. The antibody-coupled beads were then rotated at room temperature for an hour to facilitate antibody capture of the antigen expressing virus. Positive and negative control combinations were included where possible. The beads were then washed five times with 1 ml of EMEM+10% FBS, and the supernatant from each wash was pooled together as the unbound fraction. The bound fraction (beads+virus) were resuspended in 1 ml of EMEM+10% FBS. Both the bound and unbound fractions were titered by serial dilution in media and then an aliquot was overlaid in duplicate on monolayers of cells (BHK for MVA, QT35 for FPV, BSC-1 for VV) and allowed to infect for 3-4 days. The cells were then stained with 0.1% Crystal Violet in 20% ethanol and plaques were counted. The titer of the unbound solution was multiplied by its volume (6 ml) and the bound percentage was calculated as a function of the total virus. The negative control bound percentage was subtracted from this value to give the specific antigen bound percentage.

Pulldown data for the various constructs is shown in FIG. 6 (FZD-F13L and QT35-FZD4-FPV108); FIG. 7 (CD20-F13L, CD20-FPV108 and QT35-CD20-FPV108); FIG. 8 (CD39-GFP-F13L; CD39-F13L; CD39-FPV108); and FIG. 9 (Sema-ECD-A56R and QT-Sema-A56R), demonstrating that the construct is incorporated into the virus membrane and the IMP is expressed on the envelope surface.

Preparation of FPV108 Fusion Proteins (CD20, CD39, FZD4).

F13L Fusion Proteins (FZD4-F13L, CD20-F13L, and CXCR4-F13L) were generated as described in U.S. Pat. No. 10,577,427, which is incorporated herein in its entirety by reference.

Preparation of FPV108 Fusion Proteins (CD20 and CD39)

Genes or gene fragments were inserted in-frame into FPV using standard homologous recombination methods. The gene or gene fragment of interest, e.g., CD20 or CD39 was inserted between FPV genes 086 and 087 at a Nco/Xho I site and was tagged with FPV108. The CD20 gene was modified at the 5' end to accommodate an NCO I restriction site. Modification of the CD39 gene was not required. The Nco/Xho I sites are flanked by homologous recombination sites comprising the FPV left arm (FPV 084, 085, and 086) and FPV right arm (FPV 087 and 088), as well as an Internal Ribosome Entry Site (IRES) element and neomycin resistance gene (NEO) to allow co-expression of the gene of interest or fragment thereof and the FPV108 gene genes under control of the same promoter and allows for clone selection (NEO resistance). The vector map for FPV is shown in FIG. 2. The resulting CD20-FPV108 and CD39-FPV108 fusion proteins are shown above (SEQ ID NO: 10 and SEQ ID NO: 11, respectively).

Example 2: Expression of CD20-FPV108 and CD39-FPV108 Fusion Protein on EEV

QT35 cells were infected with either IMV encoding the CD20-FPV fusion protein (SEQ ID NO: 10) or the CD39-FPV108 fusion protein (SEQ ID NO: 11) or Control fowlpox virus at a multiplicity of infection (MOI) of 1 virus per cell for two days after which the supernatant containing EEV was harvested and debris removed by low speed centrifugation. Protein G DYNABEADS® (110 μL) were pulled down with a magnet and 1 mL of PBS+20 µg of purified anti-CD20 antibody or anti-CD39 antibody as appropriate was added to the beads. The solution was incubated at room temperature with gentle rotation for 30-60 minutes to allow the antibody to couple to the Protein G beads. Ten µg of purified mIgG1 isotype control was added to the solution to ensure complete blocking, and the solution was incubated at room temperature with gentle rotation for 10-30 additional minutes. Beads were pulled down with the magnet, washed once with 1 mL of PBS and resuspended in 110 µL of PBS.

Fifty µL of Anti-CD20-Protein G DYNABEADS® or Anti-CD39-Protein G DYNABEADS® was added to 1 mL of CD20-F13L or control fowlpox EEV supernatant and was incubated at room temperature with gentle rotation for 1 hour. Beads were pelleted using the magnet and unbound supernatant removed. The beads were then washed five times with 1 mL of Dulbecco's Modified Eagle Medium (DMEM) media supplemented with 10% FBS and 1 mM HEPES (10% DMEM). All washes were pooled with the unbound supernatant ("Unbound"). The beads ("Bound") were then resuspended in 1 mL of 10% DMEM. "Unbound" and "Bound" were titered on QT35 cells and overlaid with growth medium containing methylcellulose. Plaques were allowed to form for two days and then the cells were fixed and stained with 0.1% Crystal Violet solution. Plaques were counted to determine the number of plaque forming units (pfu) in the "Unbound" and "Bound" from which the % of EEV bound to the beads could be calculated. The % EEV bound to the anti-CD20 and anti-CD39 coated beads was significantly higher for CD20-FPV108 and CD39-FPV108 EEV fusion proteins than it is for the fowlpox virus control indicating that CD20 and CD39 are being expressed on the EEV membrane surface.

Example 3: Antigen Incorporation into Fowlpox Virus

Infection/transfection: QT35 cells were infected at a moi of 1 with FPV expressing the following antigen constructs: CD20-FPV108 (SEQ ID NO: 10, CD39-FPX108 (SEQ ID NO: 11), and FZD4-FPV108 (SEQ ID NO: 4). After two hours the cells were washed and then transfected using lipofectamine with a vaccinia transfer plasmid in which expression of Sema ECD-A56 is controlled by the vaccinia H5 promoter. Two days following transfection the EEV were harvested from the cell supernatant and tested in a pulldown assay using anti-SEMA-4D mab conjugated to ProG beads.

Pull down assay and titer of EEVs expressing antigens: Protein G Dynabeads (ThermoFisher) were mixed by vortexing and 25 µl per sample was dispensed into 1 ml Phosphate Buffered Saline (PBS) in a 1.2 ml screw cap tube. The tubes were place on a Dynal magnet (ThermoFisher) and the beads were left to pellet for 2 min. The supernatant was removed, and the beads were washed once in 1 ml of PBS. The beads were then resuspended in 0.5 ml of PBS with anti-antigen antibodies (5 µg of antibody per 25 µl of beads) and mixed. The beads were allowed to rotate at room temperature for one hour to couple the antibody to the magnetic bead. The beads were then washed twice using a Dynal magnet with 1 ml of PBS and then resuspended in 25 µl of PBS per 25 µl of initial bead volume. EEV samples were either used neat (supernatant) or diluted to approximately $2 \times 10^6$ pfu/ml in M199+10% FBS. The antibody-coupled beads were added to EEV samples and rotated at room temperature for an hour to facilitate antibody capture of the antigen expressing virus. Positive and negative control combinations were included where possible. The beads were then washed five times with 1 ml of M199+10% FBS, and the supernatant from each wash was pooled together as the unbound fraction. The bound fraction (beads+virus) was resuspended in 1 ml of M199+10% FBS. Both the bound and unbound fractions were titered by serial dilution in media and then an aliquot was dispensed in duplicate on monolayers of cells (QT35 for FPV) and allowed to infect for 1-2 hours. The cells were overlaid with growth media containing 0.5% methyl cellulose and incubated for 3-4 days at 37° C., 7% $CO_2$. The viral plaques were counted by staining cells with 0.1% Crystal Violet in 20% ethanol. The titer of the unbound solution was multiplied by its volume (6 ml) and the bound percentage was calculated as a function of the total virus. The % bound for the negative control was subtracted from the % bound of the sample to give the specific antigen bound percentage.

Generation of QT35 stable transfectants for pseudotype virus production: QT35 cells were seeded into 6 well plates and allowed to grow until they were ~80% confluent. Cells were transfected using Lipofectamine 2000 reagent as per the manufacturer's instructions, one well per mammalian expression vector construct. Empty vector and No Vector were included as controls. The following day, the cells were harvested and dispensed into a T175 flask with QT35 medium containing G418 for drug selection (QT35 medium: M199 medium, 10% FBS, 5% Tryptose-Phosphate Broth, 1 mM HEPES, 2 mM L-Glutamine, 0.08 mg/ml G418). Media containing drug was changed every 2-3 days to maintain selection pressure. When the No Vector cells had died off, the transfectants were stained using anti-antigen antibodies for Fluorescence Activated Cell Sorting (FACS) on a BD FACS Aria sorter. Cells with high antigen expression were collected, cultured and post-sort enrichment was determined by flow cytometry. A second sort was performed to further enrich for high antigen expression.

Incorporation of antigen into the virus membrane or QT35 cell membrane using the constructs described above is shown in FIGS. 6-12. The histograms shown in FIGS. 10 and 11 show incorporation of the constructs into the cell membrane based on infection (FIGS. 10 & 11) or the QT35 transfection for pseudotype (FIG. 12). The pull down bar graphs in FIGS. 6-9 show the incorporation into the EEV membrane.

Pseudotyping using a stable cell line: QT35 cells were transfected using lipofectamine with mammalian expression vector either Sema-A56, FZD4-FPV108, or CD20-FPV108. All vectors also have G418 resistance (conferred by the Neo gene). After drug selection, cells were sorted for surface expression of Sema-4D, FZD4, or CD20 and expanded. Antigen expressing cells were seeded into well plates or T175 flasks and infected with FPV at a moi of 1. After 48 hours the EEV in the supernatant was harvested and FPV was tested for antigen incorporation using a pulldown assay as described above Generation of FPV recombinants: QT35 were infected with FPV at a MOI of 1.5 for two hours and then transfected with the FPV transfer vector H5-HPV-CD-A56R-IresNeo, H5-FPV-CD20-FPV108-IresNeo or H5-FPV-muCD39-FPV108-IresNeo. After 48 hours, virus was harvested and titered.

The bulk virus was used to infect QT35 cells overnight. The cells were stained with antigen-specific antibody and sorted. FPV was extracted from the sorted cells by freeze/thaw and amplified for 3 to 4 days in QT35 cells and titered for a second or third sorting. After 2 or 3 rounds of sorting, the sorted virus was amplified and plated for plaque picking. Amplified plaques were checked by PCR using vector-specific and gene-specific primers. Clones with mixed inserts were selected and further plated for additional rounds until only the correct inserts remained.

Flow cytometry to analyze cell surface expression of QT35 stable transfectants for pseudotype virus generation: QT35 stable cell lines were harvested using Accutase, counted, pelleted, and resuspended at 2 million cells per mL in FACS Buffer (lx PBS, 1% BSA and 2 mM EDTA). Fifty microliters (100,000 cells) was dispensed into each well of a 96 well V-bottom plate. Fifty microliters of anti-antigen antibody was added to each well to give a final concentration of 5 ug/ml of antibody in FACS buffer. The antibody and cells were incubated on ice for one hour. Cells were pelleted and then resuspended in FACS Buffer containing anti-Human-Fc-APC antibody (Biolegend) and incubated on ice for 30 minutes. Cells were pelleted again, washed with FACS Buffer and fixed with 0.5% paraformaldehyde in FACS Buffer before running on the BD FACS Canto II with propidium iodide for live/dead discrimination. APC histograms were plotted from the PI negative (live) cell population. The results are shown in FIGS. 10-12, discussed below.

Flow cytometry to analyze cell surface expression of FPV recombinants as compared to MVA: QT35 cells were seeded overnight in 6 well tissue culture plates and the following day were infected with either FPV or MVA constructs (IMV) at a multiplicity of infection (MOI) of one virus per cell. The virus was allowed to infect overnight at 37 C, 7% $CO_2$. The next morning, cells were harvested using Accutase, pelleted, and washed with 5 ml of FACS Buffer (lx PBS, 1% BSA and 2 mM EDTA). Each well of cells was then resuspended in 200 µl of FACS Buffer and 50 µl was dispensed into each well of a 96 well V-bottom plate. Fifty microliters of anti-antigen antibody were added to each well to give a final concentration of 5 ug/ml of antibody in FACS buffer. The antibody and cells were incubated on ice for one hour. Cells were pelleted and then resuspended in FACS Buffer containing anti-Human-Fc-APC antibody (Biolegend) and incubated on ice for 30 minutes. Cells were pelleted again, washed with FACS Buffer and fixed with 0.5% paraformaldehyde in FACS Buffer before running on the BD FACS Canto II with propidium iodide for live/dead discrimination. APC histograms were plotted from the PI negative (live) cell population.

FIGS. 10 and 11 demonstrate that expression of the IMP (CD20 and CD39) in fowlpox using a CD20-FPV108 and FPV-H5-muCD39-FPV108 construct, respectively) is similar to that of the control (MVA-T7-CD20-G-F and MVA-HA-56-muCD39-F, respectively in MVA). FIG. 12 shows expression of CD20, FZD4, and SEMA4D, respectively on the cell surface of QT35 cells transfected with a CD20-FPV108 (FIG. 12A), FZD4-FPV108 (FIG. 12B) and SEMA4D-A56R (FIG. 12C) construct.

Example 4

Example 4: Alternate Immunization and Panning with Vaccinia Virus and FPV to Eliminate Anti-Virus Antibody Responses to Immunization Immunization With either a recombinant vaccinia or fowlpox virus strain generates very potent antibody responses to the recombinant antigen. Animals are immunized with recombinant poxvirus, e.g., recombinant vaccinia or fowlpox virus, and a display library is generated from the B cells isolated from the immunized animals. The display library generated from the immunized animals is then "panned" or "screened" on antigen displayed on a distinct recombinant pox virus, e.g. fowlpox or vaccinia virus/MVA, as appropriate. This facilitates selection against the antigen of interest by eliminating anti-vector antibodies. Using this approach, up to one billion antibody combinations have been screened in vitro and have been cloned, and sequenced. Including immunization time, screening and verification, the entire process is completed in about 2 months.

Immunization

Female BALB/c mice (Jackson; 8 weeks old) were bled before immunization to provide baseline titer. At 9 weeks old (Day 0), mice were immunized with $10^7$ pfu of EEV intraperitoneally, using a minimum of 3 mice per group. Mice were bled on Day 21 post immunization and boosted with a second dose of EEV as on Day 0. Mice were bled at various time points post boost, and all serum was isolated by centrifugation at 13,000 rpm for 3 minutes using BD Microtainer SST tubes to pellet the red blood cells. The serum was removed and frozen in a fresh tube with each mouse remaining separate. In some instances, mice were boosted a second time with EEV to increase response.

Figure 13:
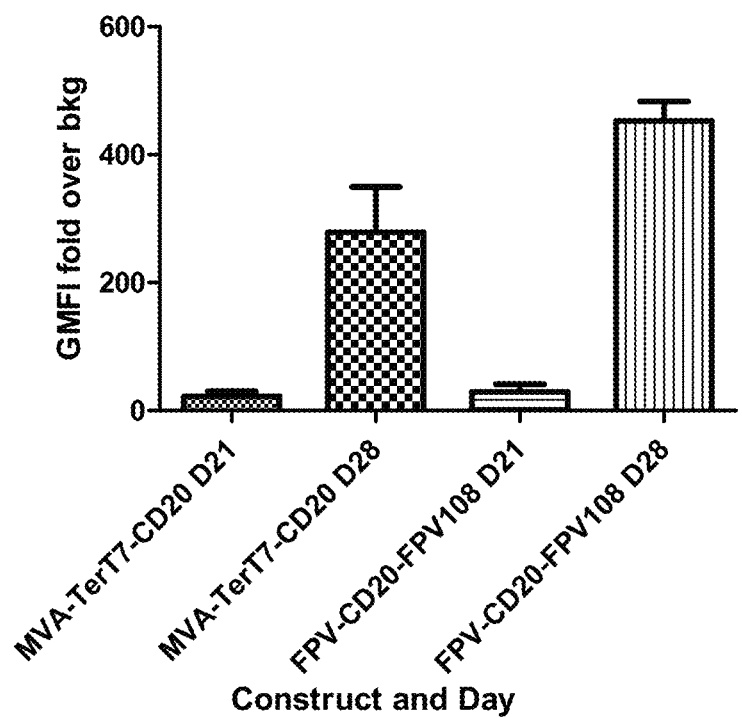

To analyze the serum for the presence of mouse anti-CD20 antibodies, each serum sample was serially diluted in FACS Buffer (lx PBS, 1% BSA and 2 mM EDTA) and tested for mouse anti-antigen binding by flow cytometry on cells expressing the antigen of interest followed by anti-Mouse-APC secondary detection reagent. The GMFI for each sample was divided by the GMFI for anti-Mouse-APC alone to calculate the fold over background. Values for mice in the same group and day were averaged and plotted along with the standard deviation. As shown in FIG. 13, the mice mount a response after administration of the first dose, which is enhanced after the second immunization dose.

As shown in FIG. 13 immunization with either MVA/CD20 or FPV/CD20 resulted in serum antibody titers that demonstrated binding to CD20+Wil2S cells.

Generation of Phage Display Library from Immunized Mice B Cells

Bone marrow and spleen were harvested from immunized mice and stored in RNAlater™ (ThermoFisher cat #AM7020). RNA was extracted using RNAeasy kit (Qiagen), DNAse-treated and quantified by nanodrop. cDNA was prepared using standard protocols followed by RNAase treatment. For cDNA synthesis, the cDNA was primed using primers specific to the constant domain of mouse gamma constant 1 and constant 2 gene. This selected for antibodies in activated B cells. Heavy chain variable regions were PCR amplified using standard methods and utilizing a mix of mouse VH gene and JH gene primer containing BssHII and BsteII restriction sites. The PCR product was gel purified. V-genes were bulk cloned into a phagemid pool (pAD) at the BssHII/BsteII sites (pAD phagemid backbone in the pool containing 21 human germline variable light chains fused to human constant regions separated by a Ribosome Binding site (RBS)) using NxGen T4 DNA Ligase, Lucigen 3024-1. Ligation reactions were transformed via electroporation into TG1 Electrocompetent cells, Lucigen #60502-2, with 1 hr outgrowth and expanded culture at 37° C. for 5 hours with shaking in 2YXT buffer with glucose and ampicillin. Phagemid library was harvested by centrifugation at 4° C., 6200 rpm for 15 minutes. Pellets were re-suspended in freezing media (containing 2XYT, glycerol, glucose and Amp). Bacteria were plated to titer the library and a subset of phagemid were mini-prepped and sequenced for library quality control.

To generate phage, the library was grown to log phase in 2XYT/Ampicillin/glucose.

and then infected with hyperphage for 1 hour at 37° C., after which the cells were pelleted by centrifugation and resuspended in 2XYT/Amp/Kanamycin and grown with shaking at 300 overnight. The following day the phage were harvested by PEG precipitation and resuspended in 1 ml PBS.

For library panning, Tosylactivated MyOne DYNABEADS® (100 μL) were pulled down with a magnet and washed with 1 mL of PBS, two times. The beads were pulled down with the magnet, the PBS removed and the 3×10$^8$ pfu of FPV/CD20-FPV108 or control FPV were each added to 50 μl of beads. The beads and antigen-EEV were allowed to rotate at 37° C. for 18-20 hours. The beads were pelleted and the supernatant was removed. The beads were blocked with 1 mL of 1×PBS, 10% FBS and 0.5% BSA at 37° C. for 2 hours. The beads were pelleted and washed with 1 mL 1×PBS before being resuspended in 100 μL of 1×PBS for CD20 and 150 μl for the control FPV. The phage library (1 ml, approximately 10$^{11}$ pfu) generated from the CD20 immunized mice was blocked with 2% milk and 10% FBS for 30 minutes. The phage library was added to 50 μl beads couple with control FPV for 30 min to deplete background and any anti-FPV binding. The beads were pulled down with a magnet and unbound phage was transfer to a fresh tube with a fresh 50 μl of beads coated with control FPV. The phage were allowed to bind for 30 minutes; unbound phage was removed as above and bound to control FPV/beads for a third time for 30 minutes. Unbound phage was then transferred to a fresh tube and the CD20 FPV/bead was added. Phage were bound for 1 hour at RT with rotation. Unbound phage were removed by 10×1 ml washes in PBS/10% FBS and bound phage used to infect log phase TG1 cells in 2XYT/glucose for 1 hour at 370 with shaking. After the 1 hour, hyperphage and ampicillin were added and the cells were grown with shaking at 370 for 1 hour. After an hour the cells were pelleted by centrifugation and resuspended in 2XYT/Amp/Kanamycin and grown with shaking at 300 overnight to produce phage. The next day the phage were harvested by PEG precipitation and resuspended in 1 ml PBS. The phage were then subjected to two additional rounds of panning as described above. After the third round of panning the Tg1 cells were infected for 1 hour and then grown overnight at 300 in 2XYT/Amp/Glucose to expand the plasmid.

The following day, the TG1 cells with the Rd 3 panned phagemid were centrifuged to pellet and then plasmid DNA was extracted (Qiagen HiSpeed Maxiprep kit, cat #12662). Expression cassette containing the linked heavy and light chains (variable light/constant light-RBS element-Variable Heavy) was subcloned as a pool into mammalian expression dual gene vector pEFDGV (Kan) using BsrG1 and NheI restriction sites and standard ligation and transformation protocols (pEFDGV contains the heavy constant to complete the antibody cassette upon cloning) The library was plated on 4 standard 150 mm LB AGAR plates containing 50 mg/mL Kanamycin (LB-Kan50) and incubated overnight at 37° C. A control 'vector only' plate was included. Colonies were counted and background was determined. Approximately 5000 colonies were harvested from the plates (10 ML LB/Glycerol per plate was applied to each plate and colonies were gently lifted from the agar surface using a sterile cell scraper) and plasmid DNA was extracted using Qiagen plasmid DNA kit. This pool was subsequently digested with SalI/BssHI to remove the RBS element and replace it with an IRES element for mammalian co-expression. Transformations were plated on 100 mm LB-Kan50 plates at various densities to ensure good colony separation and incubated overnight at 37° C. 94 colonies were picked into a 96 well deep well growth plate containing 1.6 mL/well LB/Kan50 and grown for 22 hrs at 37° C. A spot plate was arrayed to allow for future propagation of each individual clone in the future. Plasmid DNA was isolated in this format using the Qiagen turbo 96 kit. DNA concentration was measured by nanodrop and averaged to assign a single plate concentration and the DNA was handed off for transfection.

DNA was sequenced at Genewiz using two primers—Ef1F forward primer (5'-TGGAATTTGCCCTTTTTGAG-3') (SEQ ID NO: 13) for the light chain variable region and cGS reverse primer (5' AAGTAGTCCTTGACCAGGCAGCC-3') (SEQ ID NO: 14) for the heavy chain variable region.

For transfection, CHO-S cells were seeded at 50,000 cells per well in a 96 well plate the day before transfection in 125 μl DMEM-10% FBS. The following day 75 μl of a mixture of Lipofectamine 2000 (1.65 μl each well) and Optimem was added to 0.8 ug of DNA and incubated at room temperature for 20 minutes. DMEM-10% FBS was aspirated from the plate containing the cells. This mixture of Lipofectamine, Optimem, and DNA was then added to the CHO cells, along with 150 μl of Optimem. Plates were incubated at 370 Celsius for 3 days. After 3 days plates were spun for 5-7 minutes at 1200×g, and the supernatants were harvested. Supernatants were then tested for anti-CD20 antibodies by flow cytometry with binding to Wil2S (CD20+) and absence of binding to CHO (CD20 negative). FIG. 14 shows binding of 5 unique anti-CD20 antibodies selected using the protocol described above. Numerous additional binders were identified.

Alternate Panning with Vaccinia Virus and FPV to Eliminate Anti-Virus Antibody Responses FPV and vaccinia virus expressing antigens were used for in vitro panning. A phage display library was made from synthetic V gene sequences in a phagemid vector using standard methods. The library contained approximately 10$^{10}$ unique V gene combinations and the library had a titer of approximately 10$^{12}$ pfu/ml. The availability of antigen recombinants in two antigenically distinct background strains facilitates selection of antibodies against the desired antigen because anti-vector antibodies are easily removed by alternating virus for different rounds.

Tosylactivated MyOne DYNABEADS® (100 μL) were pulled down with a magnet and washed with 1 mL of PBS, two times. The beads were pulled down with the magnet, the PBS removed and the 3×10$^8$ pfu of FPV/CD20-FPV108 or control FPV were each added to 50 μl of beads. The beads and antigen-EEV were allowed to rotate at 37° C. for 18-20 hours. The beads were pelleted and the supernatant was removed. The beads were blocked with 1 mL of 1×PBS, 10% FBS and 0.5% BSA at 37° C. for 2 hours. The beads were pelleted and washed with 1 mL 1×PBS before being resuspended in 100 μL of 1×PBS for CD20 and 150 μl for control FPV. The phage library (1 ml, approximately 10$^{12}$ pfu) was blocked with 2% milk and 10% FBS for 30 minutes. The phage library was added to 50 μl beads couple with wt FPV for 30 min to deplete background and any anti-FPV binding. The beads were pulled down with a magnet and unbound phage was transfer to a fresh tube with a fresh 50 μl of beads coated with control FPV. The phage were allowed to bind for 30 minutes; unbound phage were removed as above and bound to control FPV/beads for third time for 30 minutes. Unbound phage were then transferred to a fresh tube and the CD20 FPV/bead was added. Phage were bound for 1 hour at RT with rotation. Unbound phage were removed by 10×1 ml washes in PBS/10% FBS and bound phage used to infect log phase TG1 cells in 2XYT/glucose for 1 hour at 370 with shaking. After the 1 hour, hyperphage and ampicillin were added and the cells were grown with shaking at 370 for 1 hour, and then pelleted by centrifugation, resuspended in 2XYT/Amp/Kanamycin and grown with shaking at 300 overnight. The next day the phage were harvested by PEG precipitation and resuspended in 1 ml PBS. The phage were then subjected to three additional rounds of panning as described above. For the second round of panning, MVA/CD20 and control MVA were used as panning antigens. For the third round FPV/CD20 and control FPV were used, and for the 4' round, MVA/CD20 and control MVA were used. After the fourth round of panning the Tg1 cells were infected for 1 hour with the bound phage and then grown overnight at 300 in 2XYT/Amp/Glucose to expand the plasmid.

The following day, the TG1 cells with the Rd 3 panned phagemid were centrifuged to pellet and then plasmid DNA was extracted (Qiagen HiSpeed Maxiprep kit, cat #12662). Expression cassette containing the linked heavy and light chains (variable light/constant light-RBS element-Variable Heavy) was subcloned as a pool into mammalian expression dual gene vector pEFDGV (Kan) using BsrG1 and NheI restriction sites and standard ligation and transformation protocols (pEFDGV contains the heavy constant to complete the antibody cassette upon cloning) The library was plated on 4 standard 150 mm LB AGAR plates containing 50 mg/mL Kanamycin (LB-Kan50) and incubated overnight at 37° C. A control vector only plate was included. Colonies were counted and background determined. Approximately 5000 colonies were harvested from the plates (10 ML LB/Glycerol per plate was applied to each plate and colonies were gently lifted from the agar surface using a sterile cell scraper) and plasmid DNA was extracted using Qiagen plasmid DNA kit. This pool was subsequently digested with SalI/BssHI to remove the RBS element and replace it with an IRES element for mammalian co-expression. Transformations were plated on 100 mm LB-Kan50 plates at various densities to ensure good colony separation and incubated overnight at 37° C. 94 colonies were picked into a 96 well deep well growth plate containing 1.6 mL/well LB/Kan50 and grown for 22 hrs at 37° C. A spot plate was arrayed to allow for future propagation of each individual clone in the future. Plasmid DNA was isolated in this format using the Qiagen turbo 96 kit. DNA concentration was measured by nanodrop and averaged to assign a single plate concentration and the DNA was handed off for transfection.

DNA was sequenced at Genewiz using two primers—Ef1F forward primer (5'-TGGAATTTGCCCTTTTTGAG-3') (SEQ ID NO: 13) for the light chain variable region and cGS reverse primer (5' AAGTAGTCCTTGACCAGGCAGCC-3') (SEQ ID NO: 14) for the heavy chain variable region.

For transfection, CHO-S cells were seeded at 50,000 cells per well in a 96 well plate the day before transfection in 125 μl DMEM-10% FBS. The next day 75 μl of a mixture of Lipofectamine 2000 (1.65 μl each well) and Optimem were added to 0.8 ug of DNA and incubated at room temperature for 20 minutes. DMEM-10% FBS was aspirated from the plate containing the cells. This mixture of Lipofectamine, Optimem, and DNA was then added to the CHO cells, along with 150 μl of Optimem. Plates were incubated at 370 Celsius for 3 days. After 3 days plates were spun for 5-7 minutes at 1200×g, and the supernatants were harvested. Supernatants were then tested for anti-CD20 antibodies by flow cytometry with binding to Wil2S (CD20+) and absence of binding to CHO (CD20 negative). FIG. 15 shows binding of 5 unique anti-CD20 antibodies selected by this protocol.

What is claimed is:

1. An isolated polynucleotide comprising: (a) a first nucleic acid fragment that encodes an integral membrane protein (IMP) or fragment thereof, wherein the IMP or fragment thereof comprises at least one extra-membrane region, at least one transmembrane domain and at least one intra-membrane region, and wherein a portion of the first nucleic acid fragment encoding at least one intra-membrane region is situated at the 5' or 3' end of the first nucleic acid fragment; and (b) a second nucleic acid fragment that encodes a fowlpox virus (FPV) FPV108 protein or functional fragment thereof, wherein the second nucleic acid fragment is fused in frame to a portion of the first nucleic acid fragment that encodes an intra-membrane region of the IMP; wherein a poxvirus infected cell comprising the polynucleotide can express an IMP-FPV108 fusion protein as part of the outer envelope membrane of an extracellular enveloped virion (EEV).

2. The polynucleotide of claim 1, wherein the second nucleic acid encodes FPV108 protein comprising the amino acid sequence SEQ ID NO: 2 or a functional fragment thereof.

3. The polynucleotide of claim 1, wherein the IMP is a multi-pass membrane protein comprising at least two transmembrane domains.

4. The polynucleotide of claim 3, wherein the IMP has an odd number of transmembrane domains, wherein the 5' end of the first nucleic acid fragment encodes an extra-membrane region, wherein the 3' end of the first nucleic acid fragment encodes an intra-membrane region, and wherein the 5' end of the second polynucleotide is fused to the 3' end of the first nucleic acid fragment.

5. The polynucleotide of claim 4, wherein the IMP comprises a G-protein coupled receptor (GPCR), the human frizzled-4 protein (FZD4), a CXC chemokine receptor CXCR, or a fragment thereof.

6. The polynucleotide of claim 3, wherein the IMP has an even number of transmembrane domains, and wherein both the 5' and 3' ends of the first nucleic acid fragment encode intra-membrane regions, and wherein the second nucleic acid fragment is fused to 3' end of the first nucleic acid fragment.

7. The polynucleotide of claim 6, wherein the IMP is human CD20 or CD39 protein, or a fragment thereof.

8. The polynucleotide of claim 1, which is operably associated with a poxvirus promoter.

9. The polynucleotide of claim 1, wherein the first and second nucleic acid fragments are directly fused.

10. The polynucleotide of claim 1, further comprising a third nucleic acid fragment encoding a heterologous peptide.

11. The polynucleotide of claim 10, wherein the heterologous peptide comprises a linker sequence, an amino acid tag or label, or a peptide or polypeptide sequence that facilitates purification.

12. The polynucleotide of claim 11, wherein the heterologous peptide comprises a histidine tag.

13. The polynucleotide of claim 1, which is operably associated with a poxvirus promoter.

14. The polynucleotide of claim 13, wherein the poxvirus promoter is p7.5, H5, or T7.

15. A poxvirus genome comprising the polynucleotide of claim 1.

16. The poxvirus genome of claim 15, wherein said genome is selected from i-s a vaccinia virus genome, a fowlpox virus genome, and a rabbit pox virus genome.

17. A recombinant poxvirus EEV comprising the poxvirus genome of claim 16.

18. A method of producing the recombinant poxvirus EEV of claim 17, comprising: (a) infecting a host cell permissive for vaccinia virus, fowlpox virus, or rabbit pox virus infectivity with a vaccinia virus, fowlpox virus or rabbit pox virus, respectively; and (b) recovering EEV released from the host cell.

19. A method to display an integral membrane protein (IMP) or fragment thereof in a native conformation comprising: (a) infecting host cells permissive for poxvirus infectivity with a recombinant poxvirus that expresses the IMP or fragment thereof as a fusion protein with the EEV-specific protein FPV108 or a membrane-associated functional fragment thereof encoded by the polynucleotide of claim 1, wherein EEV produced by the infected host cell comprise the IMP fusion protein as part of the EEV outer envelope membrane; (b) recovering EEV released from the host cell wherein the IMP or fragment thereof displays on the surface of the EEV in a native conformation.

20. The method of claim 19, wherein the IMP is a multi-pass membrane protein comprising at least two transmembrane domains.

21. The method of claim 20, wherein the IMP comprises (i) a G-protein coupled receptor (GPCR) comprising seven transmembrane domains, or a fragment thereof; (ii) the human frizzled-4 protein (FZD4), or a fragment thereof; or (iii) a CXC chemokine receptor, and wherein FPV108 is fused to the C-terminus of the IMP.

22. The method of claim 21, wherein the IMP comprises the CXC chemokine receptor CXCR4, or a fragment thereof.

23. The method of claim 19, wherein the IMP or fragment thereof has an even number of transmembrane domains, and wherein both the N-terminus and the C-terminus of the IMP or fragment thereof are intra-membrane.

24. The method of claim 23, wherein FPV108 is fused to the C-terminus of the IMP.

25. The method of claim 24, wherein the IMP is human CD20, or a fragment thereof.

26. A method to select antibodies that bind to a multi-pass membrane protein (IMP) comprising: (a) attaching the recombinant EEV of claim 17 to a solid support; (b) providing an antibody display library, wherein the library comprises display packages displaying a plurality of antigen binding domains; (c) contacting the display library with the EEV such that display packages displaying antigen binding domains that specifically binds to the IMP expressed on the EEV can bind thereto; (d) removing unbound display packages; and (e) recovering display packages that display an antigen binding domain specific for the IMP expressed on the EEV.

27. The method of claim 26 wherein the recombinant EEV are inactivated prior to attachment to the solid support.

28. A method to select antibodies that bind to a multi-pass membrane protein (IMP) comprising: (a) providing a first and second recombinant poxvirus EEV of claim 17, wherein the first and second recombinant poxvirus EEV are each generated in an antigenically distinct poxvirus; (b) immunizing an animal with the first recombinant poxvirus; (b) contacting a display library that comprises display packages displaying a plurality of antigen binding domains with the second recombinant poxvirus such that the display packages displaying antigen binding domains that specifically bind to the IMP expressed on the EEV can bind thereto, wherein said display library is generated from B cells isolated from the immunized mammal; (c) removing unbound display packages; and (d) recovering display packages that display an antigen binding domain specific for the IMP expressed on the second recombinant EEV.

29. The method of claim 28, wherein the first recombinant poxvirus EEV is a vaccinia virus EEV.

30. The method of claim 29, wherein the second recombinant poxvirus EEV is a fowlpox virus EEV.

31. A method to select antibodies or antigen-binding fragments thereof that bind to a multi-pass membrane protein (IMP), which comprises: (a) providing a recombinant poxvirus EEV of claim 17; (b) immunizing a mammal with the recombinant poxvirus EEV; (c) optionally immunizing the mammal with a second dose of the recombinant poxvirus EEV; (d) isolating serum from the immunized animal; and (e) isolating antibodies or antigen-binding fragments thereof that comprise an antigen binding domain specific for the IMP expressed on the recombinant poxvirus EEV.

* * * * *